(12) United States Patent
Leleti et al.

(10) Patent No.: US 12,064,433 B2
(45) Date of Patent: Aug. 20, 2024

(54) PYRIDONE A2R ANTAGONISTS

(71) Applicant: ARCUS BIOSCIENCES, INC., Hayward, CA (US)

(72) Inventors: Manmohan Reddy Leleti, Dublin, CA (US); Debashis Mandal, Fremont, CA (US); Dillon Harding Miles, Berkeley, CA (US); Jay Patrick Powers, Pacifica, CA (US); Brandon Reid Rosen, San Mateo, CA (US); Ehesan U I Sharif, Menlo Park, CA (US)

(73) Assignee: ARCUS BIOSCIENCES, INC., Hayward, CA (US)

( * ) Notice: Subject to any disclaimer, the term of this patent is extended or adjusted under 35 U.S.C. 154(b) by 564 days.

(21) Appl. No.: 17/263,016

(22) PCT Filed: Jul. 26, 2019

(86) PCT No.: PCT/US2019/043608
§ 371 (c)(1),
(2) Date: Jan. 25, 2021

(87) PCT Pub. No.: WO2020/023846
PCT Pub. Date: Jan. 30, 2020

(65) Prior Publication Data
US 2021/0161898 A1    Jun. 3, 2021

Related U.S. Application Data

(60) Provisional application No. 62/711,273, filed on Jul. 27, 2018.

(51) Int. Cl.
| A61K 33/243 | (2019.01) |
| A61K 31/282 | (2006.01) |
| A61K 31/517 | (2006.01) |
| A61K 31/519 | (2006.01) |
| A61K 31/704 | (2006.01) |
| A61K 45/06 | (2006.01) |
| C07D 401/14 | (2006.01) |
| C07D 405/14 | (2006.01) |

(52) U.S. Cl.
CPC .......... *A61K 31/517* (2013.01); *A61K 31/282* (2013.01); *A61K 31/519* (2013.01); *A61K 31/704* (2013.01); *A61K 33/243* (2019.01); *A61K 45/06* (2013.01); *C07D 401/14* (2013.01); *C07D 405/14* (2013.01)

(58) Field of Classification Search
CPC .. A61K 31/517; A61K 31/519; A61K 31/704; C07D 401/14; C07D 405/14; A61P 35/00
See application file for complete search history.

(56) References Cited

U.S. PATENT DOCUMENTS

| 8,916,601 B2 | 12/2014 | Chen et al. |
| 2007/0219221 A1 | 9/2007 | Zeng et al. |

FOREIGN PATENT DOCUMENTS

| WO | WO-2004092177 | 10/2004 | |
| WO | WO-2006091898 | 8/2006 | |
| WO | WO-2007109547 | 9/2007 | |
| WO | WO-2008156580 | 12/2008 | |
| WO | WO-2013130811 | 9/2013 | |
| WO | WO-2015002994 | 1/2015 | |
| WO | WO-2016126570 A1 * | 8/2016 | .......... A61K 31/517 |
| WO | WO-2018035072 A1 | 2/2018 | |
| WO | WO-2018136700 A1 | 7/2018 | |

OTHER PUBLICATIONS 1,2,3-Triazoles as Amide Bioisosteres: Discovery of a New Class of Potent HIV-1 Vif Antagonists J. Med. Chem. 2016, 59, 7677-7682 (Year: 2016).*
Safety and clinical activity of adenosine A2a receptor (A2aR) antagonist, CPI-444, in anti-PD1/PDL1 treatment-refractory renal cell (RCC) and non-small cell lung cancer (NSCLC) ASCO Annual meeting 2017, Jun. 5, 2017 (Year: 2017).*
A2aR antagonists: Next generation checkpoint blockade for cancer immunotherapy Comput Struct Biotechnol J. 2015,13,265-72 (Year: 2015).*
The 1,2,3-triazole ring as a bioisostere in medicinal chemistry Drug Discov. Today. 2017, 22(10), 1572-1581 (Year: 2017).*
International Search Report for PCT/US2019/043608 mailed Oct. 16, 2019, 3 pages.
PubChem CID 113633459, 3-(Quinazolin-2-ylamino)piperidin-2-one, deposited on Jan. 28, 2016, pp. 1-5.
Written Opinion of the ISA/US for PCT/US2019/043608, mailed Oct. 16, 2019, 4 pages.
Extended European Search Report for European Application No. 19841391.6 dated Mar. 24, 2022. 6 pages.
Zhang et al., Modern Drug Design, China Medical Science & Technology Press 2005, pp. 125-126.

* cited by examiner

*Primary Examiner* — Theodore R. Howell
(74) *Attorney, Agent, or Firm* — Sheppard Mullin Richter & Hampton LLP

(57) ABSTRACT

Compound that inhibit at least one of the $A_{2A}$ and $A_{2B}$ adenosine receptors, and compositions containing the compound and methods for synthesizing the compound, are described herein. Also described are the use of such compounds and compositions for the treatment of a diverse array of diseases, disorders, and conditions, including cancer- and immune-related disorders that are mediated, at least in part, by the adenosine $A_{2A}$ receptor and/or the adenosine $A_{2B}$ receptor.

25 Claims, No Drawings

PYRIDONE A2R ANTAGONISTS

CROSS-REFERENCES TO RELATED APPLICATIONS

This application is the U.S. National Stage entry under § 371 of International Application No. PCT/US2019/043608, filed Jul. 26, 2019, which claims the benefit of priority to U.S. Provisional Application Ser. No. 62/711,273, filed Jul. 27, 2018, the disclosures of which are incorporated herein by reference in their entireties.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Adenosine is a purine nucleoside compound comprising a complex of adenine and a ribose sugar molecule (ribofuranose). Adenosine occurs naturally in mammals and plays important roles in several biochemical processes, including energy transfer (as adenosine triphosphate and adenosine monophosphate) and signal transduction (as cyclic adenosine monophosphate). Adenosine also serves in processes associated with vasodilation, including cardiac vasodilation, and acts as a neuromodulator (e.g., it is thought to be involved in promoting sleep). In addition to its involvement in these biochemical processes, adenosine is used as a therapeutic antiarrhythmic agent to treat, for example, supraventricular tachycardia. As discussed further herein, tumors evade host responses by inhibiting immune function and promoting tolerance, and adenosine has been shown to play an important role in mediating tumor evasion of the immune system. Adenosine signaling through $A_{2A}$Rs and $A_{2B}$Rs, expressed on a variety of immune cell subsets and endothelial cells, has been established as having an important role in protecting tissues during inflammatory responses. As such, under certain conditions adenosine protects tumors from immune destruction (see, e.g., Fishman, P, et al. (2009) Handb Exp Pharmacol 193:399-441).

The adenosine receptors are a class of purinergic G protein-coupled receptors with adenosine as the endogenous ligand. The four types of adenosine receptors in humans are referred to as $A_1$, $A_{2A}$, $A_{2B}$ and $A_3$. Modulation of $A_1$ has been proposed for the management and treatment of, for example, neurological disorders, asthma, and heart and renal failure; $A_{2A}$ antagonists have been proposed for the management and treatment of, for example, Parkinson's disease; modulation of $A_{2B}$ has been proposed for the management and treatment of, for example, chronic pulmonary diseases, including asthma; and modulation of $A_3$ has been proposed for the management and treatment of, for example, asthma and chronic obstructive pulmonary diseases, glaucoma, cancer, and stroke.

Historically, modulators of adenosine receptors have been nonselective. This is acceptable in certain indications, such as where the endogenous agonist adenosine, which acts on all four adenosine receptors in cardiac tissue, is administered parenterally for the treatment of severe tachycardia. However, the use of sub-type selective adenosine receptor agonists and antagonists provides the potential for achieving desired outcomes while minimizing or eliminating adverse effects.

As such, there is a need in the art for sub-type selective adenosine receptor agonists. The present invention addresses this need and provides related advantages as well.

BRIEF SUMMARY OF THE INVENTION

The present invention relates to compounds that modulate the adenosine $A_{2A}$ receptor ($A_{2A}$R) and/or the adenosine $A_{2B}$ receptor ($A_{2B}$R), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by the adenosine $A_{2A}$ receptor ($A_{2A}$R) and/or the adenosine $A_{2B}$ receptor ($A_{2B}$R). Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to affect their activity by inhibition of the adenosine $A_{2A}$ receptor ($A_{2A}$R) and/or the adenosine $A_{2B}$ receptor ($A_{2B}$R), a precise understanding of the compounds' underlying mechanism of action is not required to practice the invention. It is envisaged that the compounds may alternatively affect their activity through direct or indirect inhibition of adenylyl cyclase. It is also envisaged that the compounds may affect their activity through inhibition of both $A_{2A}$ receptor ($A_{2A}$R) and/or the adenosine $A_{2B}$ receptor ($A_{2B}$R) as well as adenylyl cyclase. Although the compounds of the invention are generally referred to herein as adenosine $A_{2A}$ receptor ($A_{2A}$R) and/or the adenosine $A_{2B}$ receptor ($A_{2B}$R) inhibitors, it is to be understood that the term "$A_{2A}$R/$A_{2B}$R inhibitors" encompasses compounds that act individually through inhibition of $A_{2A}$R, $A_{2B}$R or adenylyl cyclase, and/or compounds that act through inhibition of $A_{2A}$R, $A_{2B}$R, and adenylyl cyclase.

The $A_{2A}$ and $A_{2B}$ cell surface adenosine receptors are found to be upregulated in various tumor cells. Thus, antagonists of the $A_{2A}$ and/or $A_{2B}$ adenosine receptors represent a new class of promising oncology therapeutics.

Activation of the $A_{2A}$ adenosine receptor results in inhibition of the immune response to tumors via suppression of T regulatory cell function and inhibition of natural killer cell cytotoxicity and tumor-specific CD4+/CD8+activity. Therefore, inhibition of this receptor subtype by specific antagonists may enhance immunotherapeutics in cancer therapy. Activation of the $A_{2B}$ adenosine receptor plays a role in the development of tumors via upregulation of the expression levels of angiogenic factors in microvascular endothelial cells. [See, e.g., P. Fishman et al., Handb Exp Pharmacol (2009); 193:399-441]. Moreover, adenosine receptor 2A blockade has been shown to increase the efficacy of anti-PD-I through enhanced anti-tumor T cell responses (P. Beavis, et al., Cancer Immunol Res DOI: 10.1158/2326-

6066.CIR-14-0211 Published 11 Feb. 2015). A more comprehensive discussion of the roles of the $A_{2A}$Rs and the $A_{2B}$Rs is set forth hereafter.

Adenosine 2A Receptor (A2A R)

The $A_{2A}$R (also referred to as ADORA2A) is a G protein-coupled receptor (GPCR), family members of which possess seven transmembrane alpha helices. Based on its crystallographic structure, the $A_{2A}$R comprises a ligand binding pocket distinct from that of other structurally determined GPCRs (e.g., the beta-2 adrenergic receptor).

As set forth elsewhere herein, adenosine is involved in mediating tumor evasion of the immune system. The $A_{2A}$R plays a critical, nonredundant role in mediating adenosine-induced anti-inflammatory responses. The $A_{2A}$R negatively regulates immune responses, and thus pharmacologic inhibition of $A_{2A}$R activation has been demonstrated to be a viable means of enhancing immunotherapy.

As noted above, activation of the $A_{2A}$R impacts the adaptive immune response; by way of example, the $A_{2A}$R protects the host from excessive tissue destruction by not only acutely inhibiting T-cell function, but by also promoting the development of regulatory T cells. Because $A_{2A}$R activation is a potent inhibitor of adaptive immune responses, tumor-derived adenosine has been implicated in blocking antitumor immunity.

In addition to its other roles, the $A_{2A}$R has been implicated in selectively enhancing anti-inflammatory cytokines, promoting the upregulation of PD-1 and CTLA-4, promoting the generation of LAG-3 and Foxp3+ regulatory T cells, and mediating the inhibition of regulatory T cells. PD-1, CTLA-4 and other immune checkpoints are discussed further herein. As all of these immunosuppressive properties have been identified as mechanisms by which tumors evade host responses, a cancer immunotherapeutic regimen that includes an $A_{2A}$R antagonist may result in enhanced tumor immunotherapy. See generally, Naganuma, M., et al. (2006) J Immunol 177:2765-769.

$A_{2A}$R antagonists likely play an important role in chemotherapy and radiation therapy. Mechanistically, the concomitant administration of $A_{2A}$R antagonists during chemotherapy or radiation therapy has been proposed to lead to the expansion of tumor-specific T cells while simultaneously preventing the induction of tumor-specific regulatory T cells. Furthermore, combining $A_{2A}$R antagonists with tumor vaccines is thought to provide at least an additive effect in view of their divergent mechanisms of action. Finally, $A_{2A}$R antagonists may most effectively be used in combination with tumor vaccines and other checkpoint blockers. By way of example, blocking PD-1 engagement as well as inhibiting the $A_{2A}$R might mitigate the ability of tumors to turn off tumor-specific effector T cells (see, e.g., Fishman, P, et al. (2009) Handb Exp Pharmacol 193:399-441). Moreover, adenosine signaling through the $A_{2A}$R receptor has been found to be a promising negative feedback loop, and preclinical studies have confirmed that blockade of $A_{2A}$R activation can markedly enhance anti-tumor immunity (Sitkovsky, M V, et al. (2014) Cancer Immun Res 2:598-605).

Adenosine 2B Receptor ($A_{2b}$R)

The $A_{2b}$R (also referred to as ADORA2B) is a GPCR found in many different cell types. It requires higher concentrations of adenosine for activation than other adenosine receptor subtypes (e.g., $A_1$R, $A_{2A}$R, and $A_3$R) (Fredholm BB, et al. (2001) Biochem Pharmacol 61:443-448). Such conditions have been seen in, for example, tumors where hypoxia is commonly observed. Contrary to the other adenosine receptor subtypes, the $A_{2B}$R may play an important role in pathophysiological conditions associated with massive adenosine release. Thus, selective blockade or stimulation of this adenosine receptor subtype may not interfere with the numerous important physiological functions of adenosine mediated via other adenosine receptor subtypes. However, the pathway leading to $A_{2B}$R-mediated inhibition is not fully understood.

Angiogenesis represents a pivotal mechanism for tumor growth. The angiogenesis process is highly regulated by an array of angiogenic factors and is triggered by adenosine under particular circumstances that are associated with hypoxia. The $A_{2B}$R is expressed in human microvascular endothelial cells, where it plays an important role in the regulation of the expression of angiogenic factors such as vascular endothelial growth factor (VEGF). In certain tumor types, hypoxia has been observed to cause an upregulation of $A_{2B}$Rs, suggesting that $A_{2B}$Rs play a critical role in mediating the effects of adenosine on angiogenesis. Thus, blockade of $A_{2B}$Rs may limit tumor growth by limiting the oxygen supply to the tumor cells. Furthermore, experiments involving adenylate cyclase activation indicate that $A_{2B}$Rs are the sole adenosine receptor subtype in certain tumor cells, suggesting that $A_{2B}$R antagonists may exhibit effects on particular tumor types (see, e.g., Feoktistov, I. et al. (2003) Circ Res 92:485-492).

Recent data complicate an understanding of the precise role of $A_{2B}$R modulators. As discussed above, data confirm that $A_{2B}$Rs play an important role in mediating the effects of adenosine on tumor growth and progression. Indeed, inhibition of angiogenesis and inhibition of ERK ½ phosphorylation represent the most interesting effects for a potential anticancer treatment based on $A_{2B}$R as a target. However, while inhibition of angiogenesis requires the use of $A_{2B}$R antagonists, inhibition of growth signaling via other clinically relevant pathways (e.g., the MAP kinase pathway) might be achieved through treatment with $A_{2B}$R agonists (see, e.g., Graham, S. et al. (2001) Eur J Pharmaol 420:19-26). The results of additional experimentation may indicate that both agonists and antagonists will provide useful options for treatment in combination with other therapeutic measures if used at different stages of the disease and its treatment.

In one particular aspect, provided herein are compounds having Formula (I):

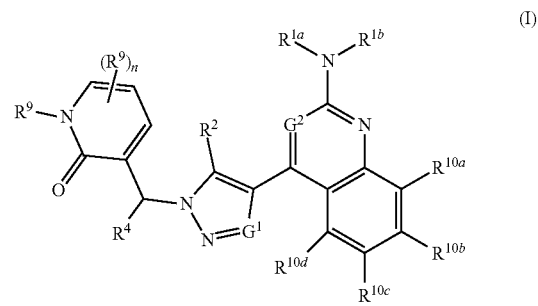

or a pharmaceutically acceptable salt, hydrate, or solvate thereof, wherein, $G^1$ is N or $CR^{3a}$;

$G^2$ is N or $CR^{3b}$;

$R^{3a}$ and $R^{3b}$ are each independently H or $C_{1-3}$ alkyl;

$R^{1a}$ and $R^{1b}$ are each independently selected from the group consisting of i) H
ii) $C_{1-8}$ alkyl optionally substituted with from 1-3 $R^5$ substituents,
iii) —$X^1$—O—$C_{1-8}$ alkyl optionally substituted with from 1-3 $R^5$ substituents,
iv) —C(O)—$R^6$,
v) Y optionally substituted with 1-3 $R^7$ substituents, and
vi) —$X^1$—Y optionally substituted with 1-3 $R^7$ substituents; or
vii) $R^{1a}$ and $R^{1b}$ together with the nitrogen to which they are attached form a 5-6 membered heterocycloalkyl ring optionally substituted with from 1-3 $R^8$ substituents, wherein the heterocycloalkyl has 0-2 additional heteroatom ring vertices selected from the group consisting of O, N, and S;
each Y is $C_{3-8}$ cycloalkyl or 4 to 6-membered heterocycloalkyl having 1-3 heteroatom ring vertices selected from the group consisting of O, N, and S;
$R^2$ and $R^4$ are each independently H or $C_{1-3}$ alkyl;
each $X^1$ is $C_{1-6}$ alkylene;
each $R^5$ is independently selected from the group consisting of hydroxyl, $C_{3-8}$ cycloalkyl, phenyl, —O-phenyl, —C(O)O$R^a$ and oxo;
each $R^6$ is $C_{1-8}$ alkyl or Y, each of which is optionally substituted with 1-3 substituents selected from the group consisting of hydroxyl, —O-phenyl, phenyl, and —O—$C_{1-8}$ alkyl;
each $R^7$ is independently selected from the group consisting of $C_{1-8}$ alkyl, hydroxyl, —O—$C_{1-8}$ alkyl, oxo, and C(O)O$R^a$;
each $R^8$ is independently selected from the group consisting of $C_{1-8}$ alkyl, hydroxyl, and oxo; the subscript n is 0, 1, 2 or 3;
each $R^9$ is independently selected from the group consisting of $C_{1-8}$ alkyl, —O—$C_{1-8}$ alkyl, —$X^1$—O—$C_{1-8}$ alkyl, —O—$X^1$—O—$C_{1-8}$ alkyl, —$X^1$—O—$X^1$—O—$C_{1-8}$ alkyl, —C(O)O$R^a$, halogen, cyano, —N$R^bR^c$, Y, —$X^1$-$C_{3-8}$ cycloalkyl, and —$X^2$—Z, wherein $X^2$ is selected from the group consisting of $C_{1-6}$ alkylene, —$C_{1-6}$ alkylene-O—, —$C_{1-4}$ alkylene-O—$C_{1-4}$ alkylene-, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$;
each of $R^{10a}$, $R^{10b}$, $R^{10c}$ and $R^{10d}$ is independently selected from the group consisting of H, $C_{1-8}$ alkyl, halo, cyano, —O—$C_{1-8}$ alkyl, —$X^1$—O—$C_{1-8}$ alkyl, —O—$X^1$—O—$C_{1-8}$ alkyl, —S(O)$_2$—$C_{1-6}$ alkyl, —C(O)N$R^dR^e$, and 4-6-membered heteroaryl having from 1-3 heteroatom ring vertices selected from the group consisting of O, N, and S, wherein each of said $R^{10a-d}$ substituents is optionally substituted with 1-3 $R^{12}$, or two of $R^{10a}$, $R^{10b}$, $R^{10c}$ and $R^{10d}$ on adjacent ring vertices are optionally combined to form a 5-membered heterocyclic ring optionally substituted with 1-2 halogens;
each $R^{11}$ is independently selected from the group consisting of hydroxyl, oxo, halo, cyano, —N$R^dR^c$, —C(O)O$R^a$, phenyl, $C_{3-8}$ cycloalkyl, and $C_{1-4}$ alkyl optionally substituted with —C(O)O$R^a$;
each $R^{12}$ is independently selected from the group consisting of halo, cyano, hydroxy, —C(O)O$R^a$; and
each $R^a$ is H or $C_{1-6}$ alkyl;
each $R^b$ and $R^c$ are independently selected from the group consisting of H, $C_{1-8}$ alkyl, —S(O)$_2$—$C_{1-6}$ alkyl, —C(O)O$R^a$, and —$X^1$—C(O)O$R^a$; and each $R^d$ and $R^e$ are independently selected from the group consisting of H, $C_{1-8}$ alkyl, —S(O)$_2$—$C_{1-6}$ alkyl.

In some embodiments, provided herein are methods for treating or preventing cancer in a subject (e.g., a human) comprising administering to the subject a therapeutically effective amount of at least one $A_{2A}R/A_{2B}R$ inhibitor described herein. In some embodiments, provided herein are methods of treating or preventing a cancer in a subject by administering to the subject at least one of the compounds described herein in an amount effective to reverse or stop the progression of $A_{2A}R$-mediated immunosuppression. In some embodiments, the $A_{2A}R$-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell lung carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer or Kaposi's sarcoma. Cancers that are candidates for treatment with the compounds and compositions of the present invention are discussed further hereafter.

Also provided herein are methods of treating a subject receiving a bone marrow transplant or peripheral blood stem cell transplant by administering a therapeutically effective amount of an $A_{2A}R/A_{2B}R$ inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, provided herein are methods for treating or preventing an infective disorder (e.g., a viral infection) in a subject (e.g., a human) comprising administering to the subject a therapeutically effective amount of at least one $A_{2A}R/A_{2B}R$ inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, provided herein are methods for treating or preventing an immune-related disease, disorder or condition in a subject (e.g., a human), comprising administering to the subject a therapeutically effective amount of at least one $A_{2A}R/A_{2B}R$ inhibitor described herein. Examples of immune-related diseases, disorders and conditions are described hereafter.

Other diseases, disorders and conditions that can be treated or prevented, in whole or in part, by modulation of $A_{2A}R/A_{2B}R$ activity are candidate indications for the $A_{2A}R/A_{2B}R$ inhibitor compounds as provided herein.

Also provided herein is the use of the described $A_{2A}R/A_{2B}R$ inhibitors in combination with one or more additional agents. The one or more additional agents may have some adenosine $A_{2A}$ receptor and/or adenosine $A_{2B}$ receptor modulating activity; alternatively, they may function through distinct mechanisms of action. In some embodiments, such agents comprise radiation (e.g., localized radiation therapy or total body radiation therapy) and/or other treatment modalities of a non-pharmacological nature. When combination therapy is utilized, the compound(s) described herein and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In particular embodiments, provided herein are methods wherein the $A_{2A}R/A_{2B}R$ inhibitors described herein are used in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors. Immune checkpoint inhibitors, and combination therapy therewith, are discussed in detail elsewhere herein.

In other embodiments, provided herein are methods for treating cancer in a subject, comprising administering to the subject a therapeutically effective amount of at least one $A_{2A}R/A_{2B}R$ inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin, carboplatin and oxaliplatin; bioreductive alkylators such as mitomycin, procarbazine, dacarbazine and altretamine); anthracycline-based therapies (e.g., doxorubicin, daunorubicin, epirubicin and idarubicin); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate, trimetrexate and pemetrexed; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the $A_{2A}R/A_{2B}R$ inhibitors in combination with other agents known in the art (e.g., arsenic trioxide) and other chemotherapeutic agents developed in the future.

In some embodiments, provided herein are methods of treating cancer in which a therapeutically effective amount of an $A_{2A}R/A_{2B}R$ inhibitor described herein is administered in combination with at least one chemotherapeutic agent, resulting in a cancer survival rate greater than the cancer survival rate observed by administering either alone. In further embodiments drawn to methods of treating cancer, the administration of a therapeutically effective amount of an $A_{2A}R/A_{2B}R$ inhibitor described herein in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one $A_{2A}R/A_{2B}R$ inhibitor described herein and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an $A_{2A}R/A_{2B}R$ inhibitor in conjunction with at least one chemotherapeutic agent and/or radiation therapy, wherein the resulting rejection of tumor cells is greater than that obtained by administering either the $A_{2A}R/A_{2B}R$ inhibitor, the chemotherapeutic agent or the radiation therapy alone.

In further embodiments, the present invention provides methods for treating cancer in a subject, comprising administering to the subject a therapeutically effective amount of at least one $A_{2A}R/A_{2B}R$ inhibitor and at least one immunomodulator other than an $A_{2A}R/A_{2B}R$ inhibitors. In particular embodiments, the at least one immunomodulator is selected from the group consisting of CD40L, B7, B7RP1, anti-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-a/-13, M-CSF, IL-3, GM-CSF, IL-13, anti-IL-10 and indoleamine 2,3-dioxygenase 1 (IDO1). Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one $A_{2A}R/A_{2B}R$ inhibitor described herein and a therapeutically effective amount of an anti-infective agent(s).

In some embodiments of the present invention, the additional therapeutic agent is a cytokine, including, for example granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the compounds described herein to treat (either alone or as a component of combination therapy) infection is discussed further hereafter.

In additional embodiments, treatment of an infective disorder is effected through the co-administration of a vaccine in combination with administration of a therapeutically effective amount of an $A_{2A}R/A_{2B}R$ inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-C SF). In particular embodiments, the vaccine includes one or more immunogenic peptides and/or dendritic cells.

In some embodiments, the present invention contemplates methods of using the compounds described herein in combination with one or more antimicrobial agents.

In certain embodiments drawn to treatment of an infection by administering an $A_{2A}R/A_{2B}R$ inhibitor and at least one additional therapeutic agent, a symptom of infection observed after administering both the $A_{2A}R/A_{2B}R$ inhibitor and the additional therapeutic agent is improved over the same symptom of infection observed after administering either alone. In some embodiments, the symptom of infection observed can be reduction in viral load, increase in CD4+ T cell count, decrease in opportunistic infections, increased survival time, eradication of chronic infection, or a combination thereof.

BRIEF DESCRIPTION OF THE DRAWINGS

NOT APPLICABLE

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Provided herein, for example, are compounds and compositions for inhibition of the adenosine $A_{2A}$ receptor ($A_{2A}R$) and/or the adenosine $A_{2B}$ receptor ($A_{2B}R$), and pharmaceutical compositions comprising the same. Also provided herein are, for example, methods of treating or preventing a disease, disorder or condition, or a symptom thereof, mediated by inhibition of adenosine $A_{2A}$ receptor ($A_{2A}R$) and/or the adenosine $A_{2B}$ receptor ($A_{2B}R$).

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_5$-6. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups, often referred to as $X^1$ or $X^2$ groups in the present application, can be substituted or unsubstituted. When a group comprising $X^1$ or $X^2$ is optionally substituted, it is understood that the optional substitutions may be on the alkylene portion of the moiety.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. In some embodiments, the cycloalkyl compounds of the present disclosure are monocyclic $C_{3-6}$ cycloalkyl moieties.

The term "heterocycloalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "〰", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse).

For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, and alkynyl) can be a variety of groups selected from: halogen, —OR', —NR'R", —SR', —SiR'R"R"', —OC(O) R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy, oxo, cycloalkyl and heterocycloalkyl in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Optional substituents for the cycloalkyl and heterocycloalkyl radicals can be a variety of groups selected from: alkyl optionally substituted with C(O)OR', halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN (cyano), —NO$_2$, aryl, aryloxy and oxo. R', R" and R'" each independently refer to hydrogen, unsubstituted $C_{1-8}$ alkyl, unsubstituted aryl, aryl substituted with 1-3 halogens, $C_{1-8}$ alkoxy or $C_{1-8}$ thioalkoxy groups, or unsubstituted aryl-$C_{1-4}$ alkyl groups.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-6 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2.

Alternatively, two of the substituents on adjacent atoms of the aryl or heteroaryl ring may optionally be replaced with a substituent of the formula -A-(CR$^f$R$^g$)$_r$—B—, wherein A and B are independently —CH$_2$—, —O—, —NH—, —S—, —S(O)—, —S(O)$_2$—, —S(O)$_2$NR'— or a single bond, r is an integer of from 1 to 3, and R$^f$ and R$^g$ are each independently H of halogen. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'- and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are described in more detail elsewhere herein.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention may exist in multiple crystalline or amorphous forms. In general, all physical forms are equivalent for the uses contemplated by the present invention and are intended to be within the scope of the present invention.

Certain compounds of the present invention may be present, under particular conditions, as polymorphs. Polymorphism refers to the ability of a solid material to exist in more than one crystal structure form or phase, wherein the molecules in the crystal lattice have different arrangements or conformations. If such types of differences exist due to packing it is referred to as "packing polymorphism", and if they exist due to differences in conformation it is referred to as "conformational polymorphism". Different polymorphs of the same compound often display different physical properties, including packing properties, spectroscopic properties, thermodynamic properties, solubility, and melting point; kinetic properties such as rate of dissolution and stability; and mechanical properties such as hardness and tensile strength. Polymorphs can be classified as one of two types according to their stability with respect to different ranges of temperature and pressure. In a monotropic system, only one polymorph (i.e., monotrope) is stable, and it exhibits lower free energy content and solubility at all temperatures and pressure below melting point. In an enantiotropic system, one polymorph is stable at a certain temperature and pressure, while the other polymorph(s) is stable at various temperatures and pressure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of $A_{2A}R/A_{2B}R$, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of $A_{2A}R/A_{2B}R$ or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an $A_{2A}R/A_{2B}R$ inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an $A_{2A}R/A_{2B}R$ inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of $A_{2A}R/A_{2B}R$, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Adenosine $A_{2A}$ Receptor and Adenosine $A_{2B}$ Receptor and Inhibition Thereof As set forth above, although a precise understanding of the underlying mechanism of action by which the compounds of the present invention effect their activity is not required to practice the invention, the compounds (or a subset thereof) are believed to inhibit adenosine $A_{2A}$ receptor ($A_{2A}R$) and/or the adenosine $A_{2B}$ receptor ($A_{2B}R$). Alternatively, the compounds (or a subset thereof) may inhibit adenylyl cyclase function. The compounds (or a subset thereof) may also have inhibitor activity on the $A_{2A}$ receptor ($A_{2A}R$), the adenosine $A_{2B}$ receptor ($A_{2B}R$) as well as adenylyl cyclase. Although the compounds of the invention are generally referred to herein as adenosine $A_{2A}$ receptor ($A_{2A}R$) and/or the adenosine $A_{2B}$ receptor ($A_{2B}R$) inhibitors, it is to be understood that the term "$A_{2A}R/A_{2B}R$ inhibitors" encompasses compounds that act individually through inhibition of $A_{2A}R$, $A_{2B}R$ or adenylyl cyclase, and/or compounds that act through inhibition of $A_{2A}R$, $A_{2B}R$, and adenylyl cyclase.

Identification of adenosine $A_{2A}$ Receptor and adenosine $A_{2B}$ Receptor inhibitors Possessing Desirable Characteristics The present invention is drawn, in part, to the identification of inhibitors of the adenosine $A_{2A}$ receptor and/or the adenosine $A_{2B}$ receptor with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Compounds of the Invention

In one particular aspect, provided herein are compounds having Formula (I):

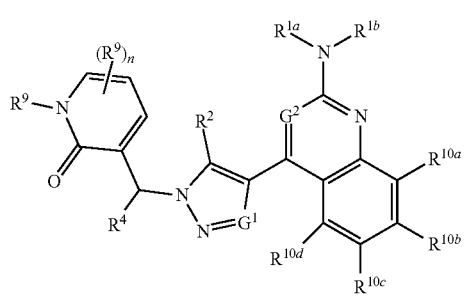

or a pharmaceutically acceptable salt, hydrate, or solvate thereof, wherein, $G^1$ is N or $CR^{3a}$;
$G^2$ is N or $CR^{3b}$;
$R^{3a}$ and $R^{3b}$ are each independently H or $C_{1-3}$ alkyl;
$R^{1a}$ and $R^{1b}$ are each independently selected from the group consisting of
  i) H
  ii) $C_{1-8}$ alkyl optionally substituted with from 1-3 $R^5$ substituents,
  iii) —$X^1$—O—$C_{1-8}$ alkyl optionally substituted with from 1-3 $R^5$ substituents,
  iv) —C(O)—$R^6$,
  v) Y optionally substituted with 1-3 $R^7$ substituents, and
  vi) —$X^1$—Y optionally substituted with 1-3 $R^7$ substituents; or
  vii) $R^{1a}$ and $R^{1b}$ together with the nitrogen to which they are attached form a 5-6 membered heterocycloalkyl ring optionally substituted with from 1-3 $R^8$ substituents, wherein the heterocycloalkyl has 0-2 additional heteroatom ring vertices selected from the group consisting of O, N, and S;

each Y is $C_{3-8}$ cycloalkyl or 4 to 6-membered heterocycloalkyl having 1-3 heteroatom ring vertices selected from the group consisting of O, N, and S;
$R^2$ and $R^4$ are each independently H or $C_{1-3}$ alkyl;
each $X^1$ is $C_{1-6}$ alkylene;
each $R^5$ is independently selected from the group consisting of hydroxyl, $C_3$-s cycloalkyl, phenyl, —O-phenyl, —C(O)OR$^a$ and oxo;
each $R^6$ is $C_{1-8}$ alkyl or Y, each of which is optionally substituted with 1-3 substituents selected from the group consisting of hydroxyl, —O-phenyl, phenyl, and —O—$C_{1-8}$ alkyl;
each $R^7$ is independently selected from the group consisting of $C_{1-8}$ alkyl, hydroxyl, —O—$C_{1-8}$ alkyl, oxo, and C(O)OR$^a$;
each $R^8$ is independently selected from the group consisting of $C_{1-8}$ alkyl, hydroxyl, and oxo; the subscript n is 0, 1, 2 or 3;
each $R^9$ is independently selected from the group consisting of $C_{1-8}$ alkyl, —O—$C_{1-8}$ alkyl, —$X^1$—O—$C_{1-8}$ alkyl, —O—$X^1$—O—$C_{1-8}$ alkyl, —$X^1$—O—$X^1$—O—$C_{1-8}$ alkyl, —C(O)OR$^a$, halogen, cyano, —NR$^b$R$^c$, Y, —$X^1$-$C_{3-8}$ cycloalkyl, and —$X^2$—Z, wherein $X^2$ is selected from the group consisting of $C_{1-6}$ alkylene, —$C_{1-6}$ alkylene-O—, —$C_{1-4}$ alkylene-O—$C_{1-4}$ alkylene-, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$;
each of $R^{10a}$, $R^{10b}$, $R^{10c}$ and $R^{10d}$ is independently selected from the group consisting of $C_{1-8}$ alkyl, halo, cyano, —O—$C_{1-8}$ alkyl, —$X^1$—O—$C_{1-8}$ alkyl, —O—$X^1$—O—$C_{1-8}$ alkyl, —S(O)$_2$—$C_{1-6}$ alkyl, —C(O)NR$^d$R$^e$, and 4-6-membered heteroaryl having from 1-3 heteroatom ring vertices selected from the group consisting of O, N, and S, wherein each of said $R^{10a-d}$ substituents is optionally substituted with 1-3 $R^{12}$, or two of $R^{10a}$, $R^{10b}$, $R^{10c}$ and $R^{10d}$ on adjacent ring vertices are optionally combined to form a 5-membered heterocyclic ring optionally substituted with 1-2 halogens;
each $R^{11}$ is independently selected from the group consisting of hydroxyl, oxo, halo, cyano, —NR$^d$R$^e$, —C(O)OR$^a$, phenyl, $C_{3-8}$ cycloalkyl, and $C_{1-4}$ alkyl optionally substituted with C(O)OR$^a$;
each $R^{12}$ is independently selected from the group consisting of halo, cyano, hydroxy, —C(O)OR$^a$; and
each $R^a$ is H or $C_{1-6}$ alkyl;
each $R^b$ and $R^c$ are independently selected from the group consisting of H, $C_{1-8}$ alkyl, —S(O)$_2$—$C_{1-6}$ alkyl, —C(O)OR$^a$, and —$X^1$—C(O)OR$^a$; and
each $R^d$ and $R^e$ are independently selected from the group consisting of H, $C_{1-8}$ alkyl, —S(O)$_2$—$C_{1-6}$ alkyl.

In some selected embodiments, the compound of Formula (I) is represented by Formula (Ia)

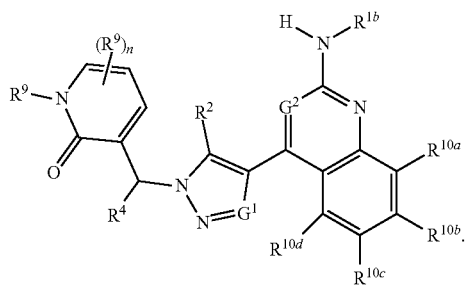

(Ia)

In some selected embodiments, the compound of Formula (I) is represented by Formula (Ib)

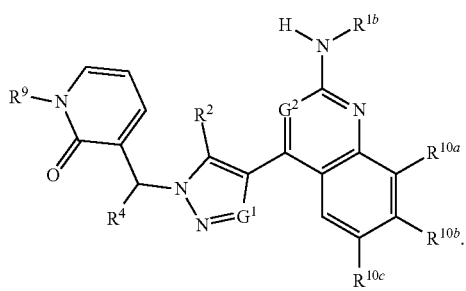

(Ib)

In some selected embodiments, compounds of Formula (I), (Ia), and (Ib) are provided wherein at least one $R^{10}$ is methoxy.

In some selected embodiments, the compound of Formula (I) is represented by Formula (Ic)

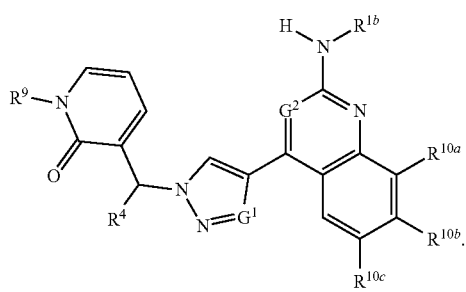

(Ic)

In some selected embodiments, the compound of Formula (I) is represented by Formula (Id)

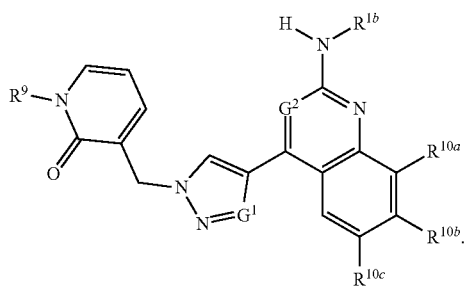

(Id)

In some selected embodiments, compounds of Formula (I), (Ia), (Ib), (Ic), and (Id) are provided wherein each $R^9$ is independently selected from the group consisting of $C_{1-8}$ alkyl, —O—$C_{1-8}$ alkyl, —$X^1$—O—$C_{1-8}$ alkyl, —O—$X^1$—O—$C_{1-8}$ alkyl, —$X^1$—O—$X^1$—O—$C_{1-8}$ alkyl, wherein each of said $R^9$ substituents is optionally substituted with 1-3 $R^{11}$.

In some selected embodiments, compounds of Formula (I), (Ia), (Ib), (Ic), and (Id) are provided wherein each $R^9$ is independently selected from the group consisting of —C(O)OR$^a$, —NR$^b$R$^c$, Y, —$X^1$-$C_3$-s cycloalkyl, and —$X^2$—Z, wherein $X^2$ is selected from the group consisting of $C_{1-6}$ alkylene, —$C_{1-6}$ alkylene-O—, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$.

In some selected embodiments, the compound of Formula (I) is represented by Formula (Ie)

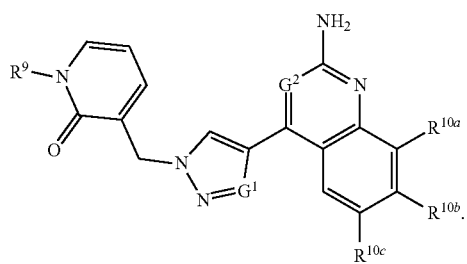

(Ie)

In some selected embodiments, the compound of Formula (I) is represented by Formula (If)

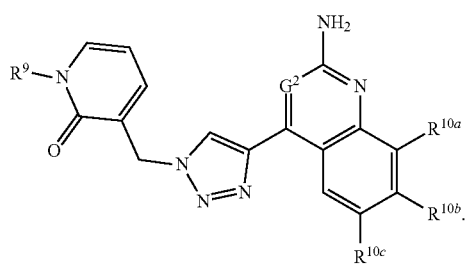

(If)

In some selected embodiments, the compound of Formula (I) is represented by Formula (Ig)

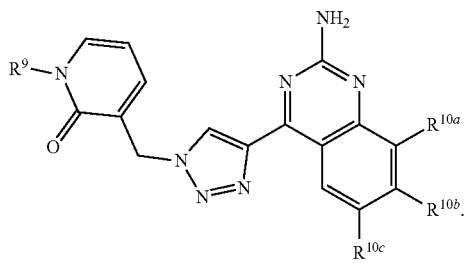

(Ig)

In some selected embodiments, the compound of Formula (I) is represented by Formula (Ih)

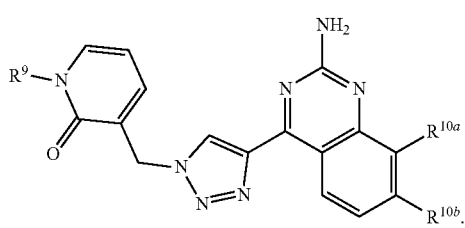

(Ih)

In some selected embodiments, the compound of Formula (I) is represented by Formula (Ii)

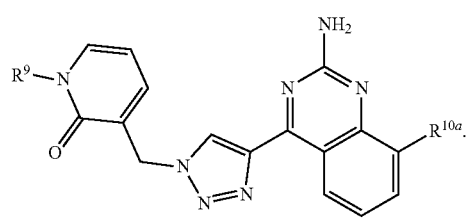

(Ii)

In some selected embodiments, compounds provided herein are selected from the group consisting of:

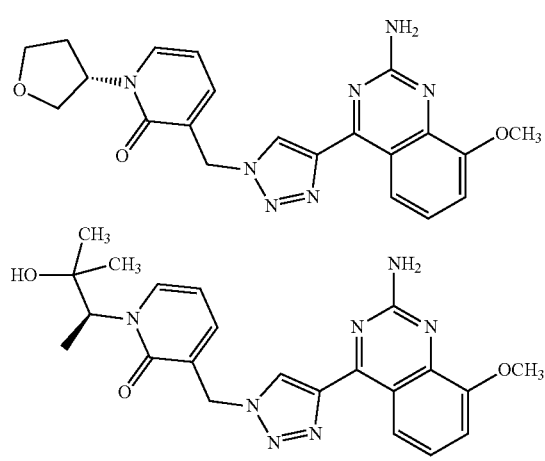

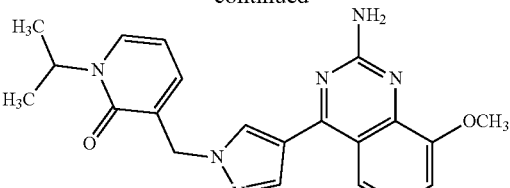

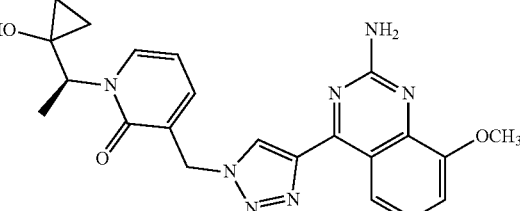

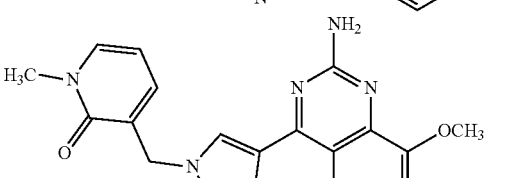

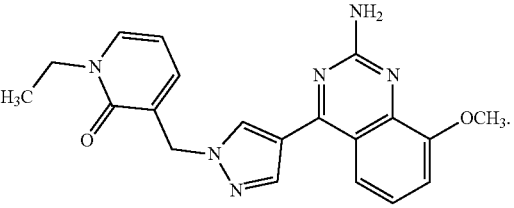

and

In some selected embodiments, any one compound of Table 1 is provided.

Methods of Synthesis

In general, the compounds provided herein can be prepared by conventional methods as described in the Examples below.

Prodrugs and Other Means of Drug Delivery and/or Half-Life Extension

In some aspects of the present invention, compounds described herein are administered in prodrug form.

In order to effect extension of therapeutic activity, drug molecules may be engineered to utilize carriers for delivery. Such carriers are either used in a non-covalent fashion, with the drug moiety physicochemically formulated into a solvent-carrier mixture, or by permanent covalent attachment of a carrier reagent to one of the drug moiety's functional groups (see generally WO 20150202317).

Several non-covalent approaches are favored. By way of example, but not limitation, in certain embodiments depot formulations comprising non-covalent drug encapsulation into polymeric carriers are employed. In such formulations, the drug molecule is combined with carrier material and processed such that the drug molecule becomes distributed inside the bulk carrier. Examples include microparticle polymer-drug aggregates (e.g., Degradex® Microspheres (Phosphorex, Inc.)), which are administered as an injectable suspension; polymer-drug molecule aggregates formulated as gels (e.g., Lupron Depot® (AbbVie Inc.)), which are administered as a single bolus injection; and liposomal formulations (e.g., DepoCyt® (Pacira Pharmaceuticals)), where the carrier may be a polymeric or non-polymeric entity capable of solubilizing the drug. In these formulations, release of the drug molecule may occur when the carrier swells or physically deteriorates. In other instances, chemical degradation allows diffusion of the drug into the biological environment; such chemical degradation processes may be autohydrolytic or enzyme-catalyzed. Among other limitations, non-covalent drug encapsulation requires prevention of uncontrolled release of the drug, and dependence of the release mechanism of the drug upon biodegradation may cause interpatient variability.

In particular embodiments, drug molecules, including both small molecules and large molecules, are conjugated to a carrier through permanent covalent bonds. Certain small molecule therapeutics that exhibit low solubility in aqueous fluids may be solubilized by conjugation to hydrophilic polymers, examples of which are described elsewhere herein. Regarding large molecule proteins, half-life extension may be achieved by, for example, permanent covalent modification with a palmitoyl moiety, and by permanent covalent modification with another protein that itself has an extended half-life (e.g., Albuferon®). In general, drug molecules show decreased biological activity when a carrier is covalently conjugated to the drug.

In certain instances, limitations associated with either drug molecules comprising non-covalent polymer mixtures or permanent covalent attachment may be successfully addressed by employing a prodrug approach for chemical conjugation of the drug to the polymer carrier. In this context, therapeutic agents that are inactive or less active than the drug moiety itself are predictably transformed into active molecular entities. The reduced biological activity of the prodrug as compared to the released drug is advantageous if a slow or controlled release of the drug is desired. In such instances, release of the drug occurs over time, thereby reducing the necessity of repeated and frequent administration of the drug. A prodrug approach may also be advantageous when the drug moiety itself is not absorbed, or has less than optimal absorption, in the gastrointestinal tract; in these instances, the prodrug facilitates absorption of the drug moiety and is then cleaved off at some later time (e.g., via first-pass metabolism). The biologically active drug molecule is typically linked to the polymeric carrier moiety by a temporary bond formed between the carrier moiety and a hydroxy, amino or carboxy group of the drug molecule.

The approaches described above are associated with several limitations. Prodrug activation may occur by enzymatic or non-enzymatic cleavage of the temporary bond between the carrier and the drug molecule, or a sequential combination of both (e.g., an enzymatic step followed by a non-enzymatic modification). In an enzyme-free in vitro environment (e.g., an aqueous buffer solution), a temporary bond such as an ester or amide may undergo hydrolysis, but the corresponding rate of hydrolysis may be such that it is outside the therapeutically useful range. In contrast, in an in vivo environment, esterases or amidases are typically present, and the esterases and amidases may cause significant catalytic acceleration of the kinetics of hydrolysis from two-fold up to several orders of magnitude (see, e.g., Greenwald et al., (1999) J Med Chem 42(18):3857-67).

As described herein, prodrugs may be classified as i) bioprecursors and ii) carrier-linked prodrugs. Bioprecursors do not contain a carrier group and are activated by the metabolic creation of a functional group. In contrast, in carrier-linked prodrugs the active substance is conjugated to a carrier moiety via a temporary linkage at a functional group of the bioactive entity. Preferred functional groups are hydroxyl or amino groups. Both the attachment chemistry and hydrolysis conditions depend on the type of functional group employed. The carrier may be biologically inert (e.g., PEG) or may have targeting properties (e.g., an antibody). Cleavage of the carrier moiety of a carrier-linked prodrug results in the bioactive entity of interest, and the nature of the deprotected functional group of the bioactive entity often contributes to its bioactivity.

The patent and scientific literature describe many macromolecular prodrugs where the temporary linkage is a labile ester bond. In these cases, the functional group of the bioactive entity is either a hydroxyl group or a carboxylic acid (see, e.g. Cheng et al. (2003) Bioconjugate Chem 14:1007-17). In addition, it is often advantageous for biomacromolecules and certain small molecule drugs to link the carrier to an amino group(s) of the bioactive entity (e.g., the N-terminus or lysine amino groups of proteins). During preparation of the prodrug, the amino groups may be more chemoselectively addressed due to their greater nucleophilicity compared to hydroxylic or phenolic groups. This is especially relevant for proteins and peptides containing a great variety of different reactive functionalities, where non-selective conjugation reactions lead to undesired product mixtures requiring extensive characterization or purification, thus decreasing reaction yield and therapeutic efficiency of the active moiety.

In general, amide bonds are more stable against hydrolysis than ester bonds, and the rate of cleavage of the amide bond may be too slow for therapeutic utility in a carrier-linked prodrug. As a result, it may be advantageous to add structural chemical components in order to effect control over the cleavability of the prodrug amide bond. These additional cleavage-controlling chemical components that are provided neither by the carrier entity nor by the drug are generally referred to as "linkers". Prodrug linkers can have a major effect on the rate of hydrolysis of temporary bond, and variation of the chemical nature of the linkers often results in particular properties. Prodrug activation of amine-containing biologically active moieties by specific enzymes for targeted release requires that the structure of the linker display a structural motif recognized as a substrate by a corresponding endogenous enzyme. In these cases, the cleavage of the temporary bond occurs in a one-step process which is catalyzed by the enzyme. For example, the enzymatic release of cytarabin is effected by the protease plasmin, which concentration is relatively high in various kinds of tumor mass.

Interpatient variability is a major drawback of predominant enzymatic cleavage. Enzyme levels may differ significantly between subjects resulting in biological variation of prodrug activation by the enzymatic cleavage. Enzyme levels may also vary depending on the site of administration (e.g., for subcutaneous injection, certain areas of the body yield more predictable therapeutic effects than others). In addition, it is difficult to establish an in vivo—in vitro correlation of the pharmacokinetic properties for enzyme-dependent carrier-linked prodrugs.

Other carrier prodrugs employing temporary linkages to amino groups in the drug moiety are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino group of the drug molecule through a second temporary linkage (e.g., a carbamate). The stability or susceptibility to hydrolysis of the second temporary linkage is dependent on the presence or absence of the masking group. In the presence of the masking group, the second temporary linkage is highly stable and unlikely to release the drug molecule with therapeutically useful kinetics, whereas in the absence of the masking group this linkage becomes highly labile, resulting in rapid cleavage and release of the drug moiety.

The cleavage of the first temporary linkage is the rate-limiting step in the cascade mechanism. The first step may induce a molecular rearrangement of the activating group (e.g., a 1,6-elimination as described in Greenwald et al. (1999) J Med Chem 42:3657-67), and the rearrangement renders the second temporary linkage much more labile such that its cleavage is induced. Ideally, the cleavage rate of the first temporary linkage is identical to the desired release rate for the drug molecule in a given therapeutic scenario. In addition, it is desirable that the cleavage of the second temporary linkage be substantially instantaneous after its lability has been induced by cleavage of the first temporary bond.

Another embodiment comprises polymeric amino-containing prodrugs based on trimethyl lock lactonization (see, e.g., Greenwald et al. (2000) J Med Chem 43(3):457-87). In this prodrug system, substituted o-hydroxyphenyl-dimethylpropionic acid is linked to PEG by an ester, carbonate, or carbamate group as a first temporary linkage and to an amino group of a drug molecule by means of an amide bond as a second temporary linkage. The rate-determining step in drug release is the enzymatic cleavage of the first linkage, which is followed by fast amide cleavage by lactonization, releasing an aromatic lactone side product. The primary disadvantage of the prodrug systems described by Greenwald et al. is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

In certain embodiments of cascade prodrugs comprising aromatic activating groups based on 1,6-elimination, the masking group is structurally separate from the carrier. This may be effected by employing a stable bond between the polymer carrier and the activating group, wherein the stable bond does not participate in the cascade cleavage mechanism. If the carrier is not serving as a masking group and the activating group is coupled to the carrier by means of a stable bond, release of potentially toxic side products (such as the activating group) is avoided. The stable attachment of the activating group and the polymer also suppresses the release of drug-linker intermediates with undefined pharmacology.

A first example of the approach described in the preceding paragraph comprises a polymeric prodrug system based on a mandelic acid activating group (see, e.g., Shabat et al. (2004) Chem Eur J 10:2626-34). In this approach the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released; the activating group is still connected to the polyacrylamide polymer after drug release. A similar prodrug system is based on a mandelic acid activating group and an enzymatically cleavable ester-linked masking group (see, e.g., Lee et al. (2004) Angew Chem 116:1707-10).

When the aforementioned linkers are used, the 1,6-elimination step still generates a highly reactive aromatic intermediate. Even if the aromatic moiety remains permanently attached to the polymeric carrier, side reactions with potentially toxic by-products or immunogenic effects may result. Thus, it is advantageous to generate linker technologies for forming polymeric prodrugs of amine-containing active agents using aliphatic prodrug linkers that are not enzyme-dependent and do not generate reactive aromatic intermediates during cleavage. One such example uses PEG5000-maleic anhydride for the reversible modification of amino groups in tissue-type plasminogen activator and urokinase (see, e.g. (1987) Garman et al. FEBS Lett 223(2):361-65). Regeneration of functional enzyme from PEG-uPA conjugate upon incubation at pH 7.4 buffer by cleavage of the maleamic acid linkage follows first order kinetics with a half-life of roughly 6 hours. A disadvantage of the maleamic acid linkage is the lack of stability of the conjugate at lower pH values.

A further approach comprises a PEG cascade prodrug system based on N,N-bis-(2-hydroxyethyl)glycine amide (bicine) linker (see e.g. (2004) J Med Chem 47:726-34). In this system, two PEG carrier molecules are linked via temporary bonds to a bicine molecule coupled to an amino group of the drug molecule. The first steps in prodrug activation involves the enzymatic cleavage of the first temporary linkages connecting both PEG carrier molecules with the hydroxy groups of the bicine activating group. Different linkages between PEG and bicine result in different prodrug activation kinetics. The second step in prodrug activation involves the cleavage of the second temporary linkage connecting the bicine activating group to the amino group of the drug molecule. A disadvantage of this system is the slow hydrolysis rate of this second temporary bicine amide linkage, which results in the release of a bicine-modified prodrug intermediate that may show different pharmacokinetic, immunogenic, toxicity and pharmacodynamic properties as compared to the native parent drug molecule.

In particular embodiments, dipeptides are utilized for prodrug development for targeting or targeted transport as they are substrates for enzymes or biotransport systems. The non-enzymatic route for dipeptide prodrug formation, that is, the ability to undergo intramolecular cyclization to form the corresponding diketopiperazine (DKP) and release the active drug, is not well defined.

In some embodiments, dipeptides are attached to a drug moiety via ester bonds, as was described for dipeptide esters of the drug paracetamol (Gomes et al. (2005) Bio & Med Chem Lett). In this case, the cyclization reaction consists of a nucleophilic attack of the N-terminal amine of the peptide on the ester carbon atom to form a tetrahedral intermediate, which is followed by a proton transfer from the amine to the leaving group oxyanion with simultaneous formation of a peptide bond to give the cyclic DKP product and free drug. This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al. (Molecules 12 (2007) 2484-2506). Susceptibility of dipeptide-based prodrugs to peptidases may be addressed by incorporating at least one non-natural amino acid in the dipeptide motif. However, endogenous enzymes capable of cleaving ester bonds are not limited to peptidases, and the enzyme-dependence of such prodrug cleavage still gives rise to unpredictable in vivo performance.

In some embodiments, enzyme-dependence is intentionally engineered into DKP prodrugs, such as where dipeptide ester prodrugs are formylated at the amino terminus of the dipeptide, and enzymatic deformylation is used to initiate diketopiperazine formation and subsequent cleavage of the ester-dipeptide bond, followed by release of the drug molecule (see, e.g., U.S. Pat. No. 7,163,923). By way of further example, an octapeptide is attached by an ester linkage to the 4-hydroxyl group of vinblastine and undergoes ester bond cleavage by DKP formation after specific enzymatic removal of the N-terminal hexapeptide (see Brady et al. (2002) J Med Chem 45:4706-15).

The scope of the DKP formation reaction has also been extended to amide prodrugs. By way of example, U.S. Pat. No. 5,952,294 describes prodrug activation using diketopiperazine formation for dipeptidyl amide prodrugs of cytarabine. In this case, the temporary linkage is formed between the carbonyl of a dipeptide and the aromatic amino group of cytarabine. However, it is unlikely that a slow-release effect can be achieved for such conjugates as there is no carrier or other half-life extending moiety or functionality present.

Dipeptide prodrugs comprising bioactive peptides such as GLP-1 capable of releasing the peptide through diketopiperazine formation of the dipeptidic extension have also been described (see, e.g., WO 2009/099763). The bioactive peptide moiety may include an additional PEG chain on one of its amino acid side chain residues to achieve extended circulation of the bioactive peptide. However, this approach is associated with several significant disadvantages. First, the PEG chain has to be linked to the peptide without compromising its bioactivity, which can be difficult to achieve for many peptide-based bioactive agents. Second, as the pegylated peptide itself is bioactive, the dipeptidic promoiety has an effect on the peptide's bioactivity and may negatively affect its receptor binding properties.

Specific exemplary technologies that may be used with the compounds of the present invention include those developed by ProLynx (San Francisco, CA) and Ascendis Pharma (Palo Alto, CA). The ProLynx technology platform utilizes sets of novel linkers that are pre-programmed to cleave at different rates to allow the controlled, predictable and sustained release of small molecules and peptides from circulating semi-solid macromolecular conjugates. The technology allows for maintenance of desired steady-state serum levels of therapeutic agents for weeks to months.

The Ascendis technology platform combines the benefits of prodrug and sustained release technologies to enhance the properties of small molecules and peptides. While in circulation, proprietary prodrugs release the unmodified active parent therapeutic agent at predetermined rates governed by physiological pH and temperature conditions. Because the therapeutic agent is released in its unmodified form, it retains its original mechanism of action.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Other known modifications include deuteration to improve pharmacokinetics, pharmacodyanics and toxicity profiles. Due to the greater atomic mass of deuterium, cleavage of the carbon-deuterium bond requires more energy than the carbon-hydorgen bond. Because these stronger bonds are more dfificult to break, the rate of drug metabolism is slower as compared to non-deuterated forms, which allows for less frequent dosing and may further reduce toxicities. (Charles Schmidt, Nature Biotechnology, 2017, 35(6): 493-494; Harbeson, S. and Tung, R., Medchem News, 2014(2): 8-22).

Therapeutic and Prophylactic Uses

The present invention contemplates the use of the $A_{2A}R/A_{2B}R$ inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

In some embodiments, the diseases, disorders and/or conditions described herein are mediated, at least in part, by the adenosine $A_{2A}$ receptor ($A_{2A}R$). In some embodiments, the diseases, disorders and/or conditions described herein are mediated, at least in part, by the adenosine $A_{2B}$ receptor ($A_{2B}R$). In some embodiments, the diseases, disorders and/or conditions described herein are mediated, at least in part, by both $A_{2A}R$ and $A_{2B}R$.

In some embodiments, the $A_{2A}R/A_{2B}R$ inhibitors described herein are administered in an amount effective to reverse or stop the progression of $A_{2A}R$-mediated immunosuppression.

Oncology-related Disorders. As indicated elsewhere herein, in addition to its involvement in the generation of an immune-tolerant microenvironment suitable for tumor onset and progression, adenosine, through the engagement of receptors expressed on neoplastic cells, also regulates the growth and dissemination of the tumor mass by direct actions on cancer cell proliferation, apoptosis and metastasis. Adenosine can also promote cell proliferation via activation of the $A_{2A}$ and $A_{2B}$ receptors.

The pharmacological blockade of $A_{2A}$ receptors results in decreased cancer development and spread, through an enhancement of the antitumor actions of CD8+ T cells as well as via an inhibition of tumor neovascularization, growth and metastatic potential. Likewise, the pharmacological blockade of $A_{2B}$ receptors results in a delay of tumor growth and reduction of metastatic dissemination. See, e.g., Antonioli, L. et al., Expert Op on Ther Targets 18(9):973-77 (2014).

In accordance with the present invention, an $A_{2A}R/A_{2B}R$ inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an $A_{2A}R/A_{2B}R$ inhibitor and at least one additional therapeutic or diagnostic agent, examples of which are set forth elsewhere herein.

Immune-and Inflammatory-related Disorders. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the $A_{2A}R/A_{2B}R$ inhibitors described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The $A_{2A}R/A_{2B}R$ inhibitors of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The $A_{2A}R/A_{2B}R$ inhibitors can also be used to stimulate the immune system of patients suffering from iatrogenically-induced immune suppression, including those who have undergone bone marrow transplants, chemotherapy, or radiotherapy.

In particular embodiments of the present disclosure, the $A_{2A}R/A_{2B}R$ inhibitors are used to increase or enhance an immune response to an antigen by providing adjuvant activity. In a particular embodiment, at least one antigen or vaccine is administered to a subject in combination with at least one $A_{2A}R/A_{2B}R$ inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one $A_{2A}R/A_{2B}R$ inhibitor of the present invention.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of $A_{2A}R/A_{2B}R$ function may also play a role in immunologic tolerance and prevention of fetal rejection in utero.

In some embodiments, an $A_{2A}R/A_{2B}R$ inhibitor described herein can be combined with an immunosuppressive agent to reduce the number of immune effector cells.

Some of the aforementioned diseases, disorders and conditions for which an $A_{2A}R/A_{2B}R$ inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra) Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

Microbial-related Disorders. The present invention contemplates the use of the $A_{2A}R/A_{2B}R$ inhibitors described herein in the treatment and/or prevention of any viral, bacterial, fungal, parasitic or other infective disease, disorder or condition for which treatment with an $A_{2A}R/A_{2B}R$ inhibitor may be beneficial.

Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Further examples of such diseases and disorders include staphylococcal and streptococcal infections (e.g., *Staphylococcus aureus* and *streptococcus sanguinis*, respectively), *leishmania, toxoplasma, trichomonas*, giardia, *Candida albicans, Bacillus anthracis*, and *Pseudomonas aeruginosa*. In some embodiments, diseases or disorders include *Mycobacterium* infection (e.g., *Mycobacterium leprae* or *Mycobacterium tuberculosis*) or an infection caused by *Listeria monocytogenes* or Toxplasma *gondii*. Compounds of the invention can be used to treat sepsis, decrease or inhibit bacterial growth, and reduce or inhibit inflammatory cytokines.

Further embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. Frequently, anti-parasitic therapy is administered prophylactically (e.g., before a subject travels to an area with a high frequency of parasitic infection).

CNS-related and Neurological Disorders. Inhibition of $A_{2A}R/A_{2B}R$ may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Subjects suffering from multiple sclerosis (MS), a seriously debilitating autoimmune disease comprising multiple areas of inflammation and scarring of the myelin in the brain and spinal cord, may be particularly helped by the $A_{2A}R/A_{2B}R$ inhibitors described herein, as current treatments only alleviate symptoms or delay the progression of disability.

Similarly, the $A_{2A}R/A_{2B}R$ inhibitors may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Other Disorders. Embodiments of the present invention contemplate the administration of the $A_{2A}R/A_{2B}R$ inhibitors described herein to a subject for the treatment or prevention of any other disorder that may benefit from at least some level of $A_{2A}R/A_{2B}R$ inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

Pharmaceutical Compositions

The $A_{2A}R/A_{2B}R$ inhibitors of the present invention may be in the form of compositions suitable for administration to a subject. In general, such compositions are "pharmaceutical compositions" comprising an $A_{2A}R/A_{2B}R$ inhibitor(s) and one or more pharmaceutically acceptable or physiologically acceptable diluents, carriers or excipients. In certain embodiments, the $A_{2A}R/A_{2B}R$ inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of $A_{2A}R/A_{2B}R$ function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an $A_{2A}R/A_{2B}R$ inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an $A_{2A}R/A_{2B}R$ inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the $A_{2A}R/A_{2B}R$ inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the $A_{2A}R/A_{2B}R$ inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The $A_{2A}R/A_{2B}R$ inhibitors contemplated by the present invention may be in the form of any other suitable pharmaceutical composition (e.g., sprays for nasal or inhalation use) currently known or developed in the future.

Routes of Administration

The present invention contemplates the administration of $A_{2A}R/A_{2B}R$ inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the $A_{2A}R/A_{2B}R$ inhibitors disclosed herein over a defined period of time.

Particular embodiments of the present invention contemplate oral administration.

Combination Therapy

The present invention contemplates the use of $A_{2A}R/A_{2B}R$ inhibitors alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the $A_{2A}R/A_{2B}R$ inhibitors are administered or applied sequentially, e.g., where one agent is administered prior to one or more other agents. In other embodiments, the $A_{2A}R/A_{2B}R$ inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The $A_{2A}R/A_{2B}R$ inhibitors of the present invention may be used in combination with at least one other (active) agent in any manner appropriate under the circumstances. In one embodiment, treatment with the at least one active agent and at least one $A_{2A}R/A_{2B}R$ inhibitor of the present invention is maintained over a period of time. In another embodiment, treatment with the at least one active agent is reduced or discontinued (e.g., when the subject is stable), while treatment with an $A_{2A}R/A_{2B}R$ inhibitor of the present invention is maintained at a constant dosing regimen. In a further embodiment, treatment with the at least one active agent is reduced or discontinued (e.g., when the subject is stable), while treatment with an $A_{2A}R/A_{2B}R$ inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the $A_{2A}R/A_{2B}R$ inhibitor of the present invention is increased (e.g., higher dose, more frequent dosing or longer treatment regimen). In yet another embodiment, treatment with the at least one active agent is maintained and treatment with the $A_{2A}R/A_{2B}R$ inhibitor of the present invention is reduced or discontinued (e.g., lower dose, less frequent dosing or shorter treatment regimen). In yet another embodiment, treatment with the at least one active agent and treatment with the $A_{2A}R/A_{2B}R$ inhibitor of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an $A_{2A}R/A_{2B}R$ inhibitor and at least one additional therapeutic or diagnostic agent. In some embodiments, the additional therapeutic or diagnostic agent is radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, anti-CD40, anti-CD38, anti-ICOS, and 4-1BB ligand; dendritic cell antigen loading (in vitro or in vivo); anti-cancer vaccines such as dendritic cell cancer vaccines; cytokines/chemokines, such as, I, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); indoleamine 2,3-dioxygenase 1 (IDO1) inhibitors and immune-stimulatory oligonucleotides.

In certain embodiments, the present invention provides methods for tumor suppression of tumor growth comprising administration of an $A_{2A}R/A_{2B}R$ inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the $A_{2A}R/A_{2B}R$ inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and docetaxel; chlorambucil; gemcitabine; 6-thioguanine; mercaptopurine; methotrexate; platinum and platinum coordination complexes such as cisplatin, carboplatin and oxaliplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; anthracyclines; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises a chemotherapy regimen that includes one or more chemotherapeutic agents. In certain embodiments, combination therapy comprises administration of a hormone or related hormonal agent.

Additional treatment modalities that may be used in combination with an $A_{2A}R/A_{2B}R$ inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present invention contemplates the use of the compounds described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present invention contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

Immune Checkpoint Inhibitors. The present invention contemplates the use of the inhibitors of $A_{2A}R/A_{2B}R$ function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T-cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms.

In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of $A_{2A}R/A_{2B}R$ function described herein in combination with inhibitors of the aforementioned immune-checkpoint receptors and ligands, as well as yet-to-be-described immune-checkpoint receptors and ligands. Certain modulators of immune checkpoints are currently approved, and many others are in development. When it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. The next class of immune checkpoint inhibitors to receive regulatory approval were against PD-1 and its ligands PD-L1 and PD-L2. Approved anti-PD1 antibodies include nivolumab (OPDIVO; Bristol-Myers Squibb) and pembrolizumab (KEYTRUDA; Merck) for various cancers, including squamous cell carcinoma, classical Hodgkin lymphoma and urothelial carcinoma. Approved anti-PDL1 antibodies include avelumab (BAVENCIO, EMD Serono & Pfizer), atezolizumab (TECENTRIQ; Roche/Genentech), and durvalumab (IMFINZI; AstraZeneca) for certain cancers, including urothelial carcinoma. While there are no approved therapeutics targeting TIGIT or its ligands CD155 and CD112, those in development include BMS-986207 (Bristol-Myers Squibb), MTIG7192A/RG6058 (Roche/Genentech), and OMP-31M32 (OncoMed).

In one aspect of the present invention, the claimed $A_{2A}R/A_{2B}R$ inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), B7-H6, and B7-H7 (HHLA2). Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD3OLD, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LT13R, LIGHT, DcR3, HVEM, VEGI/TL1A, TRAMP/DR3, EDAR, EDA1, XEDAR, EDA2, TNFR1, Lymphotoxin a/TNF13, TNFR2, TNFa, LT13R, Lymphotoxin a 1132, FAS, FASL, RELT, DR6, TROY, NGFR.

In another aspect, the immuno-oncology agent is a cytokine that inhibits T cell activation (e.g., IL-6, IL-10, TGF-B, VEGF, and other immunosuppressive cytokines) or a cytokine that stimulates T cell activation, for stimulating an immune response.

In one aspect, T cell responses can be stimulated by a combination of the disclosed $A_{2A}R/A_{2B}R$ inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the $A_{2A}R/A_{2B}R$ inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13/169264; WO14/036357).

In another aspect, the disclosed $A_{2A}R/A_{2B}R$ inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, TECENTRIQ (atezolizumab; MPDL3280A; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an $A_{2A}R/A_{2B}R$ inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the $A_{2A}R/A_{2B}R$ inhibitors described herein include various supplements and herbs (e.g., garlic, policosanol, and guggul).

The present invention encompasses pharmaceutically acceptable salts, acids or derivatives of any of the above.

Immune-and Inflammatory-related Disorders. The present invention provides methods for treating and/or preventing immune-related diseases, disorders and conditions; and diseases, disorders and conditions having an inflammatory component; with an $A_{2A}R/A_{2B}R$ inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-10, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFa-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the $A_{2A}R/A_{2B}R$ inhibitors described herein include interferon-131a (AVONEX); interferon-131b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Microbial Diseases. The present invention provides methods for treating and/or preventing viral, bacterial, fungal and parasitic diseases, disorders and conditions, as well as disorders associated therewith, with an $A_{2A}R/A_{2B}R$ inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), dd1, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an $A_{2A}R/A_{2B}R$ inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, TRUVADA, valaciclovir, valganciclovir, vicriviroc, vidarabine, viramidine, and zalcitabine.

The present invention contemplates the use of the inhibitors of $A_{2A}R/A_{2B}R$ function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the $A_{2A}R/A_{2B}R$ inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of antibacterial agents that are appropriate for use in specific bacterial infections.

Embodiments of the present invention contemplate the use of the $A_{2A}R/A_{2B}R$ inhibitors described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The $A_{2A}R/A_{2B}R$ inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the $A_{2A}R/A_{2B}R$ inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the $A_{2A}R/A_{2B}R$ inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000.0 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired $A_{2A}R/A_{2B}R$ inhibitor is contained in a "unit dosage form". The phrase "unit dosage form" refers to physically discrete units, each unit containing a predetermined amount of the $A_{2A}R/A_{2B}R$ inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound described herein, and pharmaceutical compositions thereof. The kits are generally in the form of a physical structure housing various components, as described below, and may be utilized, for example, in practicing the methods described above.

A kit can include one or more of the compounds disclosed herein (provided in, e.g., a sterile container), which may be in the form of a pharmaceutical composition suitable for administration to a subject. The compounds described herein can be provided in a form that is ready for use (e.g., a tablet or capsule) or in a form requiring, for example, reconstitution or dilution (e.g., a powder) prior to administration. When the compounds described herein are in a form that needs to be reconstituted or diluted by a user, the kit may also include diluents (e.g., sterile water), buffers, pharmaceutically acceptable excipients, and the like, packaged with or separately from the compounds described herein. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

The literature is replete with assays and other experimental techniques that can serve as a basis for evaluation of the compounds described herein.

Examples

General Methods for Preparation of Compounds of the Claims

Those skilled in the art will recognize that there are a variety of methods available to prepare molecules represented in the claims. In general, useful methods for synthesizing compounds represented in the claims consist of four parts, which may be done in any order:

Connection of the a and b fragments (or formation of the a-b-c moiety via b ring cyclization), connection of the b and c fragments (or formation of the a-b-c moiety via b ring cyclization), and modification of the functional groups present in all fragments. Retrosynthetic disconnection of the compounds of the invention into fragments a-c useful for construction of the compounds is shown below:

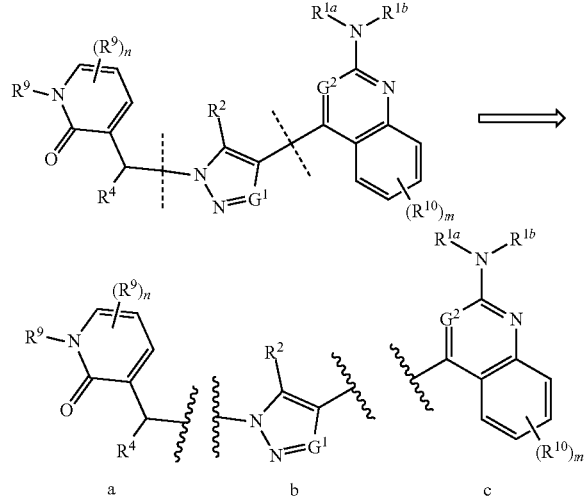

Several methods for the preparation of claimed compounds are exemplary (eq. 1-5). Equation 1 demonstrates one method of synthesizing an appropriately functionalized fragment c. In the case of eq. 1, readily available 2-aminobenzoic acids are converted to quinazolines via condensation with urea followed by treatment with phosphoryl chloride.

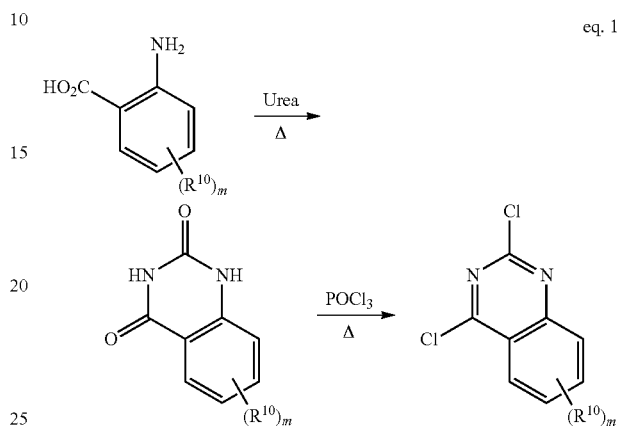

eq. 1

Alternatively, a wide variety of methods are known in the art for the formation of quinazoline and quinoline rings (see for instance Joule et al., "Heterocyclic Chemistry", Chapman & Hall, New York, or "Synthesis of Quinazolines" in http://www.organic-chemistry.org/synthesis/heterocycles/benzo-fused/quinazolines.shtm).

Equation two demonstrates one method of forming the bond between fragments b and c via a Suzuki reaction. In the case of eq. 2, Z may be chosen from an appropriate group such as Cl, Br, I, OTf, etc., and —B(OR)$_2$ is a boronic acid or ester and the coupling is mediated by a transition metal catalyst, preferably palladium with an appropriate ligand.

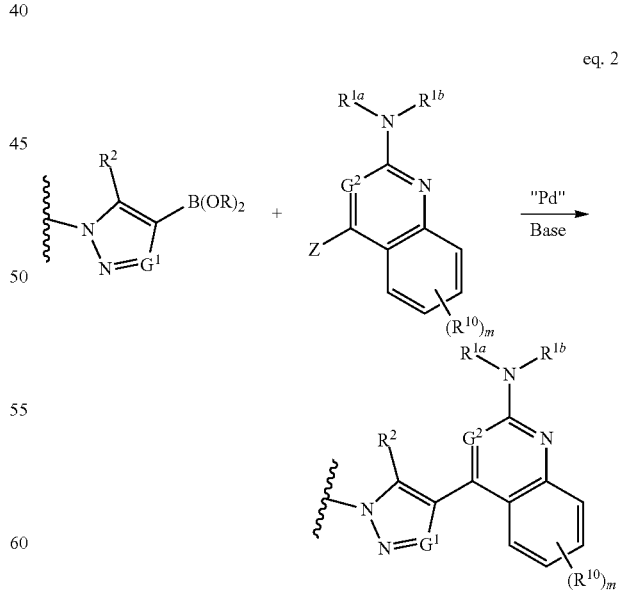

eq. 2

The coupling may be assisted by the use of an organic or inorganic base, and a wide variety of conditions are known in the art to facilitate the Suzuki coupling. The functionalization of the coupling partners may also be reversed as exemplified in eq. 3. Those skilled in the art will recognize that there are other possible combinations which will also result in the desired product. Formation of the bond between the b and c fragments may take place before or after formation of the connection between the a and b fragments, and the groups may be further modified before or after connection of the c and b fragments.

eq. 3

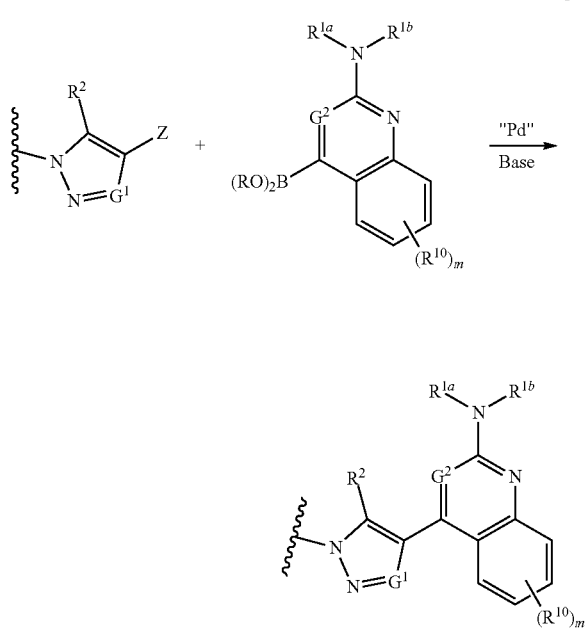

Alternatively, the b fragment may be formed by cycloaddition between the a and c fragments via an azide-alkyne Huisgen 1,3-dipolar cycloaddition (Equation four). In the case of eq. 4, the appropriately functionalized a and c fragments may be combined together in the cycloaddition reaction between an azide and an alkyne. The reaction may be facilitated via the use of a copper catalyst or other catalyst.

eq. 4

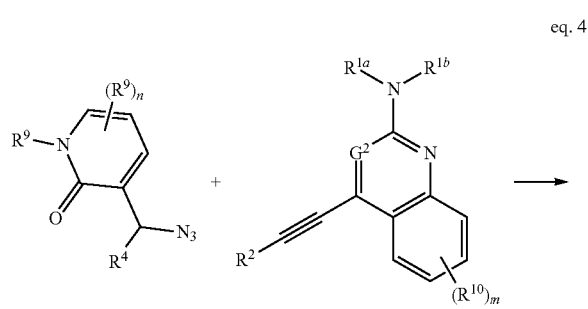

-continued

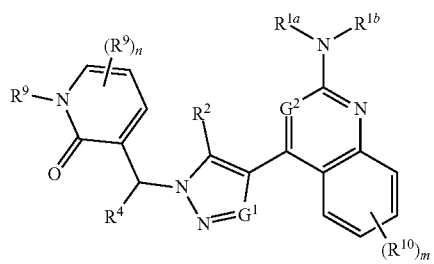

In the case where fragment b is a triazole, the ring may also be synthesized via a palladium mediated addition of sodium azide to alkenyl halides (Barluenga et. al., *Angew. Chem. Int. Ed.*, 2006, 45, 6893-6896), the Amberlyst-15 catalyzed addition of an azide to a nitroalkene (Zhang et. al., *Synthesis*, 2016, 48, 131-135), the I$_2$/TBPB mediated oxidative cycloaddition of N-tosylhydrozones with anilines (Cai et. al., *Org. Lett.*, 2014, 16, 5108-5111), and a host of other methods (see "Synthesis of 1,2,3-triazoles" in www-.organic-chemistry.org/synthesis/heterocycles/1,2,3-triazoles.shtm). One skilled in the art will understand that there are a wide variety of methods available to effect this transformation.

Equation five demonstrates one method of forming the bond between fragments a and b via alkylation. In the case of eq. 5, Z is an appropriate electrophile such as Cl, Br, I, OTf, etc. and the coupling is mediated via an organic or inorganic base. For the most efficient preparation of any particular compound of the invention, one skilled in the art will recognize that the timing and the order of connection of the fragments and modification of the functionality present in any of the fragments may vary in the preparation of any given compound.

eq. 5

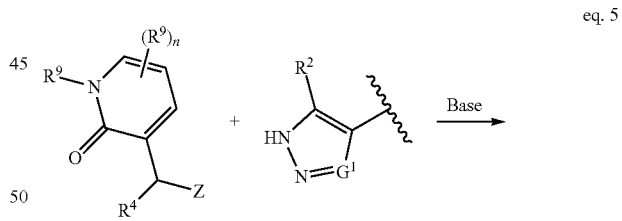

A variety of the methods described above have been used to prepare compounds of the invention, some of which are exemplified in the examples.-

Example 1: 3-{[4-(2-Amino-8-methoxy-4-quinazolinyl)-1H-1,2,3-triazol-1-yl]methyl}-1-isopropyl-1H-pyridin-2-one

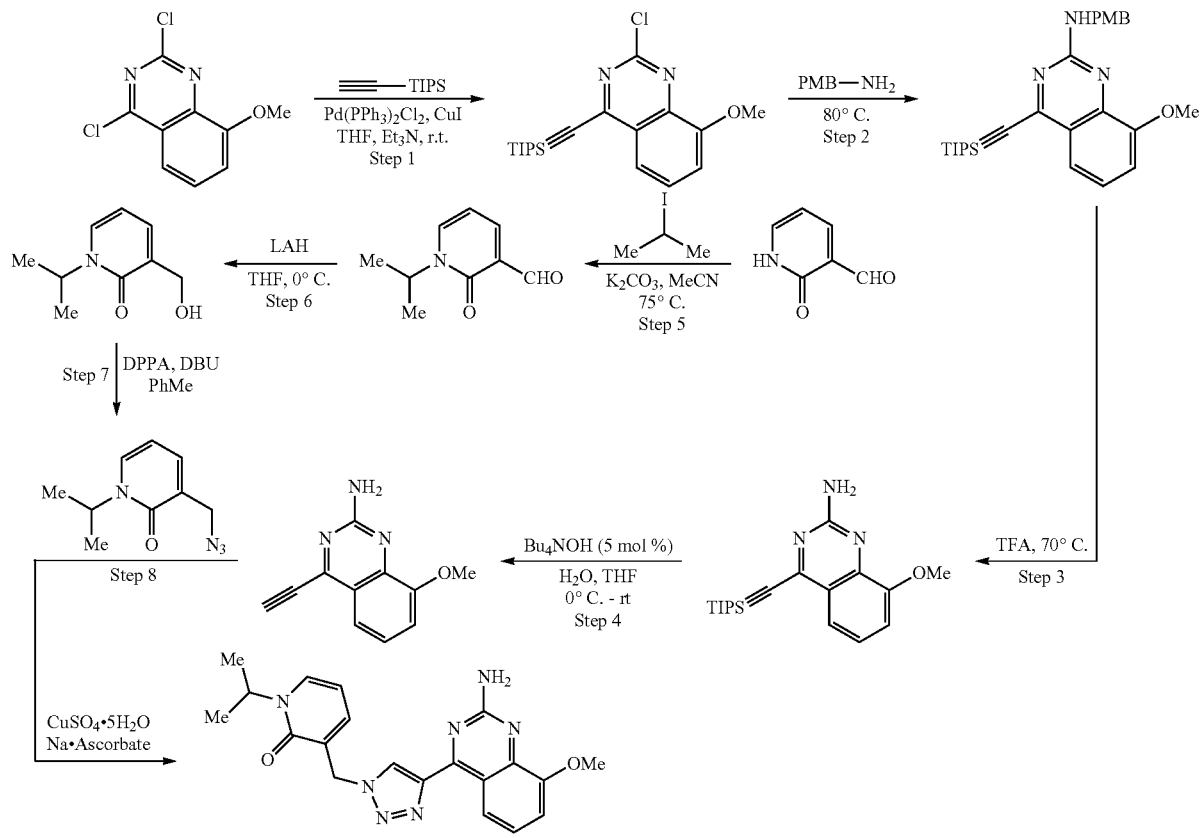

Step 1: Quinazoline dichloride (100 g, 437 mmol) was suspended in 880 mL dry THF. To this was added TIPS-acetylene (98 mL, 437 mmol), and Et₃N (183 mL, 1.3 mol). The resulting suspension was degassed by for 15 min. After degassing, the mixture was cooled to 0° C., followed by addition of CuI (2.5 g, 13 mmol) and Pd(PPh₃)₂Cl₂ (4.6 g, 6.6 mmol). The reaction was then stirred for 8 h, under nitrogen slowly raising to room temperature (Note: ice bath was not removed, instead allowed to melt and warm up to room temperature). The solid was filtered off and washed with 100 mL THF. The combined filtrate was washed with 1:1 NH₄Cl/NH₄OH (3×200 mL), dried over Na₂SO₄, concentrated and taken to next step without further purification.

Step 2: The crude product from step 1 was dissolved in a mixture of 100 mL THF and PMB-NH₂ (144 mL, 1.1 mol) and heated at 80° C. for 2.5 h. After cooling to room temperature, 600 mL EtOAc and 150 mL H₂O was added. The organic layer was separated and subsequently washed with 5% aqueous citric acid (2×400 mL) and 200 mL brine. The organic layer thus obtained was dried over Na₂SO₄, concentrated and taken to next step without further purification.

Step 3: The crude material from step 2 was suspended in 335 mL of TFA and heated to reflux for 12 h. Approximately 250 mL of TFA was distilled off first, followed by co-distillation with CH₂Cl₂ (2×300 mL). After cooling to room temperature, 1 L of CH₂Cl₂ and 1 L saturated NaHCO₃ was added and stirred for 1 h. The organic layer was separated, stirred with 50 g activated charcoal for 1 h and filtered through a pad of celite. Solvent was reduced to 300 mL and dropwise added 2.7 L heptane. A fine precipitate was obtained, which was filtered to obtain 128 g of the product. A second crop from the mother liquor gave additional 12 g of product. The total product 140 g thus obtained contained some unknown impurity (probably PMB-polymer). (Note: the precipitation is done with 10% CH₂Cl₂/heptane. For e.g., dissolve 1 g of crude in 2 mL of CH₂Cl₂ and adjust to 10% by adding heptane).

Step 4: The crude product from step 3 (140 g, 394.4 mmol) was dissolved in 790 mL THF. To this was added 20 mL H₂O and cooled to 0° C. A 1.0 M aqueous solution of Bu₄NOH (19.7 mL, 19.7 mmol) was added at 0° C. The ice bath was removed and stirred for 30 min at rt. To the reaction was added 20 mL saturated NH₄Cl and 8.0 L H₂O and stirred for additional 45 min. The precipitate thus formed was filtered, washed with 500 mL H₂O and dried. The crude material was triturated with 50% CH₂Cl₂/hexanes (790 mL) to obtain the pure product 50.4 g (58% over 4-steps), purity 99%.

Step 5: 2-hydroxynicotinaldehyde (1.89 g, 15.4 mmol, 1 equiv.) was dissolved in MeCN (45 mL), K₂CO₃ (4.3 g, 30.8 mmol, 2 equiv.) and 2-iodopropane (2.3 mL, 23.1 mmol, 1.5 equiv.) were added. The resulting mixture was heated to 75° C. until the starting material was consumed as determined by LC-MS. The reaction mixture was cooled to room temperature, filtered through Celite®, and concentrated. The crude residue was used without further purification.

Step 6: A solution of aldehyde (1.05 g, 6.4 mmol, 1 equiv.) in THF (30 mL) was cooled in an ice-water bath, and LAH (2M in THF, 3.2 mL, 6.4 mmol, 1 equiv.) was added. After 15 minutes, the reaction was quenched by addition of 0.24 mL H$_2$O, followed by 0.24 mL 10% NaOH. The reaction mixture stirred for 5 minutes, and 0.72 mL H$_2$O was added. Na$_2$SO$_4$ was added, and the reaction mixture was filtered and concentrated. The crude residue was used without further purification.

Step 7: To a solution of alcohol (1.03 g, 6.2 mmol, 1 equiv.) in toluene (8 mL) was added DPPA (1.6 mL, 7.4 mmol, 1.2 equiv.) and DBU (1.1 mL, 7.4 mmol, 1.2 equiv.). The reaction mixture stirred overnight and was purified directly by flash chromatography on SiO$_2$ to give the azide as an orange oil.

Step 8: A mixture of the azide from step 7 (96 mg, 0.5 mmol, 2 equiv.), quinazoline alkyne from step 4 (50 mg, 0.25 mmol), copper(II) sulfate pentahydrate (3.3 mg, 0.0125 mmol), and sodium ascorbate (10 mg, 0.050 mmol), in 2:1 t-BuOH/H$_2$O (1.2 mL) was stirred at 60° C. for 1 hour. The mixture was concentrated onto silica gel and purified by silica gel chromatography (0 to 5% MeOH in CH$_2$Cl$_2$) to afford the title compound as a tan solid (65 mg, 66% yield). $^1$H NMR (400 MHz, DMSO-d6) δ 8.71 (d, J=2.0 Hz, 1H), 8.65-8.58 (m, 1H), 7.87-7.79 (m, 1H), 7.47 (d, J=6.7 Hz, 1H), 7.23-7.11 (m, 2H), 6.88 (s, 2H), 6.42-6.29 (m, 1H), 5.53 (s, 2H), 5.16-5.01 (m, 1H), 3.88 (d, J=1.9 Hz, 3H), 1.29 (dd, J=6.8, 1.9 Hz, 6H). ESI MS [M+H]$^+$ for C$_{20}$H$_{21}$N$_7$O$_2$, calcd 392.2, found 392.2.

Example 2: 3-{[4-(2-Amino-8-methoxy-4-quinazolinyl)-1H-1,2,3-triazol-1-yl]methyl}-1-methyl-1H-pyridin-2-one

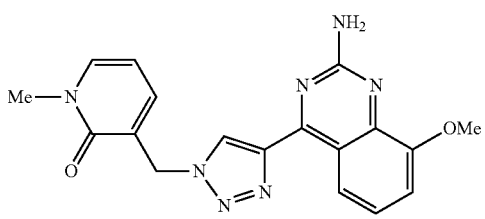 [SMILES: COc1cccc2c(-c3cn(Cc4cccn(C)c4=O)nn3)nc(N)nc12]

The title compound was synthesized in similar fashion to Example 1 from the corresponding azide and alkyne derivatives to afford 41 mg of a yellow solid. $^1$H NMR (400 MHz, DMSO-d6) δ 8.70 (d, J=1.2 Hz, 1H), 8.63 (ddd, J=6.0, 3.8, 1.1 Hz, 1H), 7.79 (dt, J=6.8, 1.5 Hz, 1H), 7.57 (dd, J=7.0, 2.0 Hz, 1H), 7.20-7.11 (m, 2H), 6.88 (s, 2H), 6.29 (td, J=6.8, 1.1 Hz, 1H), 5.52 (s, 2H), 3.88 (d, J=1.0 Hz, 3H), 3.47 (d, J=1.1 Hz, 3H). ESI MS [M+H]$^+$ for C$_{18}$H$_{17}$N$_7$O$_2$, calcd 364.2, found 364.1.

Example 3: 3-{[4-(2-Amino-8-methoxy-4-quinazolinyl)-1H-1,2,3-triazol-1-yl]methyl}-1-ehtyl-1H-pyridin-2-one

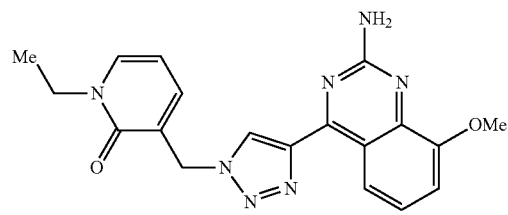 [SMILES: CCn1cccc(Cn2cc(-c3nc(N)nc4c(OC)cccc34)nn2)c1=O]

The title compound was synthesized in similar fashion to Example 1 from the corresponding azide and alkyne derivatives to afford 65 mg of a yellow solid. $^1$H NMR (400 MHz, CDCl$_3$) δ 8.81 (dd, J=8.6, 1.2 Hz, 1H), 8.67 (d, J=2.8 Hz, 1H), 7.44 (dd, J=6.8, 2.0 Hz, 1H), 7.33 (dd, J=6.8, 2.2 Hz, 1H), 7.26 (ddd, J=5.3, 2.4, 1.0 Hz, 1H), 7.10 (dd, J=7.8, 1.2 Hz, 1H), 6.21 (t, J=6.8 Hz, 1H), 5.56 (s, 2H), 5.25 (s, 2H), 4.12-3.97 (m, 5H), 1.47-1.32 (m, 3H). ESI MS [M+H]$^+$ for C$_{19}$H$_{19}$N$_7$O$_2$, calcd 378.2, found 378.2.

Example 4: 3-{[4-(2-Amino-8-methoxy-4-quinazolinyl)-1H-1,2,3-triazol-1-yl]methyl}-1-(cyclopropylmethyl)-1H-pyridin-2-one

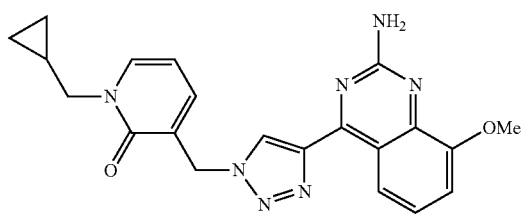 [SMILES: COc1cccc2c(-c3cn(Cc4cccn(CC5CC5)c4=O)nn3)nc(N)nc12]

The title compound was synthesized in similar fashion to Example 1 from the corresponding azide and alkyne derivatives to afford 64 mg of a yellow solid. $^1$H NMR (400 MHz, DMSO-d$_6$) δ 8.71 (d, J=1.4 Hz, 1H), 8.61 (ddd, J=5.4, 3.9, 1.4 Hz, 1H), 7.89-7.77 (m, 1H), 7.52 (d, J=7.0 Hz, 1H), 7.20-7.12 (m, 2H), 6.87 (s, 2H), 6.30 (td, J=6.8, 1.3 Hz, 1H), 5.53 (s, 2H), 3.88 (d, J=1.4 Hz, 3H), 3.77 (d, J=7.1 Hz, 2H), 1.22 (d, J=14.8 Hz, 1H), 0.46 (d, J=7.8 Hz, 2H), 0.37 (d, J=4.9 Hz, 2H). ESI MS [M+H]$^+$ for C$_{21}$H$_{21}$N$_7$O$_2$, calcd 404.2, found 404.2.

Example 5: 3-{[4-(2-Amino-8-methoxy-4-quinazolinyl)-1H-1,2,3-triazol-1-yl]methyl}-1-(2-hydroxy-2-methylpropyl)-1H-pyridin-2-one

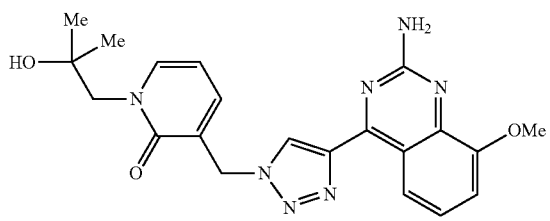 [SMILES: COc1cccc2c(-c3cn(Cc4cccn(CC(C)(C)O)c4=O)nn3)nc(N)nc12]

The title compound was synthesized in similar fashion to Example 1 from the corresponding azide and alkyne derivatives to afford 33 mg of a yellow solid. $^1$H NMR (400 MHz, DMSO-$d_6$) δ 8.72-8.66 (m, 1H), 8.59 (dd, J=5.4, 4.4 Hz, 1H), 7.67 (dd, J=6.8, 2.4 Hz, 1H), 7.54 (d, J=6.7 Hz, 1H), 7.22-7.10 (m, 2H), 6.86 (s, 2H), 6.28 (td, J=6.7, 2.2 Hz, 1H), 5.52 (s, 2H), 4.81-4.72 (m, 1H), 3.93 (d, J=2.4 Hz, 2H), 3.87 (s, 3H), 1.05 (d, J=2.4 Hz, 6H). ESI MS [M+H]$^+$ for $C_{21}H_{23}N_7O_3$, calcd 422.2, found 422.2.

Example 6: 3-{[4-(2-Amino-8-methoxy-4-quinazolinyl)-1H-1,2,3-triazol-1-yl]methyl}-1-(2-methoxy-1-methylethyl)-1H-pyridin-2-one

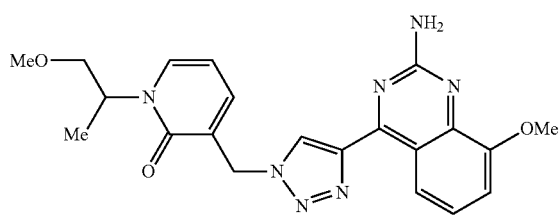 [SMILES: COCC(C)n1cccc(Cn2cc(-c3nc(N)nc4c(OC)cccc34)nn2)c1=O]

The title compound was synthesized in similar fashion to Example 1 from the corresponding azide and alkyne derivatives to afford 25 mg of a yellow solid. $^1$H NMR (400 MHz, DMSO-$d_6$) δ 8.72 (d, J=1.9 Hz, 1H), 8.63 (dt, J=5.8, 2.1 Hz, 1H), 7.78 (dd, J=7.0, 2.1 Hz, 1H), 7.51-7.41 (m, 1H), 7.24-7.11 (m, 2H), 6.88 (s, 2H), 6.33 (t, J=6.9 Hz, 1H), 5.53 (s, 2H), 5.24-5.07 (m, 1H), 3.89 (d, J=2.1 Hz, 3H), 3.64 (dd, J=10.5, 7.9 Hz, 1H), 3.49 (dd, J=10.5, 4.6 Hz, 1H), 3.20 (d, J=1.9 Hz, 3H), 1.32-1.23 (m, 3H). ESI MS [M+H]$^+$ for $C_{21}H_{23}N_7O_3$, calcd 422.2, found 422.2.

Example 7: 3-{[4-(2-Amino-8-methoxy-4-quinazolinyl)-1H-1,2,3-triazol-1-yl]methyl}-1-(2-hydroxy-1,2-dimethylpropyl)-1H-pyridin-2-one

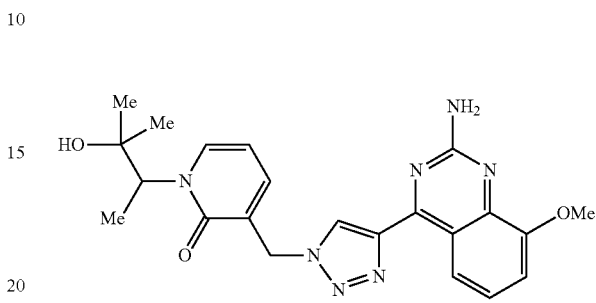

The title compound was synthesized in similar fashion to Example 1 from the corresponding azide and alkyne derivatives to afford 56 mg of a yellow solid. $^1$H NMR (400 MHz, DMSO-$d_6$) δ 8.70 (d, J=1.2 Hz, 1H), 8.64-8.54 (m, 1H), 7.85-7.73 (m, 1H), 7.48 (d, J=6.8 Hz, 1H), 7.22-7.11 (m, 2H), 6.86 (s, 2H), 6.31 (t, J=6.9 Hz, 1H), 5.52 (s, 2H), 5.02 (s, 1H), 4.85 (s, 1H), 3.88 (d, J=1.1 Hz, 3H), 1.30 (d, J=7.1 Hz, 3H), 1.20 (s, 3H), 0.85 (s, 3H). ESI MS [M+H]$^+$ for $C_{22}H_{25}N_7O_3$, calcd 436.2, found 436.2.

Example 8: 3-{[4-(2-Amino-8-methoxy-4-quinazolinyl)-1H-1,2,3-triazol-1-yl]methyl}-1-cyclopropyl-1H-pyridin-2-one

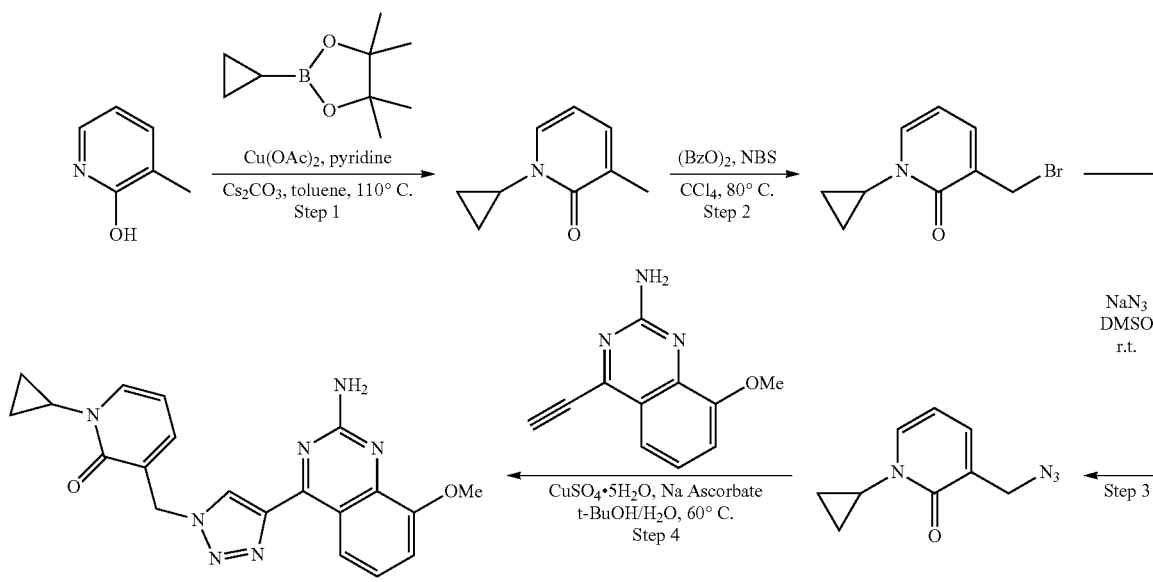

Step 1: A mixture of 2-hydroxy-3-methylpyridine (2.18 g, 20.0 mmol), copper(II) acetate (3.63 g, 20.0 mmol), pyridine (4.85 mL, 60.0 mmol), cyclopropylboronic acid pinacol ester (6.72 g, 40.0 mmol), cesium carbonate (3.86 g, 10.0 mmol), and toluene (40 mL) was stirred under air at 110° C. for 2 days. The mixture was cooled and EtOAc (100 mL)/water (100 mL) were added. The mixture was filtered to remove any solids, washing the filter cake with EtOAc/water. The resultant biphasic mixture was extracted with EtOAc (3×100 mL). The combined organic phases were dried over $Na_2SO_4$, concentrated, and purified by silica gel chromatography (50 to 100% EtOAc in hexanes) to afford the desired product as a yellow oil (1.93 g; 65%).

Step 2: A degassed mixture of the product from step 1 (1.93 g, 12.9 mmol), benzoyl peroxide (418 mg, 1.29 mmol, 75% in water), NBS (2.53 g, 14.2 mmol), and carbon tetrachloride (250 mL) was stirred at 80° C. for 1.5 hours. The mixture was concentrated and purified by silica gel chromatography (50 to 100% EtOAc in hexanes) to afford the desired product as a 1:1 mixture with succinimide. Yellow oil (1.87 g; 64% (corrected for succinimide)).

Step 3: A mixture of the product from step 2 (1.14 g, 5.00 mmol (corrected for succinimide)), sodium azide (360 mg, 6.00 mmol), and DMSO (10 mL) was stirred at r.t. for 2 hours. EtOAc (100 mL) was added and the resulting mixture washed with water (4×100 mL). The organic phase was dried over $Na_2SO_4$, concentrated, and purified by silica gel chromatography (50 to 100% EtOAc in hexanes) to afford the desired product as a yellow oil (500 mg; 53%).

Step 4: A mixture of the product from step 3 (86 mg, 0.45 mmol), quinazoline alkyne (60 mg, 0.30 mmol), copper(II) sulfate pentahydrate (4 mg, 0.015 mmol), sodium ascorbate (12 mg, 0.060 mmol), and 2:1 t-BuOH/$H_2O$ (1.2 mL) was stirred at 60° C. for 1 hour. The mixture was concentrated onto silica gel and purified by silica gel chromatography (0 to 5% MeOH in $CH_2Cl_2$) to afford the desired product as a yellow solid (66 mg; 56%). $^1$H NMR (400 MHz, DMSO-$d_6$) δ 8.72 (s, 1H), 8.66-8.60 (m, 1H), 7.63 (d, J=7.0 Hz, 1H), 7.53 (d, J=6.9 Hz, 1H), 7.22-7.14 (m, 2H), 6.89 (s, 2H), 6.26 (t, J=6.9 Hz, 1H), 5.53 (s, 2H), 3.89 (s, 3H), 3.43-3.36 (m, 1H), 1.04-0.96 (m, 2H), 0.90-0.82 (m, 2H). ESI MS [M+H]$^+$ for $C_{20}H_{20}N_7O_2$, calcd 390.2, found 390.2.

Example 9: 3-{[4-(2-Amino-8-methoxy-4-quinazolinyl)-1H-1,2,3-triazol-1-yl]methyl}-1-(tetrahydro-2H-pyran-4-yl)-1H-pyridin-2-one

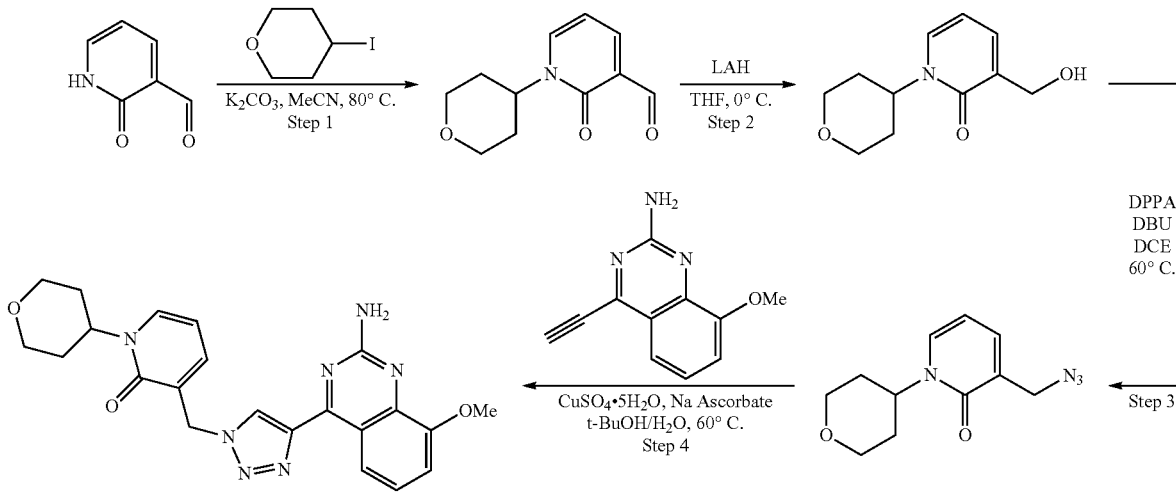

Step 1: The product was synthesized in a similar manner to Example 1, Step 5: yellow solid obtained (316 mg, 10%).

Step 2: To a solution of the product from step 1 (316 mg, 1.52 mmol) and THF (7.6 mL) at 0° C. was added LAH (762 μL, 1.52 mmol, 2M in THF) dropwise. The mixture was stirred at 0° C. for 15 minutes and 1M NaOH$_{(aq)}$ (380 μL) was added dropwise at 0° C. EtOAc (10 mL) and MgSO$_4$ was added. The mixture was filtered and concentrated to afford the desired product as a yellow oil (299 mg; 94%).

Step 3: To a solution of the product from step 2 (299 mg, 1.43 mmol), DPPA (339 μL, 1.57 mmol), and DCE (1.4 mL) at 0° C. was added DBU (235 μL, 1.57 mmol) dropwise. The mixture was stirred at 60° C. for 3 hours. The mixture was concentrated onto silica gel and purified by silica gel chromatography (0 to 100% EtOAc in hexanes) to afford the desired product as a white solid (24 mg; 7%).

Step 4: The title compound was synthesized in a similar manner to Example 1 from the corresponding azide and alkyne derivatives: yellow solid obtained (22 mg, 59%). $^1$H NMR (400 MHz, DMSO-d$_6$) δ 8.71 (s, 1H), 8.66-8.59 (m, 1H), 7.86 (d, J=7.0 Hz, 1H), 7.51 (d, J=7.0 Hz, 1H), 7.21-7.13 (m, 2H), 6.87 (s, 2H), 6.35 (t, J=6.9 Hz, 1H), 5.53 (s, 2H), 5.01-4.89 (m, 1H), 4.03-3.92 (m, 2H), 3.88 (s, 3H), 3.46 (t, J=11.9 Hz, 2H), 1.96-1.81 (m, 2H), 1.74-1.63 (m, 2H). ESI MS [M+H]$^+$ for C$_{22}$H$_{24}$N$_7$O$_3$, calcd 434.2, found 434.2.

Example 10: 3-{[4-(2-Amino-8-methoxy-4-quinazolinyl)-1H-1,2,3-triazol-1-yl]methyl}-1-(2-methoxyethyl)-1H-pyridin-2-one

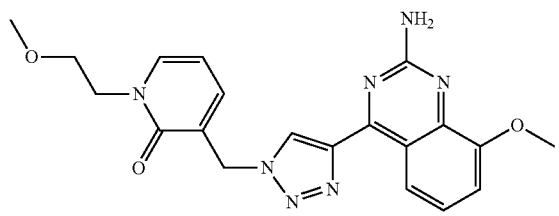

The title compound was synthesized similar to Example 1 from the corresponding azide and alkyne derivatives. $^1$H NMR (400 MHz, DMSO-d$_6$) δ 8.69 (s, 1H), 8.60 (m, 1H), 7.67 (d, J=6.8 Hz, 1H), 7.51 (d, J=6.9 Hz, 1H), 7.21-7.11 (m, 2H), 6.85 (s, 2H), 6.40-6.19 (m, 1H), 5.51 (s, 2H), 4.14-4.03 (m, 2H), 3.87 (s, 3H), 3.56 (m, 2H), 3.21 (s, 3H). ESI MS [M+H]$^+$ for C$_{20}$H$_{21}$N$_7$O$_3$, calcd 408.2, found 408.2.

Example 11: 3-{[4-(2-Amino-8-methoxy-4-quinazolinyl)-1H-1,2,3-triazol-1-yl]methyl}-1-[(tetrahydro-2H-pyran-4-yl)methyl]-1H-pyridin-2-one

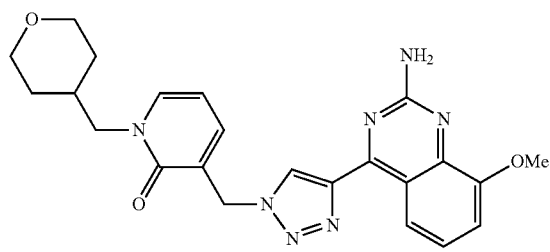 [SMILES: COc1cccc2c(-c3cn(Cc4cccn(CC5CCOCC5)c4=O)nn3)nc(N)nc12]

The title compound was synthesized similar to Example 1 from the corresponding azide and alkyne derivatives. $^1$H NMR (400 MHz, DMSO-d$_6$) δ 8.71 (s, 1H), 8.59 (s, 1H), 7.71 (d, J=6.8 Hz, 1H), 7.49 (d, J=6.9 Hz, 1H), 7.17-7.13 (m, 2H), 6.97-6.73 (m, 2H), 6.34-6.16 (m, 1H), 5.59-5.41 (m, 2H), 3.87 (s, 3H), 3.84-3.70 (m, 4H), 3.24-3.13 (m, 2H), 1.98 (s, 1H), 1.43-1.32 (m, 2H), 1.31-1.12 (m, 2H). ESI MS [M+H]$^+$ for C$_{23}$H$_{25}$N$_7$O$_3$, calcd 448.2, found 448.2.

Example 12: 3-{[4-(2-Amino-8-ethoxy-4-quinazolinyl)-1H-1,2,3-triazol-1-yl]methyl}-1-isopropyl-1H-pyridin-2-one

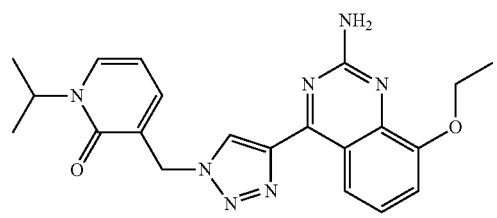 [SMILES: CCOc1cccc2c(-c3cn(Cc4cccn(C(C)C)c4=O)nn3)nc(N)nc12]

The title compound was prepared similar to Example 1 from the corresponding azide and alkyne derivatives. $^1$H NMR (400 MHz, DMSO-d$_6$) δ 8.71 (s, 1H), 8.65-8.58 (m, 1H), 7.83 (d, J=7.1 Hz, 1H), 7.48 (d, J=7.2 Hz, 1H), 7.19-7.12 (m, 2H), 6.88 (s, 2H), 6.35 (t, J=6.9 Hz, 1H), 5.53 (s, 2H), 5.09 (hept, J=6.6 Hz, 1H), 4.20-4.08 (m, 2H), 1.42 (t, J=7.0 Hz, 3H), 1.29 (d, J=6.9 Hz, 6H). ESI MS [M+H]$^+$ for C$_{21}$H$_{24}$N$_7$O$_2$, calcd 406.2, found 406.2.

Example 13: 3-{[4-(2-Amino-8-methyl-4-quinazolinyl)-1H-1,2,3-triazol-1-yl]methyl}-1-isopropyl-1H-pyridin-2-one

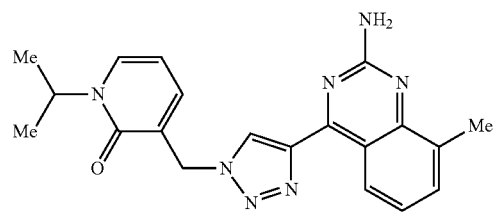 [SMILES: Cc1cccc2c(-c3cn(Cc4cccn(C(C)C)c4=O)nn3)nc(N)nc12]

The title compound was synthesized in similar fashion to Example 1 from the corresponding azide and alkyne derivatives to afford 80 mg of a yellow solid. $^1$H NMR (400 MHz, DMSO-d$_6$) δ 8.91 (d, J=8.5 Hz, 1H), 8.72 (d, J=0.8 Hz, 1H), 7.83 (dt, J=6.9, 1.7 Hz, 1H), 7.62-7.52 (m, 1H), 7.48 (dt, J=6.9, 1.7 Hz, 1H), 7.15 (ddd, J=8.3, 6.8, 1.2 Hz, 1H), 6.80 (s, 2H), 6.35 (td, J=6.8, 1.3 Hz, 1H), 5.53 (s, 2H), 5.16-5.03 (m, 1H), 2.49 (s, 3H), 1.39-1.18 (m, 6H). ESI MS [M+H]$^+$ for C$_{20}$H$_{21}$N$_7$O, calcd 376.2, found 376.2.

Example 14: 3-{[4-(2-Amino-8-fluoro-4-quinazolinyl)-1H-1,2,3-triazol-1-yl]methyl}-1-isopropyl-1H-pyridin-2-one

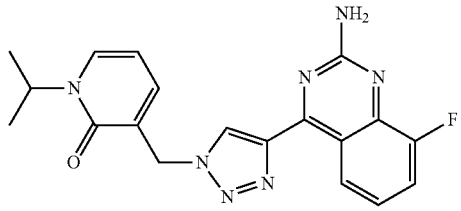 [SMILES: CC(C)n1cccc(Cn2cc(-c3nc(N)nc4c(F)cccc34)nn2)c1=O]

The title compound was synthesized similar to Example 1 from the corresponding azide and alkyne derivatives. $^1$H NMR (400 MHz, DMSO-$d_6$) δ 8.91 (d, J=8.5 Hz, 1H), 8.74 (s, 1H), 7.81 (d, J=7.0 Hz, 1H), 7.54 (m, 1H), 7.48 (d, J=6.9 Hz, 1H), 7.20 (m, 1H), 7.12 (s, 2H), 6.38-6.23 (m, 1H), 5.52 (s, 2H), 5.07 (h, J=5.7 Hz, 1H), 1.28 (s, 3H), 1.26 (s, 3H). ESI MS [M+H]$^+$ for $C_{19}H_{18}FN_7O$, calcd 380.2, found 380.1.

Example 15: 3-{[4-(2-Amino-8-chloro-4-quinazolinyl)-1H-1,2,3-triazol-1-yl]methyl}-1-isopropyl-1H-pyridin-2-one

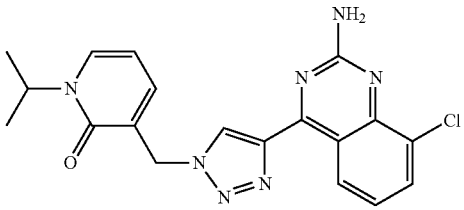 [SMILES: CC(C)n1cccc(Cn2cc(-c3nc(N)nc4c(Cl)cccc34)nn2)c1=O]

The title compound was synthesized similar to Example 1 from the corresponding azide and alkyne derivatives. $^1$H NMR (400 MHz, DMSO-$d_6$) δ 9.09 (d, J=8.5 Hz, 1H), 8.75 (d, J=1.5 Hz, 1H), 7.88 (d, J=7.5 Hz, 1H), 7.81 (d, J=7.0 Hz, 1H), 7.48 (d, J=6.9 Hz, 1H), 7.30-7.14 (m, 3H), 6.40-6.27 (m, 1H), 5.52 (s, 2H), 5.22-4.96 (m, 1H), 1.28 (s, 3H), 1.26 (s, 3H). ESI MS [M+H]$^+$ for $C_{19}H_{18}ClN_7O$, calcd 396.1, found 396.1.

Example 16: 3-{[4-(2-Amino-7-methoxy-4-quinazolinyl)-1H-1,2,3-triazol-1-yl]methyl}-1-isopropyl-1H-pyridin-2-one

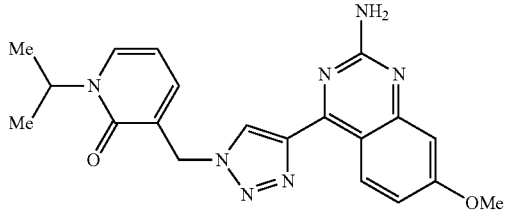 [SMILES: COc1ccc2c(-c3cn(Cc4cccn(C(C)C)c4=O)nn3)nc(N)nc2c1]

The title compound was synthesized in similar fashion to Example 1 from the corresponding azide and alkyne derivatives to afford 54 mg of a yellow solid. $^1$H NMR (400 MHz, DMSO-$d_6$) δ 8.99 (dd, J=9.3, 1.6 Hz, 1H), 8.69 (d, J=1.6 Hz, 1H), 7.92-7.71 (m, 1H), 7.47 (d, J=6.8 Hz, 1H), 6.90 (dt, J=9.2, 2.1 Hz, 1H), 6.83 (q, J=3.1, 2.2 Hz, 1H), 6.71 (s, 2H), 6.35 (td, J=6.9, 1.7 Hz, 1H), 5.52 (s, 2H), 5.23-4.95 (m, 1H), 3.88 (t, J=2.6 Hz, 3H), 1.29 (dd, J=6.8, 1.6 Hz, 6H). ESI MS [M+H]$^+$ for $C_{20}H_{21}N_7O_2$, calcd 392.2, found 392.2.

Example 17: 3-{[4-(2-Amino-7-fluoro-8-methoxy-4-quinazolinyl)-1H-1,2,3-triazol-1-yl]methyl}-1-isopropyl-1H-pyridin-2-one

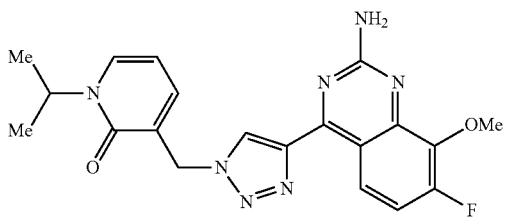 [SMILES: COc1c(F)ccc2c(-c3cn(Cc4cccn(C(C)C)c4=O)nn3)nc(N)nc12]

The title compound was synthesized in similar fashion to Example 1 from the corresponding azide and alkyne derivatives to afford 100 mg of an orange solid. $^1$H NMR (400 MHz, DMSO-$d_6$) δ 8.96-8.87 (m, 1H), 8.74 (d, J=1.3 Hz, 1H), 7.83 (dd, J=7.0, 2.0 Hz, 1H), 7.51-7.48 (m, 1H), 7.26-7.14 (m, 1H), 7.09 (s, 2H), 6.42-6.29 (m, 1H), 5.53 (s, 2H), 5.09 (p, J=6.8 Hz, 1H), 3.99 (d, J=1.4 Hz, 3H), 1.29 (dd, J=6.8, 1.3 Hz, 6H). ESI MS [M+H]$^+$ for $C_{20}H_{20}FN_7O_2$, calcd 410.2, found 410.1.

Example 18: 3-{[4-(2-Amino-6-fluoro-8-methoxy-4-quinazolinyl)-1H-1,2,3-triazol-1-yl]methyl}-1-isopropyl-1H-pyridin-2-one

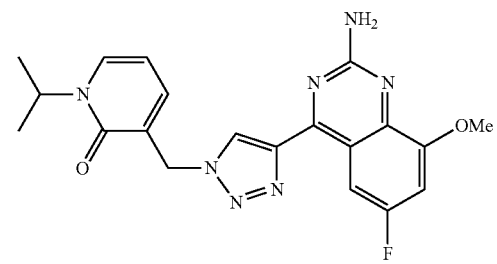 [SMILES: COc1cc(F)cc2c(-c3cn(Cc4cccn(C(C)C)c4=O)nn3)nc(N)nc12]

The title compound was synthesized in similar fashion to Example 1 from the corresponding azide and alkyne derivatives. $^1$H NMR (400 MHz, DMSO-$d_6$) 8.74 (s, 1H), 8.43 (d, J=8 Hz, 1H), 7.83 (d, J=8 Hz, 1H), 7.49 (d, J=4 Hz, 1H), 7.16 (d, J=8 Hz, 1H), 6.89 (s, 2H), 6.35 (s, 1H), 5.53 (s, 1H), 5.08 (s, 1H), 3.92 (s, 3H), 1.28 (d, J=8 Hz, 6H). ESI MS [M+H]$^+$ for $C_{20}H_{21}FN_7O_2$, calcd 410.2, found 410.3.

Example 19: 1-[(R)-1-(Tetrahydro-2H-pyran-4-yl)ethyl]-3-{[4-(2-amino-8-methoxy-4-quinazolinyl)-1H-1,2,3-triazol-1-yl]methyl}-1H-pyridin-2-one

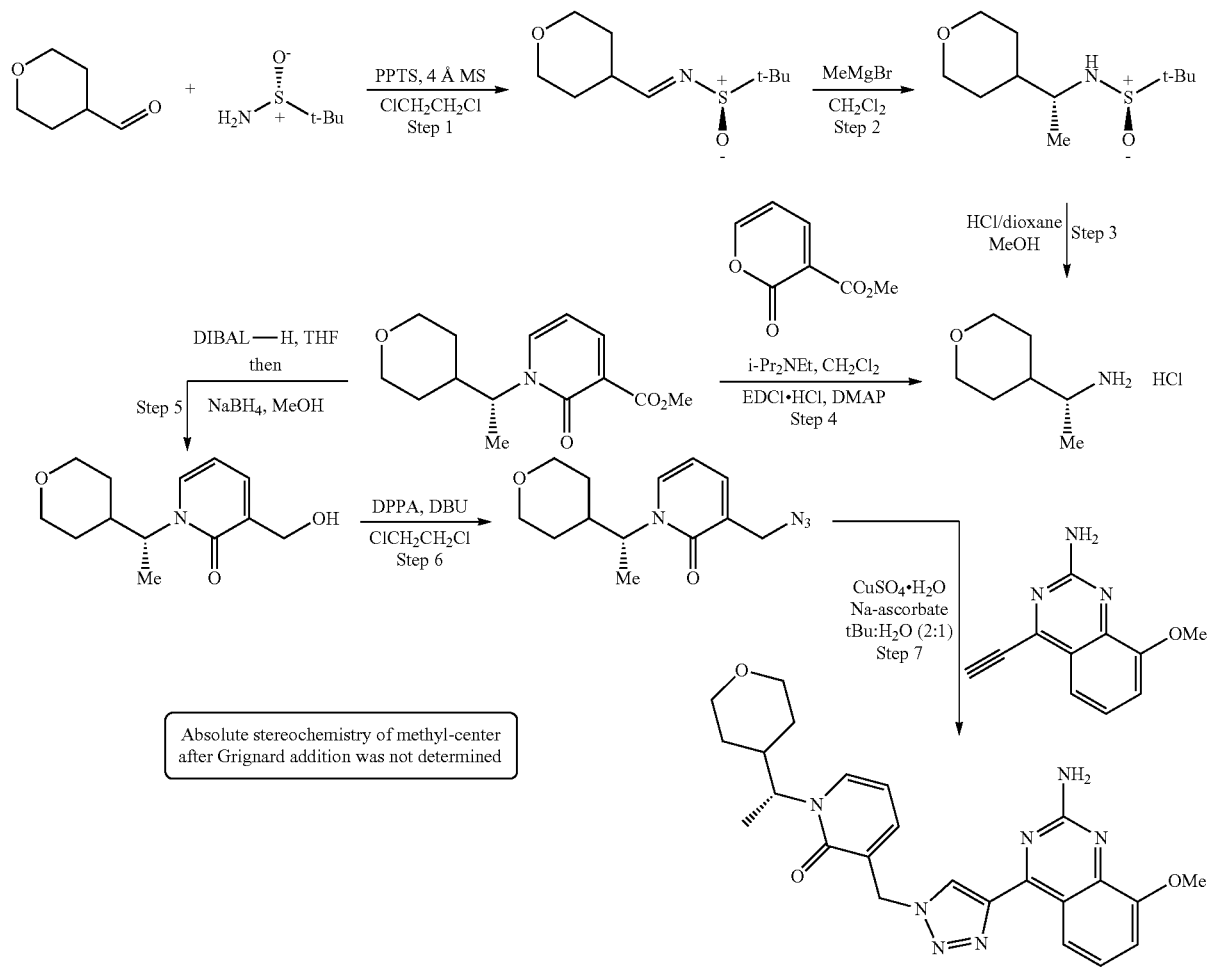

Absolute stereochemistry of methyl-center after Grignard addition was not determined Step 1: A round-bottom flask was charged with 18 g of 4 Å MS. To this flask was added tetrahydropyran-4-carbaldehyde (6.0 g, 52.3 mmol), (R)-(−)-t-butylsulfinamide (7.65 g, 63.2 mmol) and 75 mL dichloroethane and was stirred for 10 min under $N_2$ followed by addition of Pyridinium p-toluenesulfonate (661.3 mg, 2.63 mmol). The reaction mixture was stirred at room temperature for 16 h. The solid formed was filtered and filtrate was concentrated. The crude material was purified by silica gel chromatography to obtain the desired N-sulfinyl imine (7.5 g, 65%).

Step 2: To a solution of the N-sulfinyl imine (7.5 g, 34.4 mmol) obtained from step 1, in dichloromethane at 0° C. was added 3.0 M solution of MeMgBr in $Et_2O$ (22.9 mL, 68.8 mmol) dropwise. After complete addition, the reaction was stirred for 16 h under $N_2$ slowly warming to room temperature. Saturated $NH_4Cl$ (25 mL) was used to quench the reaction and the aqueous layer was extracted with $CH_2Cl_2$ (2×30 mL). The pooled organic layer was dried with $Na_2SO_4$, concentrated to obtain the desired α-methy-tetrahydropyran derivative, which was subjected to next step without further purification. Note: The absolute stereochemistry of α-methy-stereocenter after Grignard addition was not determined.

Step 3: The crude sulfonamide obtained from step 2 was dissolved in 50 mL MeOH and dropwise added a 40 mL solution of HCl (4.0 M in dioxane). The reaction was stirred at room temperature for 1 h. Solvent was evaporated and the solid was suspended in 200 mL MTBE and stirred at room temperature for 10 min. The white solid thus formed was filtered and washed quickly with 50 mL MTBE to obtain the desired product as a HCl salt (5.0 g, 89% for 2-steps). Note: The HCl salt is very hygroscopic thus, it was stored under $N_2$ in a sealed vial.

Step 4: In a round-bottom flask, methyl 2-pyrone-3-carboxylate (3.1 g, 20.0 mmol) was dissolved in 40 mL $CH_2C_2$. To this solution was added the HCl-salt of the amine obtained from step 3 (3.3 g, 20.0 mmol) and i-$Pr_2$NEt (3.7 mL, 22.0 mmol). After stirring the above reaction mixture for 8 h, EDCI·HCl (4.6 g, 24.0 mmol) and DMAP (1.2 g, 10 mmol) was added and stirred again for 16 h under $N_2$. Solvent was removed under reduced pressure and crude material was purified by silica gel chromatography to obtain the desired pyradinone (1.9 g, 35%).

Step 5: The pyradinone obtained from step 4 (1.5 g, 5.6 mmol) was dissolved in 11.0 mL dry THF. After cooling to −78° C., a 1.0 M solution of DIBAL-H in THE (12.3 mL, 12.3 mmol) was added dropwise. After addition, ice bath was removed and slowly raised to room temperature. After 1 h at room temperature, the reaction was cooled back to 0° C. and 3.0 mL of dry MeOH was added dropwise followed by addition of NaBH$_4$ (253.8 mg, 6.7 mmol). After 30 min, 20 mL of 10% citric acid solution was added to quench the reaction and stirred at room temperature for 30 min. The aqueous layer was extracted with EtOAc (2×30 mL). The pooled organic layer was dried with Na$_2$SO$_4$, concentrated and purified by silica gel chromatography to obtain the desired alcohol (626 g, 47%).

Step 6: The pyradone-azide derivative was synthesized from alcohol obtained from step 5 in similar fashion as performed in step 7 of Example 1.

Step 7: The title compound was synthesized similar to Example 1 from the corresponding azide and alkyne derivatives. $^1$H NMR (400 MHz, DMSO-d$_6$) δ 8.69 (d, J=2.1 Hz, 1H), 8.59 (t, J=5.5 Hz, 1H), 7.73 (d, J=6.9 Hz, 1H), 7.41 (d, J=6.6 Hz, 1H), 7.15 (dd, J=3.7, 1.9 Hz, 2H), 6.85 (s, 2H), 6.32 (t, J=6.8 Hz, 1H), 5.60-5.42 (m, 2H), 4.74 (s, 1H), 3.87 (m, 4H), 3.72 (m, 1H), 3.22 (m, 1H), 3.09 (m, 1H), 1.89 (m, 1H), 1.66 (m, 1H), 1.28 (d, J=7.0 Hz, 3H), 1.12 (m, 3H). ESI MS [M+H]$^+$ for C$_{24}$H$_{27}$N$_7$O$_3$, calcd 462.2, found 462.2.

Example 20: 1-[(S)-1-(Tetrahydro-2H-pyran-4-yl)ethyl]-3-{[4-(2-amino-8-methoxy-4-quinazolinyl)-1H-1,2,3-triazol-1-yl]methyl}-1H-pyridin-2-one

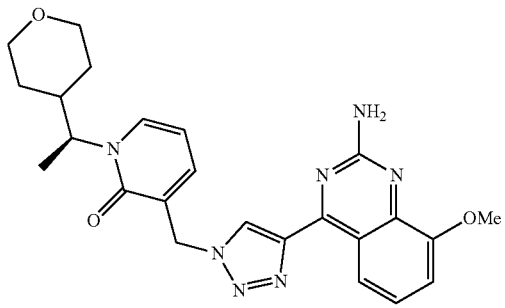 [SMILES: COc1cccc2c(-c3cn(Cc4cccn([C@@H](C)C5CCOCC5)c4=O)nn3)nc(N)nc12]

The title compound was synthesized similar to Example 19 starting from (S)-(−)-t-butylsulfinamide: $^1$H NMR (400 MHz, DMSO-d$_6$) δ 8.69 (d, J=2.1 Hz, 1H), 8.59 (t, J=5.5 Hz, 1H), 7.73 (d, J=6.9 Hz, 1H), 7.41 (d, J=6.6 Hz, 1H), 7.15 (dd, J=3.7, 1.9 Hz, 2H), 6.85 (s, 2H), 6.32 (t, J=6.8 Hz, 1H), 5.60-5.42 (m, 2H), 4.74 (s, 1H), 3.87 (m, 4H), 3.72 (m, 1H), 3.22 (m, 1H), 3.09 (m, 1H), 1.89 (m, 1H), 1.66 (m, 1H), 1.28 (d, J=7.0 Hz, 3H), 1.12 (m, 3H). ESI MS [M+H]$^+$ for C$_{24}$H$_{27}$N$_7$O$_3$, calcd 462.2, found 462.2.

Example 21: 3-{[4-(2-Amino-8-methoxy-4-quinazolinyl)-1H-1,2,3-triazol-1-yl]methyl}-1-(cis-4-hydroxycyclohexyl)-1H-pyridin-2-one

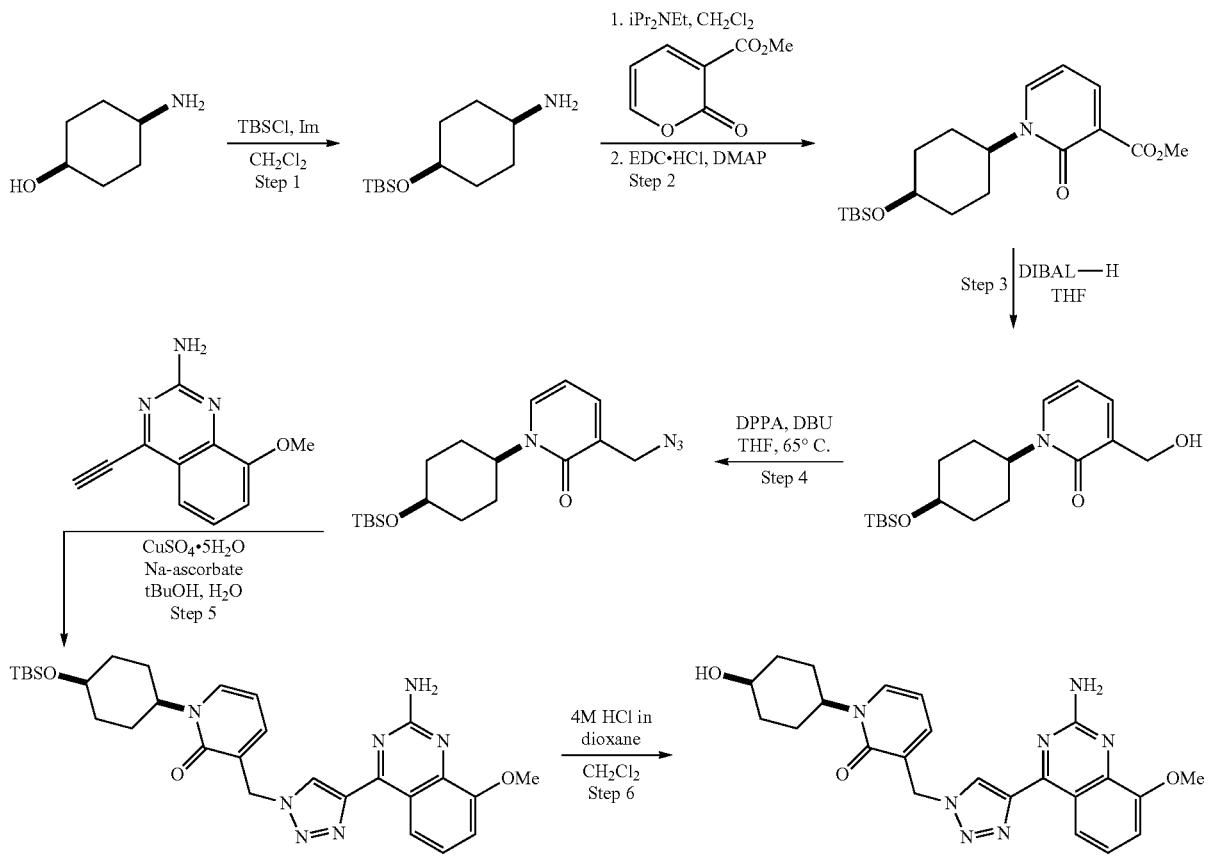

Step 1: In a 250 mL round bottom flask equipped with a magnetic stir bar was successively charged the amino alcohol (3.0 g, 19.78 mmol) and $CH_2Cl_2$ (37.3 mL). TBSCl (4.48 g, 29.67 mmol) followed by imidazole (2.43 g, 35.80 mmol) were added to the above solution. The solution was stirred at room temperature for 12 hours under a nitrogen atmosphere. Deionized water (50 mL) followed by brine (50 mL) were added to the above mixture. The layers were separated and aqueous layer extracted with $CH_2Cl_2$/MeOH (9:1) (150 mL). The combined organic layer was dried over $Na_2SO_4$, filtered and concentrated under reduced pressure. The resulting crude material was purified by flash chromatography over silica gel ($CH_2Cl_2$/MeOH gradient 100% to 70%). The desired product was obtained as a white solid (2.5 g).

Step 2: In a round-bottom flask, 2.23 g (10 mmol) of amine and $iPr_2NEt$ (1.74 mL, 10 mmol) were dissolved in 20 mL of $CH_2Cl_2$. To this solution was added 1.54 g (10 mmol) of pyrone derivative, stirred for 15 min at r.t, EDCI·HCl (2.3 g, 12 mmol) and DMAP (245 mg, 2.0 mmol) were added and the reaction mixture was stirred at r.t for an additional 20 h under $N_2$. After completion of the reaction, solvent was removed and the crude material was purified by flash chromatography over silica gel (ethyl acetate/hexane, gradient 0% to 60%). The desired product was obtained as a pale brown solid (1.03 g).

Step 3: To a solution of methyl carboxylate (1.037 g, 2.82 mmol) in THF (28 mL) at −78° C. was added DIBAL-H (6.2 mL, 6.2 mmol) dropwise over 5 mins. The solution was then stirred at the same temperature for 15 mins. The reaction mixture was warmed to 23° C. over 1 h and stirred at the same temperature for additional 1 h. The reaction mixture was quenched with 10% aqueous citric acid solution (30 mL). The layers are separated and the aqueous layer was extracted with $iPrOH/CHCl_3$ (1:2) (100 mL). The combined organic layer was dried over $Na_2SO_4$ and removed under reduced pressure. The crude material was purified by flash chromatography over silica gel (hexane/ethyl acetate gradient 0% to 100%). The desired alcohol was obtained as pale yellow solid (0.4 g).

Step 4: The desired azide was obtained as liq (0.2 g) following Example 19 procedure.

Step 5: The desired triazole was obtained as solid (0.14 g) following Example 1 from the corresponding azide and alkyne derivatives.

Step 6: To a solution of triazole (0.14 g, 0.25 mmol) in $CH_2Cl_2$ (0.64 mL) at 0° C. was added 4 (M) HCl in dioxane (0.25 mL, 1.1 mmol) dropwise. The solution was warmed to 23° C. over 15 min and stirred at the same temperature for 4 h. The solvent was evaporated and the resulted solid was washed with ethyl acetate to give the desired product as yellow solid (82 mg). $^1$H NMR (400 MHz, DMSO-$d_6$) 8.98 (s, 1H), 8.92 (s, 1H), 7.79 (d, J=8.0 Hz, 1H), 7.64 (d, J=8.0 Hz, 1H), 7.60 (d, J=8.0 Hz, 1H), 7.54 (t, J=8 Hz, 1H), 6.36 (t, J=8 Hz, 1H), 5.58 (s, 2H), 4.67 (t, J=12 Hz, 1H), 4.07 (s, 3H), 3.87 (s, 3H), 1.99-1.90 (m, 2H), 1.78 (d, J=8 Hz, 2 H), 1.58-1.46 (m, 4H). ESI MS $[M+H]^+$ for $C_{23}H_{26}N_7O_3$, calcd 448.2, found 448.3.

Example 22: 3-{[4-(2-Amino-8-methoxy-4-quinazolinyl)-1H-1,2,3-triazol-1-yl]methyl}-1-(trans-4-hydroxycyclohexyl)-1H-pyridin-2-one

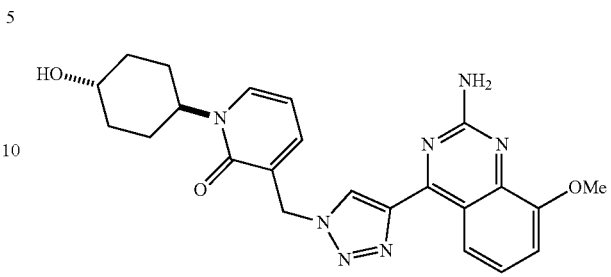

The title compound was prepared similar to Example 21 from the corresponding azide and alkyne derivatives. $^1$H NMR (400 MHz, DMSO-$d_6$) 8.70 (s, 1H), 8.62 (s, 1H), 7.79 (d, J=8 Hz, 1H), 7.49 (d, J=8 Hz, 1H), 7.16 (s, 2H), 6.87 (s, 2H), 6.34-6.29 (m, 1H), 5.51 (s, 2H), 4.69-4.63 (m, 2H), 3.89 (s, 3H), 3.47 (bs, 1H), 1.94-1.87 (m, 2H), 1.73-1.65 (m, 4 H), 1.35-1.25 (m, 2H). ESI MS $[M+H]^+$ for $C_{23}H_{26}N_7O_3$, calcd 448.2, found 448.4.

Example 23: 1-[(R)-2-Methoxy-1-methylethyl]-3-{[4-(2-amino-8-methoxy-4-quinazolinyl)-1H-1,2,3-triazol-1-yl]methyl}-1H-pyridin-2-one

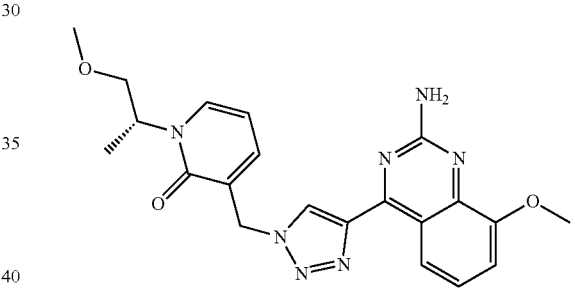

The title compound was prepared similar to Example 21 from the corresponding azide and alkyne derivatives. $^1$H NMR (400 MHz, DMSO-$d_6$) δ 8.71 (s, 1H), 8.65-8.59 (m, 1H), 7.78 (d, J=7.3 Hz, 1H), 7.47 (d, J=7.1 Hz, 1H), 7.20-7.13 (m, 2H), 6.88 (s, 2H), 6.33 (t, J=6.9 Hz, 1H), 5.53 (s, 2H), 5.22-5.10 (m, 1H), 3.88 (s, 3H), 3.64 (dd, J=10.4, 7.9 Hz, 1H), 3.49 (dd, J=10.5, 4.7 Hz, 1H), 3.20 (s, 3H), 1.27 (d, J=7.1 Hz, 3H). ESI MS $[M+H]^+$ for $C_{21}H_{24}N_7O_3$, calcd 422.2, found 422.2.

Example 24: 3-{[4-(2-Amino-8-methoxy-4-quinazolinyl)-1H-1,2,3-triazol-1-yl]methyl}-1-cyclopentyl-1H-pyridin-2-one

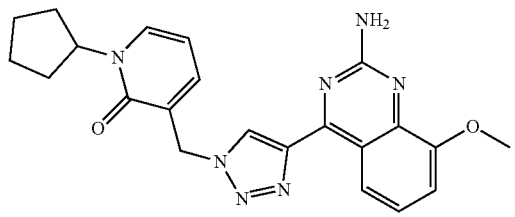 [SMILES: COc1cccc2c(-c3cn(Cc4cccn(C5CCCC5)c4=O)nn3)nc(N)nc12]

The title compound was prepared similar to Example 21 from the corresponding azide and alkyne derivatives. $^1$H NMR (400 MHz, DMSO-d$_6$) δ 8.97 (d, J=8.8 Hz, 1H), 8.93 (s, 1H), 7.81 (d, J=6.9 Hz, 1H), 7.70-7.47 (m, 3H), 6.42-6.30 (m, 1H), 5.59 (s, 2H), 5.20-5.04 (m, 1H), 4.06 (s, 3H), 2.09-1.91 (m, 2H), 1.91-1.73 (m, 2H), 1.73-1.53 (m, 4H). ESI MS [M+H]$^+$ for C$_{22}$H$_{24}$N$_7$O$_2$, calcd 418.2, found 418.2.

Example 25: 1-[(S)-2-Hydroxy-1,2-dimethylpropyl]-3-{[4-(2-amino-6-fluoro-8-methoxy-4-quinazolinyl)-1H-1,2,3-triazol-1-yl]methyl}-1H-pyridin-2-one

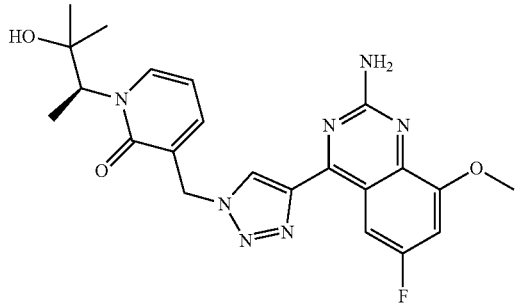 [SMILES: COc1cc(F)cc2c(-c3cn(Cc4cccn([C@@H](C)C(C)(C)O)c4=O)nn3)nc(N)nc12]

The title compound was prepared similar to Example 12 from the corresponding azide and alkyne derivatives. $^1$H NMR (400 MHz, DMSO-d$_6$) δ 8.88 (s, 1H), 8.64 (d, J=9.8 Hz, 1H), 7.82 (d, J=6.9 Hz, 1H), 7.57 (d, J=6.6 Hz, 2H), 7.54-7.46 (m, 1H), 6.38-6.27 (m, 1H), 5.58 (s, 2H), 5.04-4.99 (m, 1H), 4.03 (s, 3H), 1.30 (d, J=7.0 Hz, 3H), 1.20 (s, 3H), 0.84 (s, 3H). ESI MS [M+H]$^+$ for C$_{22}$H$_{25}$FN$_7$O$_3$, calcd 454.2, found 454.2.

Example 26: 1-[(S)-2-Hydroxy-1,2-dimethylpropyl]-3-{[4-(2-amino-8-methoxy-4-quinazolinyl)-1H-1,2,3-triazol-1-yl]methyl}-1H-pyridin-2-one

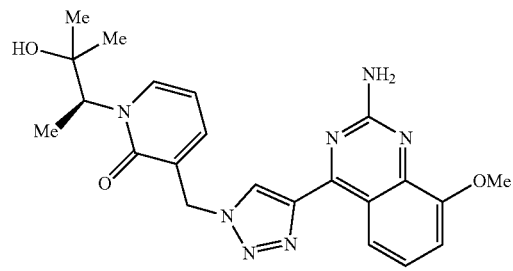 [SMILES: COc1cccc2c(-c3cn(Cc4cccn([C@@H](C)C(C)(C)O)c4=O)nn3)nc(N)nc12]

The title compound was synthesized in similar fashion to Example 21 from the corresponding azide and alkyne derivatives to afford 25 mg of a tan solid. $^1$H NMR (400 MHz, DMSO-d$_6$) δ 8.70 (d, J=1.2 Hz, 1H), 8.64-8.54 (m, 1H), 7.85-7.73 (m, 1H), 7.48 (d, J=6.8 Hz, 1H), 7.22-7.11 (m, 2H), 6.86 (s, 2H), 6.31 (t, J=6.9 Hz, 1H), 5.52 (s, 2H), 5.02 (s, 1H), 4.85 (s, 1H), 3.88 (d, J=1.1 Hz, 3H), 1.30 (d, J=7.1 Hz, 3H), 1.20 (s, 3H), 0.85 (s, 3H). ESI MS [M+H]$^+$ for C$_{22}$H$_{25}$N$_7$O$_3$, calcd 436.2, found 436.2.

Example 27: 1-[(R)-2-Hydroxy-1,2-dimethylpropyl]-3-{[4-(2-amino-8-methoxy-4-quinazolinyl)-1H-1,2,3-triazol-1-yl]methyl}-1H-pyridin-2-one

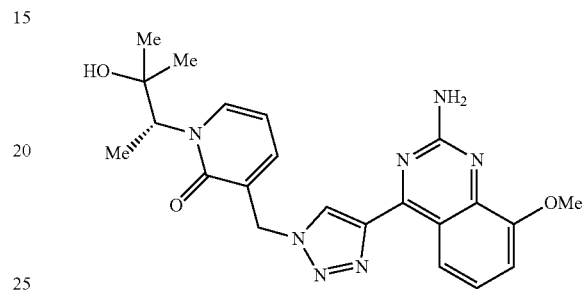

The title compound was synthesized in similar fashion to Example 21 from the corresponding azide and alkyne derivatives to afford 20 mg of a tan solid. $^1$H NMR (400 MHz, DMSO-d$_6$) δ 8.70 (d, J=1.2 Hz, 1H), 8.64-8.54 (m, 1H), 7.85-7.73 (m, 1H), 7.48 (d, J=6.8 Hz, 1H), 7.22-7.11 (m, 2H), 6.86 (s, 2H), 6.31 (t, J=6.9 Hz, 1H), 5.52 (s, 2H), 5.02 (s, 1H), 4.85 (s, 1H), 3.88 (d, J=1.1 Hz, 3H), 1.30 (d, J=7.1 Hz, 3H), 1.20 (s, 3H), 0.85 (s, 3H). ESI MS [M+H]$^+$ for C$_{22}$H$_{25}$N$_7$O$_3$, calcd 436.2, found 436.2.

Example 28: 1-[(S)-1-Cyclopropylethyl]-3-{[4-(2-amino-8-methoxy-4-quinazolinyl)-1H-1,2,3-triazol-1-yl]methyl}-1H-pyridin-2-one

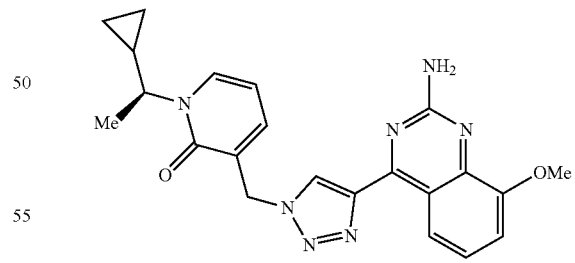

The title compound was synthesized in similar fashion to Example 21 from the corresponding azide and alkyne derivatives to afford 62 mg of an orange solid. $^1$H NMR (400 MHz, DMSO-d$_6$) δ 8.77-8.66 (m, 1H), 8.61 (s, 1H), 7.97 (d, J=6.8 Hz, 1H), 7.44 (d, J=6.7 Hz, 1H), 7.17 (t, J=3.1 Hz, 2H), 6.87 (s, 2H), 6.37 (d, J=7.2 Hz, 1H), 5.52 (s, 2H), 4.21 (d, J=9.8 Hz, 1H), 3.95-3.80 (m, 3H), 1.35 (d, J=6.6 Hz, 3H), 0.63 (s, 1H), 0.41 (d, J=6.5 Hz, 3H), 0.15 (s, 1H). ESI MS [M+H]$^+$ for C$_{22}$H$_{23}$N$_7$O$_2$, calcd 418.2, found 418.2.

Example 29: 1-[(R)-Tetrahydrofur-3-yl]-3-{[4-(2-amino-8-methoxy-4-quinazolinyl)-1H-1,2,3-triazol-1-yl]methyl}-1H-pyridin-2-one

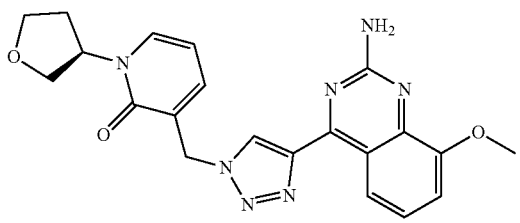 [SMILES: COc1cccc2c(-c3cn(Cc4cccn([C@@H]5CCOC5)c4=O)nn3)nc(N)nc12]

The title compound was prepared similar to Example 21 from the corresponding azide and alkyne derivatives. $^1$H NMR (400 MHz, DMSO-d$_6$) δ 8.71 (s, 1H), 8.65-8.58 (m, 1H), 7.66 (d, J=7.0 Hz, 1H), 7.53 (d, J=6.8 Hz, 1H), 7.19-7.13 (m, 2H), 6.88 (s, 2H), 6.37 (t, J=6.9 Hz, 1H), 5.53 (s, 2H), 5.45-5.38 (m, 1H), 4.09-4.00 (m, 1H), 3.88 (s, 3H), 3.85-3.80 (m, 2H), 3.78-3.69 (m, 1H), 2.48-2.39 (m, 1H), 2.00-1.89 (m, 1H). ESI MS [M+H]$^+$ for C$_{21}$H$_{22}$N$_7$O$_3$, calcd 420.2, found 420.2.

Example 30: 1-[(S)-2-Methoxy-1-methylethyl]-3-{[4-(2-amino-8-methoxy-4-quinazolinyl)-1H-1,2,3-triazol-1-yl]methyl}-1H-pyridin-2-one

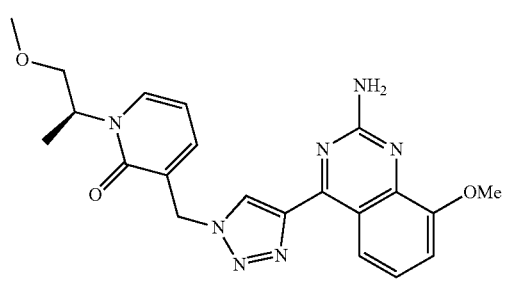 [SMILES: COC[C@H](C)n1cccc(Cn2cc(-c3nc(N)nc4c(OC)cccc34)nn2)c1=O]

The title compound was synthesized similar to Example 21 from the corresponding azide and alkyne derivatives. $^1$H NMR (400 MHz, DMSO-d$_6$) δ 8.70 (s, 1H), 8.60 (d, J=6.2 Hz, 1H), 7.82-7.71 (m, 1H), 7.49-7.37 (m, 1H), 7.16 (d, J=5.1 Hz, 2H), 6.87 (s, 2H), 6.31 (t, J=6.9 Hz, 1H), 5.51 (s, 2H), 5.14 (m, 1H), 3.87 (s, 3H), 3.67-3.54 (m, 1H), 3.47 (dd, J=10.5, 4.6 Hz, 1H), 3.18 (s, 3H), 1.24 (d, J=7.0 Hz, 3H). ESI MS [M+H]$^+$ for C$_{21}$H$_{23}$N$_7$O$_3$, calcd 422.2, found 422.2.

Example 31: 1-[(R)-1-(Tetrahydro-2H-pyran-4-yl)ethyl]-3-{[4-(2-amino-6-fluoro-8-methoxy-4-quinazolinyl)-1H-1,2,3-triazol-1-yl]methyl}-1H-pyridin-2-one

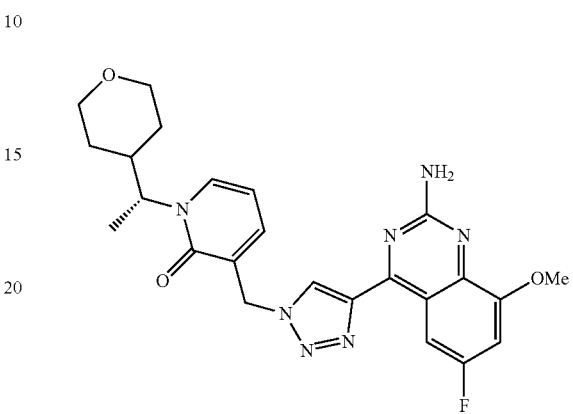

The title compound was synthesized similar to Example 19 from the corresponding azide and alkyne derivatives. $^1$H NMR (400 MHz, DMSO-d$_6$) δ 8.72 (s, 1H), 8.41 (d, J=8.0 Hz, 1H), 7.73 (d, J=6.8 Hz, 1H), 7.42 (d, J=5.7 Hz, 1H), 7.15 (d, J=8.0 Hz, 1H), 6.86 (s, 2H), 6.32 (s, 1H), 5.61-5.44 (m, 2H), 4.73 (m, 1H), 3.90 (s, 3H), 3.84 (m, 1H), 3.72 (d, J=11.3 Hz, 1H), 3.22 (t, J=11.7 Hz, 1H), 3.16-3.00 (m, 1H), 1.89 (m, 1H), 1.66 (d, J=13.0 Hz, 1H), 1.27 (d, J=5.5 Hz, 3H), 1.22 (m, 1H), 1.11-0.94 (m, 2H). ESI MS [M+H]$^+$ for C$_{24}$H$_{26}$N$_7$O$_3$, calcd 480.2, found 480.2.

Example 32: 1-[(S)-Tetrahydro-2H-pyran-3-yl]-3-{[4-(2-amino-8-methoxy-4-quinazolinyl)-1H-1,2,3-triazol-1-yl]methyl}-1H-pyridin-2-one The title compound was synthesized similar to Example 21 from the corresponding azide and alkyne derivatives. $^1$H NMR (400 MHz, DMSO-d$_6$) δ 8.76-8.67 (m, 1H), 8.60 (s, 1H), 7.88 (d, J=6.3 Hz, 1H), 7.49 (d, J=6.7 Hz, 1H), 7.15 (s, 2H), 6.86 (s, 2H), 6.41-6.19 (m, 1H), 5.51 (s, 2H), 4.76 (m, 1H), 3.87 (s, 3H), 3.77 (m, 2H), 3.50 (t, J=10.1 Hz, 1H), 3.46 (t, J=10.1 Hz, 1H), 2.04-1.79 (m, 2H), 1.67 (m, 2H). ESI MS [M+H]$^+$ for C$_{22}$H$_{23}$N$_7$O$_3$, calcd 434.2, found 434.2.

Example 33: 1-[(R)-Tetrahydro-2H-pyran-3-yl]-3-{[4-(2-amino-8-methoxy-4-quinazolinyl)-1H-1,2,3-triazol-1-yl]methyl}-1H-pyridin-2-one

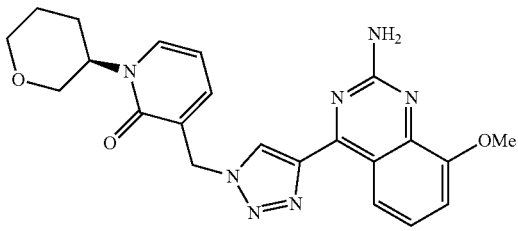 [SMILES: COc1cccc2c(-c3cn(Cc4cccn([C@@H]5CCCOC5)c4=O)nn3)nc(N)nc12]

The title compound was synthesized similar to Example 21 from the corresponding azide and alkyne derivatives. $^1$H NMR (400 MHz, DMSO-$d_6$) δ 8.76-8.67 (m, 1H), 8.60 (s, 1H), 7.88 (d, J=6.3 Hz, 1H), 7.49 (d, J=6.7 Hz, 1H), 7.15 (s, 2H), 6.86 (s, 2H), 6.41-6.19 (m, 1H), 5.51 (s, 2H), 4.76 (m, 1H), 3.87 (s, 3H), 3.77 (m, 2H), 3.50 (t, J=10.1 Hz, 1H), 3.46 (t, J=10.1 Hz, 1H), 2.04-1.79 (m, 2H), 1.67 (m, 2H). ESI MS [M+H]$^+$ for $C_{22}H_{23}N_7O_3$, calcd 434.2, found 434.2.

Example 34: 1-[(R)-1-(2-Hydroxy-2-methylpropionyl)-3-pyrrolidinyl]-3-{[4-(2-amino-8-methoxy-4-quinazolinyl)-1H-1,2,3-triazol-1-yl]methyl}-1H-pyridin-2-one

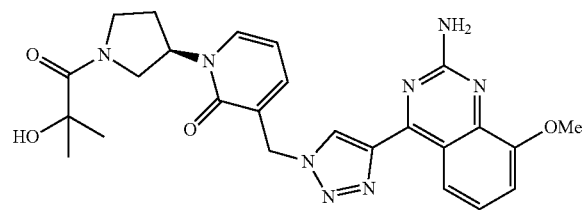 [SMILES: COc1cccc2c(-c3cn(Cc4cccn([C@@H]5CCN(C(=O)C(C)(C)O)C5)c4=O)nn3)nc(N)nc12]

The title compound was synthesized similar to Example 21 from the corresponding azide and alkyne derivatives. $^1$H NMR (400 MHz, DMSO-$d_6$) 8.90 (s, 2H), 7.67 (s, 1H), 7.62 (d, J=4 Hz, 1H), 7.55 (d, J=8 Hz, 1H), 7.48 (t, J=8 Hz, 1H), 6.39-6.36 (m, 1H), 5.59 (s, 2H), 5.23 (s, 2H), 4.13-4.11 (m, 1H), 4.03 (s, 3H), 3.99-3.77 (m, 3H), 3.55-3.45 (m, 2H), 2.29-2.07 (m, 2H), 1.29-1.17 (m, 6H). ESI MS [M+H]$^+$ for $C_{25}H_{29}N_8O_4$, calcd 505.2, found 505.3.

Example 35: 1-[(S)-Tetrahydrofur-3-yl]-3-{[4-(2-amino-8-methoxy-4-quinazolinyl)-1H-1,2,3-triazol-1-yl]methyl}-1H-pyridin-2-one

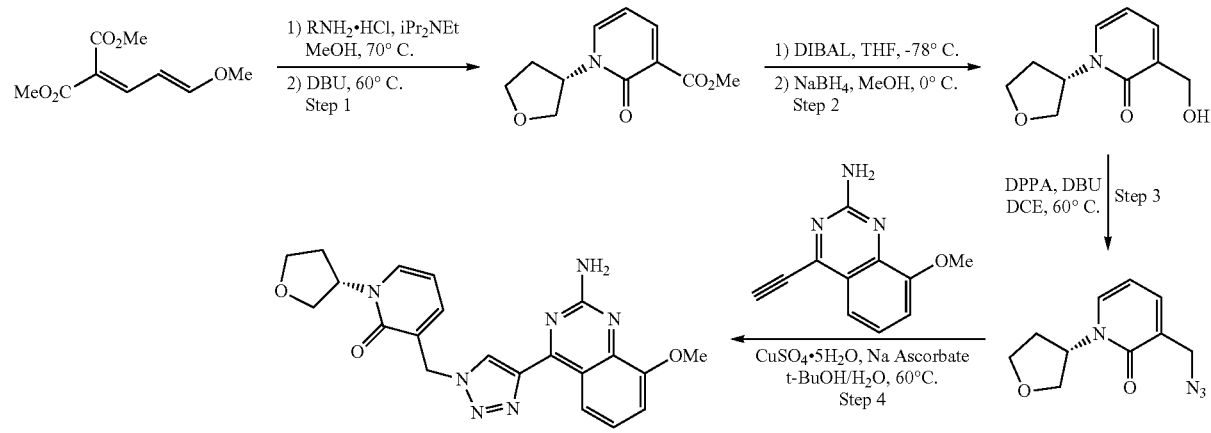

Step 1: In a 250 mL round bottom flask equipped with a magnetic stir bar was successively charged with the unsaturated dimethyl malonate (17 g, 84.9 mmol), MeOH (40 mL) and iPr$_2$NEt (17.3 mL, 97.1 mmol). The solution was heated to 60° C. and stirred at the same temperature for 1 hour under a nitrogen atmosphere. LCMS analysis showed the completion of the addition of amine to the unsaturated dimethyl malonate. The reaction mixture was then cooled to 23° C. To the above cooled solution were added RNH$_2$·HCl followed by DBU (12 mL, 97.7 mmol). The solution was then heated to 60° C. and stirred at that temperature for 4 hours. After completion of the reaction, solvent was removed under reduced pressure. MTBE (200 mL) followed by H$_2$O (150 mL) were added to the above crude mixture. The layers were separated and the aqueous layer was extracted back with MTBE (150 mL). Aqueous layer was acidified with 2(M) aqueous HCl to pH=4 followed by to pH=8 using aqueous NaHCO$_3$ solution. The basic aqueous layer was extracted with CH$_2$Cl$_2$/iPrOH (2:1, 300 mL) two times. The combined organic layer was dried over Na$_2$SO$_4$, evaporated to give crude pyridone (11.7 g, 65%) which was used for the next step without further purification.

Step 2: The product was synthesized in a similar manner to Example 19 from the corresponding ester derivative to afford yellow oil (769 mg, 57%).

Step 3: The product was synthesized in a similar manner to Example 1: colorless oil (118 mg, 35%).

Step 4: The product was synthesized in a similar manner to Example 1: yellow solid obtained (54 mg, 64%). $^1$H NMR (400 MHz, DMSO-$d_6$) δ 8.71 (s, 1H), 8.65-8.59 (m, 1H), 7.66 (d, J=7.0 Hz, 1H), 7.53 (d, J=6.9 Hz, 1H), 7.20-7.14 (m, 2H), 6.88 (s, 2H), 6.37 (t, J=6.9 Hz, 1H), 5.54 (s, 2H), 5.47-5.38 (m, 1H), 4.09-4.00 (m, 1H), 3.89 (s, 3H), 3.86-3.80 (m, 2H), 3.79-3.69 (m, 1H), 2.48-2.39 (m, 1H), 2.00-1.90 (m, 1H). ESI MS [M+H]$^+$ for $C_{21}H_{22}N_7O_3$, calcd 420.2, found 420.2.

Example 36: 1-[(S)-1-(1-Hydroxycyclopropyl)ethyl]-3-{[4-(2-amino-8-methoxy-4-quinazolinyl)-1H-1,2,3-triazol-1-yl]methyl}-1H-pyridin-2-one

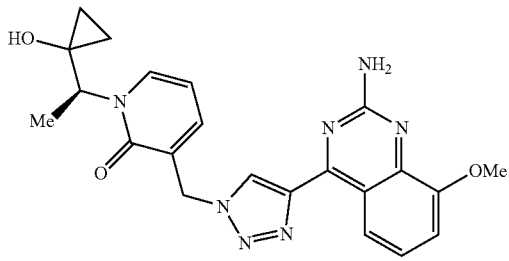 [SMILES: COc1cccc2c(-c3cn(Cc4cccn([C@@H](C)C5(O)CC5)c4=O)nn3)nc(N)nc12]

The title compound was synthesized in similar fashion to Example 35 from the corresponding azide and alkyne derivatives to afford 61 mg of a yellow solid. $^1$H NMR (400 MHz, DMSO-$d_6$) δ 8.70 (d, J=2.9 Hz, 1H), 8.61 (s, 1H), 7.93 (s, 1H), 7.48 (s, 1H), 7.16 (d, J=4.6 Hz, 2H), 6.86 (s, 2H), 6.34 (s, 1H), 5.72 (s, 1H), 5.52 (s, 2H), 4.62 (s, 1H), 3.88 (d, J=2.7 Hz, 3H), 1.37 (s, 2H), 0.85 (s, 1H), 0.68 (s, 2H), 0.58 (s, 2H). ESI MS [M+H]$^+$ for $C_{22}H_{23}N_7O_3$, calcd 434.2, found 434.2.

Example 37: 1-[(S)-1-(2-Hydroxy-2-methylpropionyl)-3-pyrrolidinyl]-3-{[4-(2-amino-8-methoxy-4-quinazolinyl)-1H-1,2,3-triazol-1-yl]methyl}-1H-pyridin-2-one

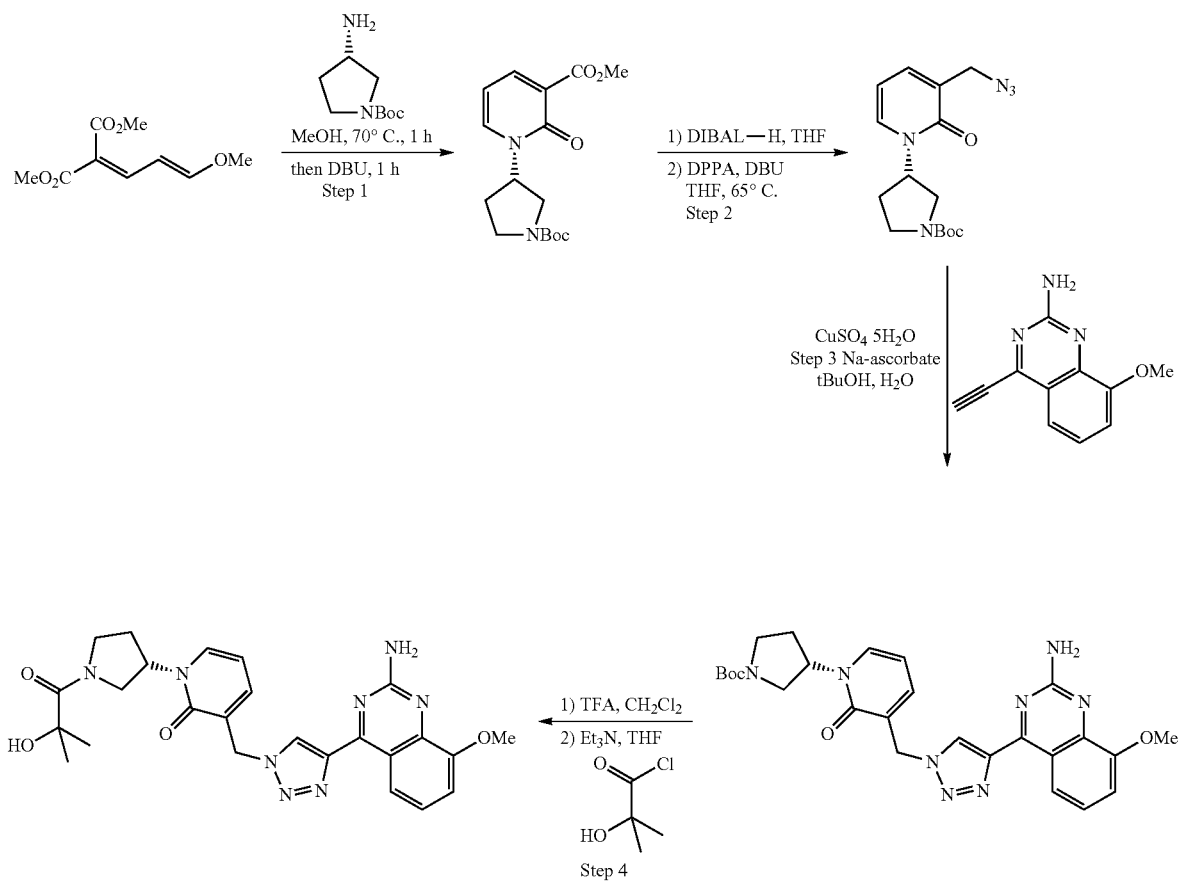

Steps 1-3: Similar to Example 35

Step 4: To a solution of N-Boc compound (0.4 g, 0.77 mmol) in $CH_2Cl_2$ (3.8 mL) was added trifluoro acetic acid (TFA, 1.92 mL, 25.1 mmol) at 23° C. The reaction mixture was stirred at 23° C. for 12 h. The solvent was evaporated to give the TFA salt which was used in the next step without further purification.

To a solution of above TFA salt (0.16 g, 0.39 mmol) in THF: DMF (1:2, 0.9 mL) was added Et₃N (0.17 mL, 1.2 mmol) at 23° C. and stirred for 5 mins. To the solution was added freshly prepared crude acid chloride (0.82 g, 6.7 mmol) and stirred for 1.5 h at 23° C. The solvent was removed under vacuum and purified by flash chromatography over silica gel (CH₂Cl₂/MeOH gradient 100% to 80%) followed by reverse phase HPLC to give the final alcohol (30 mg). $^1$H NMR (400 MHz, DMSO-$d_6$) 8.90 (s, 2H), 7.67 (s, 1H), 7.62 (d, J=8 Hz, 1H), 7.55 (d, J=8 Hz, 1H), 7.48 (t, J=8 Hz, 1H), 6.39-6.36 (m, 1H), 5.60 (s, 2H), 5.21 (s, 2 H), 4.13-4.11 (m, 1H), 4.03 (s, 3H), 3.98-3.74 (m, 2H), 3.55-3.46 (m, 2H), 2.29-2.08 (m, 3H), 1.30-1.23 (m, 6H). ESI MS [M+H]$^+$ for $C_{25}H_{29}N_8O_4$, calcd 505.2, found 505.4.

Example 38: 3-{[4-(2-Amino-8-fluoro-4-quinolyl)-1H-1,2,3-triazol-1-yl]methyl}-1-isopropyl-1H-pyridin-2-one

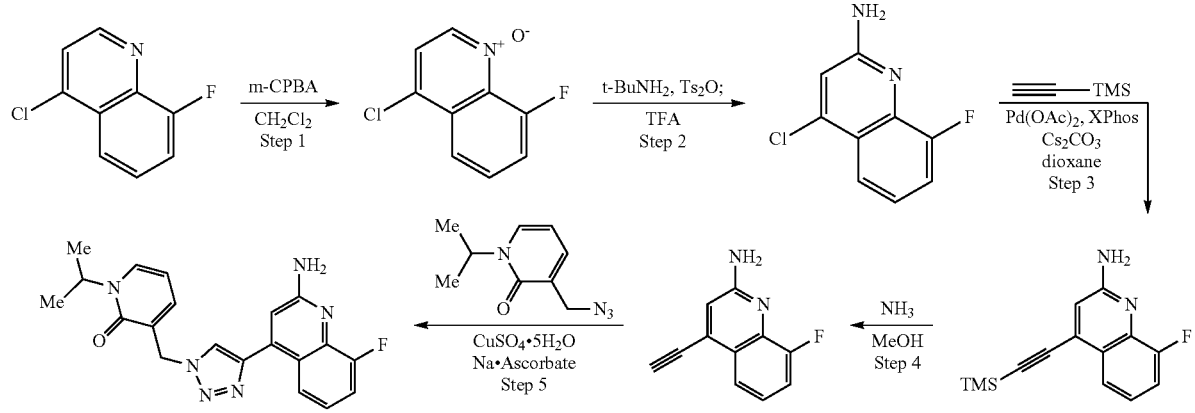

Step 1: m-CPBA (75%, 4.61 g, 20 mmol, 2 equiv.) was added to a solution of fluoroquinoline (1.82 g, 10 mmol, 1 equiv.) in CH₂Cl₂ (20 mL). The mixture stirred for 24 hours and was poured into 10% aqueous KOH. The mixture was extracted with CH₂Cl₂, and the combined organic layers were dried, filtered, and concentrated to give the quinoline N-oxide as a tan solid that was used without further purification.

Step 2: The quinoline N-oxide (1.54 g, 7.8 mmol, 1 equiv.) and t-BuNH₂ (4.1 mL, 39 mmol, 5 equiv.) were dissolved in CH₂Cl₂, and the mixture was cooled in an ice-water bath. Ts₂O (5.1 g, 15.6 mmol, 2 equiv.) was added in three portions over 10 minutes. TFA (19.5 mL) was added, and the mixture was heated to 70° C. until complete conversion to product was observed by LCMS. The mixture was cooled to ambient temperature and concentrated. The crude residue was dissolved in CH₂Cl₂, basified to pH~10 with 10% aqueous KOH, extracted, dried, and concentrated. The residue was purified by flash chromatography on SiO₂ to give the aminoquinoline as a dark solid.

Step 3: The aminoquinoline (1.50 g, 7.6 mmol, 1 equiv.), trimethylsilylacetylene (5.3 mL, 38 mmol, 5 equiv.), Cs₂CO₃ (7.4 g, 22.8 mmol, 3 equiv.), Pd(OAc)₂ (86 mg, 0.38 mmol, 5 mol %), and XPhos (340 mg, 0.76 mmol, 10 mol %) were dissolved in dioxane under and atmosphere of N₂, and the mixture was heated to 100° C. for 1.5 hours. The mixture was cooled to ambient temperature, filtered through Celite®, and concentrated. The residue was purified by flash chromatography on SiO₂ to give the silyl-protected alkyne as a dark oil.

Step 4: The protected alkyne (123 mg, 0.48 mmol) was dissolved in ~2 mL MeOH, and NH₃ (7 M in MeOH, 0.12 mL) was added. The mixture stirred for 2.5 hours and was concentrated to give the corresponding alkyne that was used without further purification.

Step 5: The title compound was synthesized in similar fashion to Example 1 from the corresponding azide and alkyne derivatives to afford 39 mg of a yellow solid. $^1$H NMR (400 MHz, DMSO-$d_6$) δ 8.74-8.65 (m, 1H), 8.02 (d, J=8.6 Hz, 1H), 7.81 (dd, J=6.9, 2.1 Hz, 1H), 7.44-7.26 (m, 2H), 7.21-7.11 (m, 2H), 6.81 (s, 2H), 6.34 (ddd, J=7.9, 6.1, 1.2 Hz, 1H), 5.51 (s, 2H), 5.16-5.04 (m, 1H), 1.38-1.22 (m, 6H). ESI MS [M+H]$^+$ for $C_{20}H_{19}FN_6O$, calcd 379.2, found 379.2.

Example 39: 3-{[4-(2-Amino-8-methoxy-4-quinazolinyl)-1H-pyrazol-1-yl]methyl}-1-isopropyl-1H-pyridin-2-one

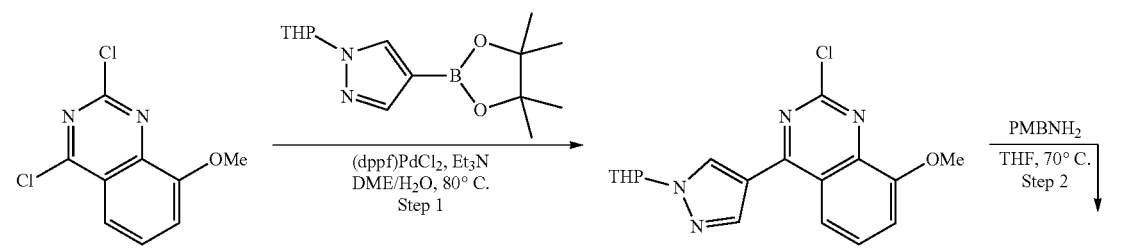

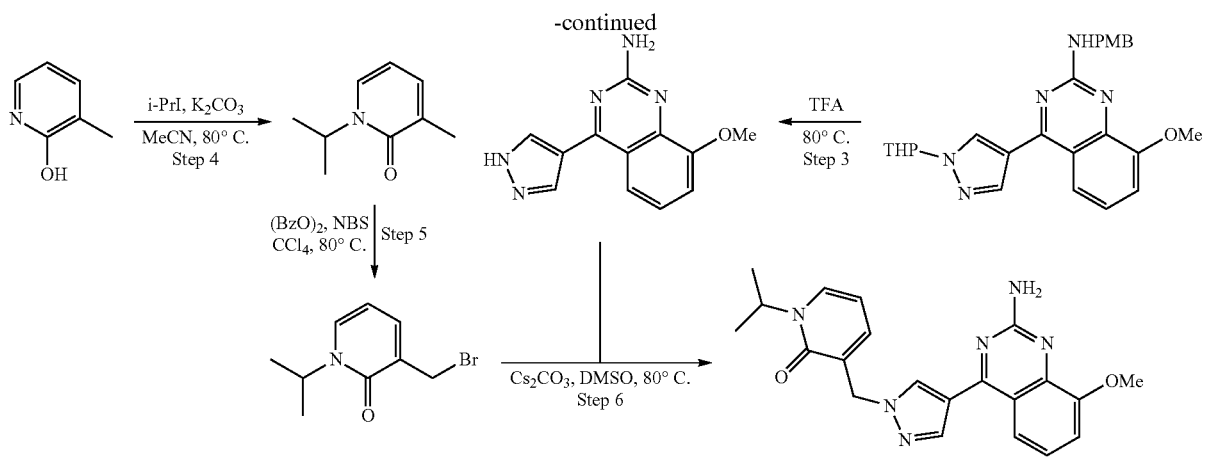

Step 1: A degassed mixture of 2,4-dichloro-8-methoxy-quinazoline (61.8 g, 270 mmol), 1-(Tetrahydro-2H-pyran-2-yl)-1H-pyrazole-4-boronic acid pinacol ester (25.0 g, 90.0 mmol), [1,1'-bis(diphenylphosphino)ferrocene]palladium(II) dichloride (6.58 g, 9.00 mmol), triethylamine (75.3 mL, 540 mmol), DME (450 mL), and water (11 mL) was stirred at 80° C. for 16 hours. The mixture was concentrated onto silica gel and purified by silica gel chromatography (0 to 40% EtOAc in $CH_2Cl_2$) to afford the desired product as a yellow foam (6.94 g; 22%).

Step 2: A mixture of the product from step 1 (1.69 g, 4.90 mmol), 4-methoxybenzylamine (1.23 mL), and THF (2.5 mL) was stirred at 70° C. for 20 hours. EtOAc (100 mL) and 10% (w/w) citric acid$_{(aq)}$ (200 mL) was added. The resultant formed precipitate was collected by filtration, washed with water and EtOAc, and dried to afford the desired product as a yellow solid (2.18 g, 100%).

Step 3: A mixture of the product from step 2 (890 mg, 2.00 mmol) and TFA (10 mL) was stirred at 80° C. for 2 hours. The mixture was added to a stirring flask of water (200 mL) and basified to pH 10 with 1M NaOH$_{(aq)}$. The solids were collected by filtration, washed with water, and triturated with MTBE (10 mL, 60° C.) for 30 minutes to afford the desired product as a light yellow solid (308 mg; 64%).

Step 4: A mixture of 2-hydroxy-3-methylpyridine (2.73 g, 25.0 mmol), 2-iodopropane (5.00 mL, 50.0 mmol), potassium carbonate (6.90 g, 50.0 mmol), and acetonitrile (50 mL) was stirred at 80° C. for 3 hours and at 70° C. for 13 hours. The mixture was filtered to remove any solids. The filtrate was concentrated onto silica gel and purified by silica gel chromatography (0 to 100% EtOAc in hexanes) to afford the desired product as a yellow oil (977 mg; 26%).

Step 5: The product was synthesized in a similar manner to Example 8, step 2: yellow solid obtained (859 mg, 58%).

Step 6: A mixture of the product from step 3 (41 mg, 0.17 mmol), the product from step 5 (39 mg, 0.17 mmol), cesium carbonate (78 mg, 0.20 mmol), and DMSO (0.7 mL) was stirred at 80° C. for 15 hours. The mixture was added to 1:1 brine/water solution (10 mL) and solids were collected by filtration. The crude material was purified by reversed-phase HPLC to afford the desired product as a yellow film (6.7 mg; 10%). $^1$H NMR (400 MHz, DMSO-d$_6$) δ 8.84 (s, 1H), 8.29 (s, 1H), 7.98 (d, J=8.4 Hz, 1H), 7.79 (d, J=6.6 Hz, 1H), 7.61 (d, J=8.2 Hz, 1H), 7.49 (t, J=8.4 Hz, 1H), 7.28 (d, J=7.4 Hz, 1H), 6.32 (t, J=6.8 Hz, 1H), 5.29 (s, 2H), 5.08 (hept, J=6.4 Hz, 1H), 4.06 (s, 3H), 1.29 (d, J=6.8 Hz, 6H). ESI MS [M+H]$^+$ for $C_{21}H_{23}N_6O_2$, calcd 391.2, found 391.2.

Example 40: 3-{[4-(2-Amino-8-methoxy-4-quinazolinyl)-1H-pyrazol-1-yl]methyl}-1-ethyl-1H-pyridin-2-one

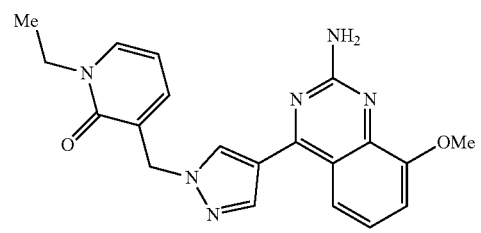 [SMILES: CCn1cccc(Cn2cc(-c3nc(N)nc4c(OC)cccc34)cn2)c1=O]

The title compound was synthesized in similar fashion to Example 39 from the corresponding bromide and pyrazole derivatives to afford 43 mg of a yellow solid. $^1$H NMR (400 MHz, DMSO-d$_6$) δ 8.51 (s, 1H), 8.06 (s, 1H), 7.73 (s, 1H), 7.67 (d, J=7.4 Hz, 1H), 7.62-7.43 (m, 1H), 7.16-7.08 (m, 2H), 6.76 (s, 2H), 6.26 (s, 1H), 5.24 (s, 2H), 3.94 (s, 2H), 3.87 (d, J=2.8 Hz, 3H), 1.22 (s, 3H). ESI MS [M+H]$^+$ for $C_{20}H_{20}N_6O_2$, calcd 377.2, found 377.2.

Example 41: 3-{[4-(2-Amino-8-methoxy-4-quinazolinyl)-1H-pyrazol-1-yl]methyl}-1-cyclopropyl-1H-pyridin-2-one

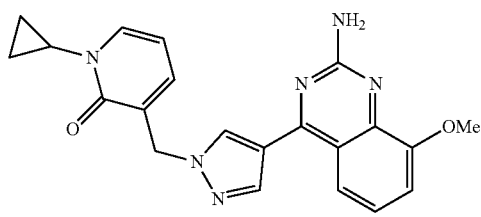 [SMILES: COc1cccc2c(-c3cnn(Cc4cccn(C5CC5)c4=O)c3)nc(N)nc12]

The title compound was prepared similar to Example 39 from the corresponding bromide and pyrazole derivatives. $^1$H NMR (400 MHz, DMSO-d$_6$) δ 8.84 (s, 1H), 8.30 (s, 1H), 7.99 (d, J=8.5 Hz, 1H), 7.66-7.56 (m, 2H), 7.51 (t, J=8.2 Hz, 1H), 7.35 (d, J=6.8 Hz, 1H), 6.23 (t, J=6.8 Hz, 1H), 5.29 (s, 2H), 4.07 (s, 3H), 3.41-3.32 (m, 1H), 1.05-0.93 (m, 2H), 0.91-0.76 (m, 2H). ESI MS [M+H]$^+$ for $C_{21}H_{21}N_6O_2$, calcd 389.2, found 389.2.

Example 42: 1-[(R)-1-(Tetrahydro-2H-pyran-4-yl)ethyl]-3-{[4-(2-amino-8-methoxy-4-quinazolinyl)-1H-pyrazol-1-yl]methyl}-1H-pyridin-2-one

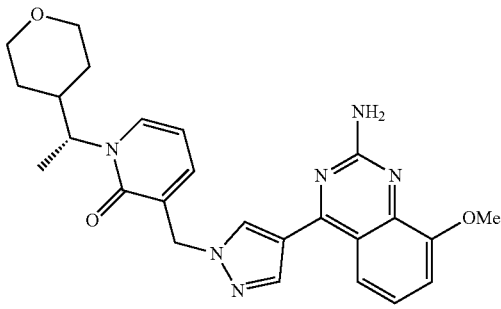 [SMILES: COc1cccc2c(-c3cnn(Cc4cccn([C@H](C)C5CCOCC5)c4=O)c3)nc(N)nc12]

The title compound was synthesized similar to Example 39 from the corresponding bromide and pyrazole derivatives. $^1$H NMR (400 MHz, DMSO-$d_6$) δ 8.49 (s, 1H), 8.06 (d, J=2.5 Hz, 1H), 7.64 (d, J=8.8 Hz, 2H), 7.16-6.94 (m, 3H), 6.73 (s, 2H), 6.27 (d, J=6.9 Hz, 1H), 5.40-5.04 (m, 2H), 4.75 (m, 1H), 3.92-3.79 (m, 4H), 3.72 (d, J=11.5 Hz, 1H), 3.23 (t, J=11.7 Hz, 1H), 3.11 (t, J=11.7 Hz, 1H), 1.89 (m, 1H), 1.67 (d, J=10.0 Hz, 1H), 1.28 (d, J=7.1 Hz, 3H), 1.22 (m, 1H), 1.03 (m, 2H). ESI MS [M+H]$^+$ for $C_{25}H_{28}N_6O_3$, calcd 461.2, found 461.2.

Example 43: 3-{[4-(2-Amino-8-methoxy-4-quinolyl)-1H-1,2,3-triazol-1-yl]methyl}-1-isopropyl-1H-pyridin-2-one

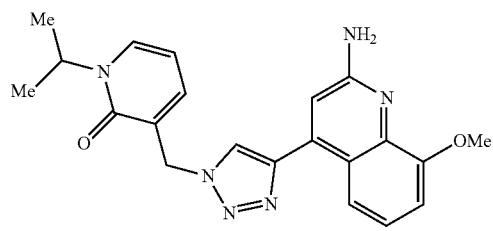 [SMILES: COc1cccc2c(-c3cn(Cc4cccn(C(C)C)c4=O)nn3)cc(N)nc12]

The title compound was synthesized in similar fashion to Example 38 from the corresponding azide and alkyne derivatives to afford 100 mg of an orange solid. $^1$H NMR (400 MHz, DMSO-$d_6$) δ 8.64 (s, 1H), 7.81 (dd, J=7.0, 2.0 Hz, 1H), 7.72 (dd, J=8.3, 1.4 Hz, 1H), 7.36 (dd, J=6.8, 1.8 Hz, 1H), 7.17-6.99 (m, 3H), 6.57 (s, 2H), 6.34 (t, J=6.9 Hz, 1H), 5.50 (s, 2H), 5.10 (p, J=6.8 Hz, 1H), 3.87 (s, 3H), 1.30 (d, J=6.8 Hz, 6H). ESI MS [M+H]$^+$ for $C_{21}H_{22}N_6O_2$, calcd 391.2, found 391.2.

Analytical Methods

LC: Agilent 1100 series; Mass spectrometer: Agilent G6120BA, single quad

LC-MS method: Agilent Zorbax Eclipse Plus C18, 4.6×100 mm, 3.5 μM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile Flash column: ISCO Rf+

Reverse phase HPLC: ISCO-EZ or Agilent 1260; Column: Kinetex 5 μm EVO C18 100 A; 250×21.2 mm (Phenomenex)

Biological Example

Measurement of the Adenosine Receptor Activity of Compounds Using a Human 2A Adenosine Receptor ($A_{2a}R$) CHO-TREx cAMP Functional Assay The cAMP antagonist functional assay (Perkin Elmer) was performed on CHO-T-REx cells induced to express Human $A_{2A}R$. Cells were seeded to a white 384-well Opti plate at a density of 1,000 to 2,500 cells per well followed by incubation with various concentrations of compound (ranging from 1 μM to 0 μM) at 37° C. for 1 hour.

A 1:2 serial dilution of NECA (Sigma Aldrich) from 1 μM to 0 μM was added to the cell stimulation mixture and incubated for 30 min at 37° C. After 30 min incubation, 5 μL of Ulight-anti-cAMP (1:150 dilution with conjugate and lysis buffer provided by Perkin Elmer) and 5 μL of Eu-cAMP tracer (1:50 dilution with conjugate and lysis buffer provided by Perkin Elmer) was added the cells and incubated for an hour. FRET signal was detected with an Envision multilabel plate reader (Perkin Elmer) loaded with 615 nm excitation filters and 665 nm emission filters.

Data analysis was performed using on GraphPad Prism (version 7.02) to determine the KB of the test compounds.

Measurement of the Adenosine Receptor Activity of Compounds Using a Human 2B Adenosine Receptor CHO-K1 cAMP Functional Assay CHO-K1 cells stably expressing Human Adenosine 2B Receptor ($A_{2B}R$: Cat. No. M000329, GenScript) were purchased from GenScript Inc., Piscataway, NJ 08854, USA.

The cAMP antagonist functional assay (Perkin Elmer) was performed on CHO-K1 cells stably expressing Human $A_{2B}R$. 1×10$^6$ cells were seeded in T75 flasks and cultured at 37° C. and 5% $CO_2$ overnight. 2,000-4,000 cells/well of stably-expressed $A_{2b}R$ CHO-K1 cells were then seeded to a white 384-well Opti plate followed by compound 1 incubation at various concentrations (ranging from 1 μM to 0 μM) at 37° C. for 1 hour.

A 1:2 serial dilution of NECA (Sigma Aldrich) from 1 μM to 0 μM was added to the cell stimulation mixture and incubated for 30 min at 37° C. After 30 min incubation, 5 μL of Ulight-anti-cAMP (1:150 dilution with conjugate and lysis buffer provided by Perkin Elmer) and 5 μL of Eu-cAMP tracer (1:50 dilution with conjugate and lysis buffer provided by Perkin Elmer) was added the cells and incubated for an hour. FRET signal was detected with an Envision multilabel plate reader (Perkin Elmer) loaded with 615 nm excitation filters and 665 nm emission filters.

Data analysis was performed using on GraphPad Prism (version 7.02) to determine the KB of the test compounds.

TABLE 1

Specific Examples (Potency: $A_{2A}R$ and $A_{2B}R$ $K_B$: + means > 1 μM,
++ means 100 nM to 1 μM, +++ means < 100 nM)

| Example | $A_{2A}$ | $A_{2B}$ |
|---|---|---|
| (structure) | +++ | +++ |
| (structure) | +++ | +++ |
| (structure) | +++ | +++ |
| (structure) | +++ | ++ |
| (structure) | +++ | +++ |
| (structure) | +++ | +++ |

TABLE 1-continued

Specific Examples (Potency: $A_{2A}R$ and $A_{2B}R$ $K_B$: + means > 1 μM,
++ means 100 nM to 1 μM, +++ means < 100 nM)

| Example | $A_{2A}$ | $A_{2B}$ |
|---|---|---|
| (structure) | +++ | +++ |
| (structure) | +++ | ++ |
| (structure) | +++ | +++ |
| (structure) | +++ | +++ |
| (structure) | +++ | +++ |
| (structure) | +++ | +++ |
| (structure) | +++ | + |

TABLE 1-continued

Specific Examples (Potency: $A_{2A}R$ and $A_{2B}R$ $K_B$: + means > 1 µM, ++ means 100 nM to 1 µM, +++ means < 100 nM)

| Example | $A_{2A}$ | $A_{2B}$ |
|---|---|---|
| (structure) | +++ | ++ |
| (structure) | +++ | +++ |
| (structure) | +++ | +++ |
| (structure) | +++ | ++ |
| (structure) | +++ | ++ |
| (structure) | +++ | +++ |

TABLE 1-continued
Specific Examples (Potency: $A_{2A}R$ and $A_{2B}R$ $K_B$: + means > 1 μM,
++ means 100 nM to 1 μM, +++ means < 100 nM)
| Example | $A_{2A}$ | $A_{2B}$ |
|---|---|---|
| 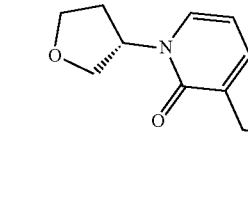 | +++ | ++ |
| 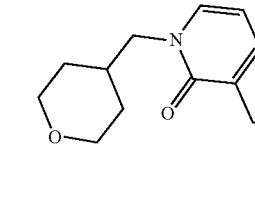 | +++ | +++ |
| 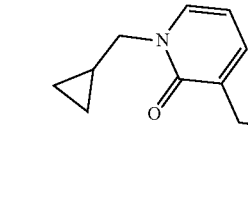 | +++ | +++ |
| 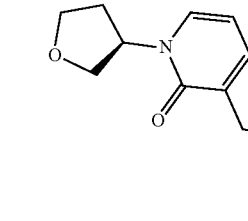 | +++ | +++ |
| 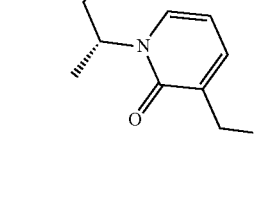 | +++ | +++ |
| 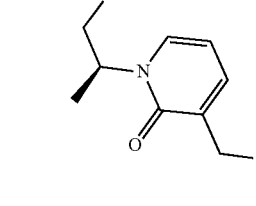 | +++ | ++ |

TABLE 1-continued

Specific Examples (Potency: $A_{2A}R$ and $A_{2B}R$ $K_B$: + means > 1 μM,
++ means 100 nM to 1 μM, +++ means < 100 nM)

| Example | $A_{2A}$ | $A_{2B}$ |
|---|---|---|
| [structure] | +++ | +++ |
| [structure] | +++ | ++ |
| [structure] | +++ | +++ |
| [structure] | +++ | +++ |
| [structure] | +++ | +++ |
| [structure] | +++ | +++ |

TABLE 1-continued

Specific Examples (Potency: $A_{2A}R$ and $A_{2B}R$ $K_B$: + means > 1 μM, ++ means 100 nM to 1 μM, +++ means < 100 nM)

| Example | $A_{2A}$ | $A_{2B}$ |
|---|---|---|
| | +++ | +++ |
| | +++ | ++ |
| | +++ | +++ |
| | +++ | ++ |
| | +++ | +++ |
| | +++ | +++ |

TABLE 1-continued

Specific Examples (Potency: $A_{2A}R$ and $A_{2B}R$ $K_B$: + means > 1 μM,
++ means 100 nM to 1 μM, +++ means < 100 nM)

| Example | $A_{2A}$ | $A_{2B}$ |
|---|---|---|
| (structure) | +++ | +++ |
| (structure) | +++ | +++ |
| (structure) | +++ | ++ |
| (structure) | +++ | ++ |
| (structure) | +++ | ++ |
| (structure) | +++ | +++ |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

Measurement of the Adenosine Receptor Activity of Compounds Using a Human 2B Adenosine Receptor CHO-K1 cAMP Functional Assay CHO-K1 cells stably expressing Human Adenosine 2B Receptor ($A_{2B}R$: Cat. No. M000329, GenScript) were purchased from GenScript Inc., Piscataway, NJ 08854, USA.

The cAMP antagonist functional assay (Perkin Elmer) was performed on CHO-K1 cells stably expressing Human $A_{2B}R$. $1\times10^6$ cells were seeded in T75 flasks and cultured at 37° C. and 5% $CO_2$ overnight. 2,000-4,000 cells/well of stably-expressed $A_{2B}R$ CHO-$K_1$ cells were then seeded to a white 384-well Opti plate followed by compound 1 incubation at various concentrations (ranging from 1 µM to 0 µM) at 37° C. for 1 hour.

A 1:2 serial dilution of NECA (Sigma Aldrich) from 1 µM to 0 µM was added to the cell stimulation mixture and incubated for 30 min at 37° C. After 30 min incubation, 5 µL of Ulight-anti-cAMP (1:150 dilution with conjugate and lysis buffer provided by Perkin Elmer) and 5 µL of Eu-cAMP tracer (1:50 dilution with conjugate and lysis buffer provided by Perkin Elmer) was added the cells and incubated for an hour. FRET signal was detected with an Envision multilabel plate reader (Perkin Elmer) loaded with 615 nm excitation filters and 665 nm emission filters.

Data analysis was performed using on GraphPad Prism (version 7.02) to determine the $K_B$ of the test compounds.

What is claimed is:

1. A compound represented by Formula (I)

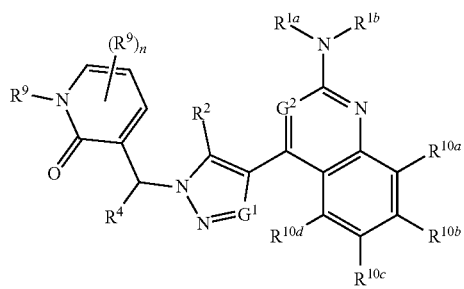

or a pharmaceutically acceptable salt, hydrate, or solvate thereof, wherein, $G^1$ is N or $CR^{3a}$;
$G^2$ is N or $CR^{3b}$;
$R^{3a}$ and $R^{3b}$ are each independently H or $C_{1-3}$ alkyl;
$R^{1a}$ and $R^{1b}$ are each independently selected from the group consisting of
i) H,
ii) $C_{1-8}$ alkyl optionally substituted with from 1-3 $R^5$ substituents,
iii) —$X^1$—O—$C_{1-8}$ alkyl optionally substituted with from 1-3 $R^5$ substituents,
iv) —C(O)—$R^6$,
v) Y optionally substituted with 1-3 $R^7$ substituents,
vi) —$X^1$—Y optionally substituted with 1-3 $R^7$ substituents; and vii) $R^{1a}$ and $R^{1b}$ together with the nitrogen to which they are attached form a 5-6 membered heterocycloalkyl ring optionally substituted with from 1-3 $R^8$ substituents, wherein the heterocycloalkyl has 0-2 additional heteroatom ring vertices selected from the group consisting of O, N, and S;

each Y is $C_{3-8}$ cycloalkyl or 4 to 6-membered heterocycloalkyl having 1-3 heteroatom ring vertices selected from the group consisting of O, N, and S;

$R^2$ and $R^4$ are each independently H or $C_{1-3}$ alkyl;

each $X^1$ is $C_{1-6}$ alkylene;

each $R^5$ is independently selected from the group consisting of hydroxyl, $C_{3-8}$ cycloalkyl, phenyl, —O-phenyl, —C(O)$OR^a$, and oxo;

each $R^6$ is $C_{1-8}$ alkyl or Y, each of which is optionally substituted with 1-3 substituents selected from the group consisting of hydroxyl, —O-phenyl, phenyl, and —O—$C_{1-8}$ alkyl;

each $R^7$ is independently selected from the group consisting of $C_{1-8}$ alkyl, hydroxyl, —O—$C_{1-8}$ alkyl, oxo, and —C(O)$OR^a$;

each $R^8$ is independently selected from the group consisting of $C_{1-8}$ alkyl, hydroxyl, and oxo;

the subscript n is 0, 1, 2 or 3;

each $R^9$ is independently selected from the group consisting of $C_{1-8}$ alkyl, —O—$C_{1-8}$ alkyl, —$X^1$—O—$C_{1-8}$ alkyl, —O—$X^1$—O—$C_{1-8}$ alkyl, —$X^1$—O—$X^1$—O—$C_{1-8}$ alkyl, —C(O)$OR^a$, halogen, cyano, —$NR^bR^c$, Y, —$X^1$—$C_{3-8}$ cycloalkyl, and —$X^2$—Z, wherein $X^2$ is selected from the group consisting of $C_{1-6}$ alkylene, —$C_{1-6}$ alkylene-O—, —$C_{1-4}$ alkylene-O—$C_{1-4}$ alkylene-, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$;

each of $R^{10a}$, $R^{10b}$, $R^{10c}$, and $R^{10d}$ is independently selected from the group consisting of H, $C_{1-8}$ alkyl, halo, cyano, —O—$C_{1-8}$ alkyl, —$X^1$—O—$C_{1-8}$ alkyl, —O—$X^1$—O—$C_{1-8}$ alkyl, —S(O)$_2$—$C_{1-6}$ alkyl, —C(O)$NR^dR^c$, and 4-6-membered heteroaryl having from 1-3 heteroatom ring vertices selected from the group consisting of O, N, and S, wherein each of said $R^{10a-d}$ substituents is optionally substituted with 1-3 $R^{12}$, or two of $R^{10a}$, $R^{10b}$, $R^{10c}$ and $R^{10d}$ on adjacent ring vertices are optionally combined to form a 5-membered heterocyclic ring optionally substituted with 1-2 halogens;

each $R^{11}$ is independently selected from the group consisting of hydroxyl, oxo, halo, cyano, —$NR^dR^e$, —C(O)$OR^a$, phenyl, $C_{3-8}$ cycloalkyl, and $C_{1-4}$ alkyl optionally substituted with —C(O)$OR^a$;

each $R^{12}$ is independently selected from the group consisting of halo, cyano, hydroxy, and —C(O)$OR^a$;

each $R^a$ is H or $C_{1-6}$ alkyl;

each $R^b$ and $R^c$ are independently selected from the group consisting of H, $C_{1-8}$ alkyl, —S(O)$_2$—$C_{1-6}$ alkyl, —C(O)$OR^a$, and —$X^1$—C(O)$OR^a$; and each $R^d$ and $R^e$ are independently selected from the group consisting of H, $C_{1-8}$ alkyl, and —S(O)$_2$—$C_{1-6}$ alkyl.

2. The compound of claim 1, having Formula (Ia):

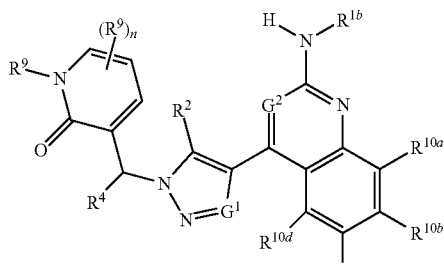

(Ia)

or a pharmaceutically acceptable salt, hydrate, or solvate thereof.

3. The compound of claim 1, having Formula (Ib):

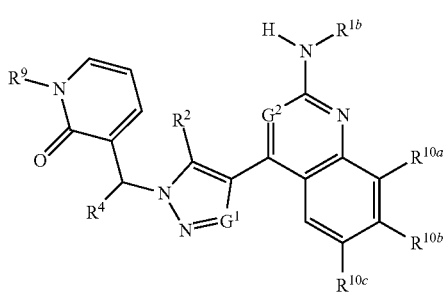

(Ib)

or a pharmaceutically acceptable salt, hydrate, or solvate thereof.

4. The compound of claim 1, wherein at least one of $R^{10a}$, $R^{10b}$ and $R^{1c}$ is methoxy.

5. The compound claim 1, having Formula (Ic):

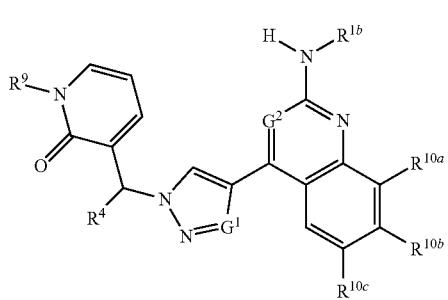

(Ic)

or a pharmaceutically acceptable salt, hydrate, or solvate thereof.

6. The compound of claim 1, having Formula (Id):

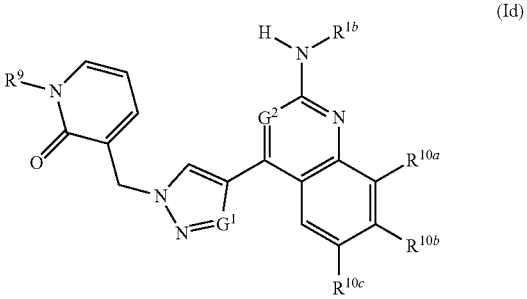

(Id)

or a pharmaceutically acceptable salt, hydrate, or solvate thereof.

7. The compound of claim 1, or a pharmaceutically acceptable salt, hydrate, or solvate thereof, wherein each $R^9$ is independently selected from the group consisting of $C_{1-8}$ alkyl, —O—$C_{1-8}$ alkyl, —$X^1$—O—$C_{1-8}$ alkyl, —O—$X^1$—O—$C_{1-8}$ alkyl, and —$X^1$—O—$X^1$—O—$C_{1-8}$ alkyl, wherein each of said $R^9$ substituents is optionally substituted with 1-3 $R^{11}$.

8. The compound of claim 1, or a pharmaceutically acceptable salt, hydrate, or solvate thereof, wherein each $R^9$ is independently selected from the group consisting of —C(O)OR$^a$, —NR$^b$R$^c$, Y, —$X^1$—$C_{3-8}$ cycloalkyl, and —$X^2$—Z, wherein $X^2$ is selected from the group consisting of $C_{1-6}$ alkylene, —$C_{1-6}$ alkylene-O—, —C(O)—, and —S(O)$_2$—, Z is 4 to 6-membered heterocycloalkyl having 1-3 heteroatom ring vertices selected from the group consisting of O, N, and S, and wherein each of said $R^9$ substituents is optionally substituted with 1-3 $R^{11}$.

9. The compound of claim 1, having Formula (Ie):

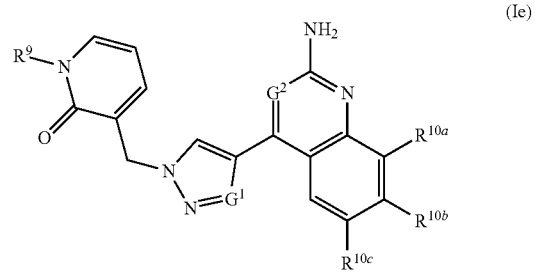

(Ie)

or a pharmaceutically acceptable salt, hydrate, or solvate thereof.

10. The compound of claim 1, having Formula (If):

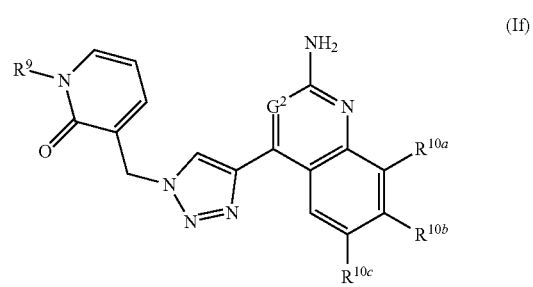

(If)

or a pharmaceutically acceptable salt, hydrate, or solvate thereof.

11. The compound of claim 1, having Formula (Ig):

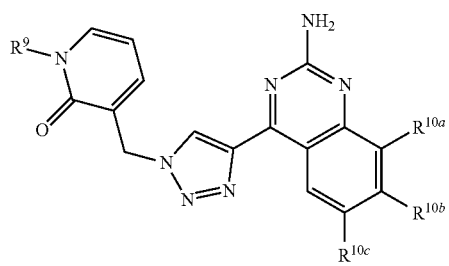

(Ig)

or a pharmaceutically acceptable salt, hydrate, or solvate thereof.

12. The compound of claim 1, having Formula (Ih):

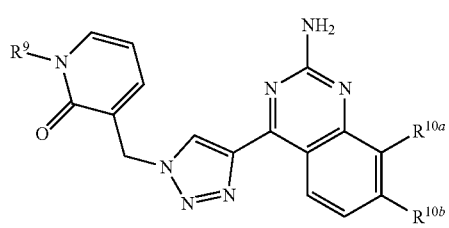

(Ih)

or a pharmaceutically acceptable salt, hydrate, or solvate thereof.

13. The compound of claim 1, having Formula (Ii):

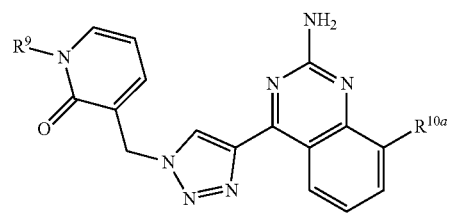

(Ii)

or a pharmaceutically acceptable salt, hydrate, or solvate thereof.

14. The compound of claim 1, selected from the group consisting of:

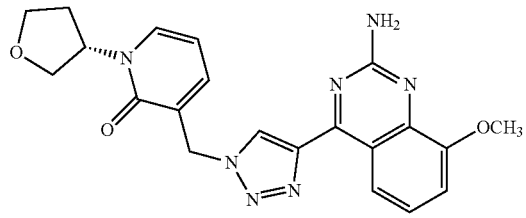

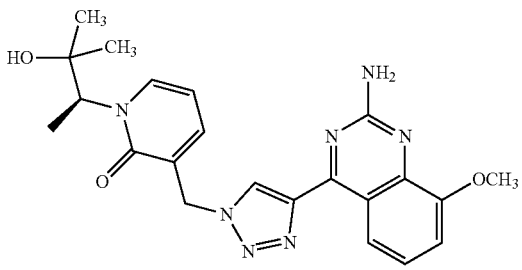

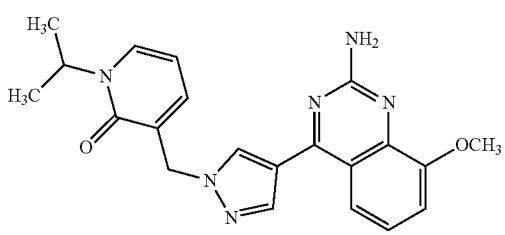

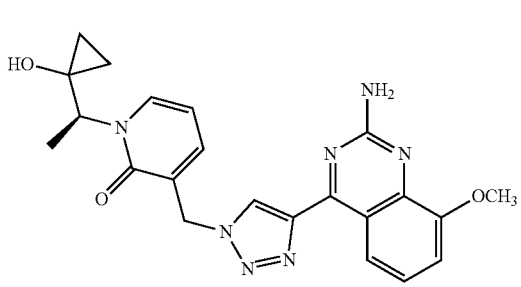

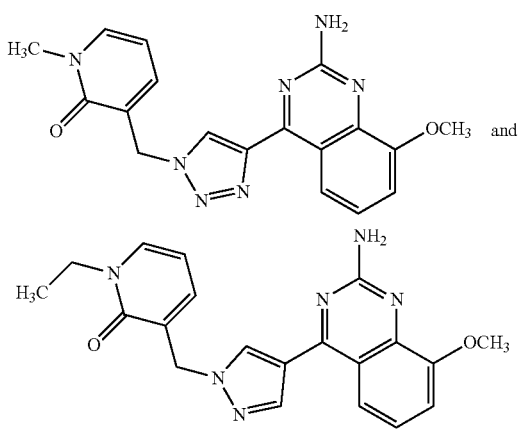

or a pharmaceutically acceptable salt, hydrate, or solvate thereof.

15. A compound selected from the group consisting of:

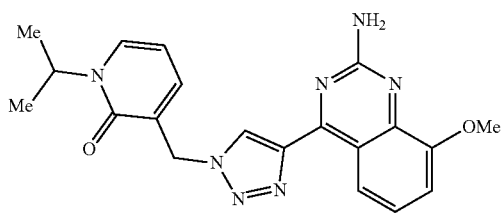

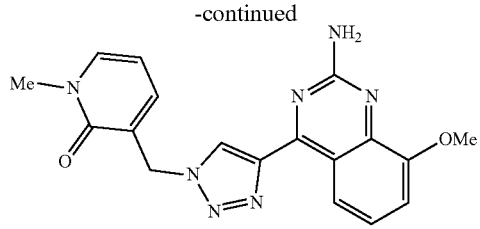
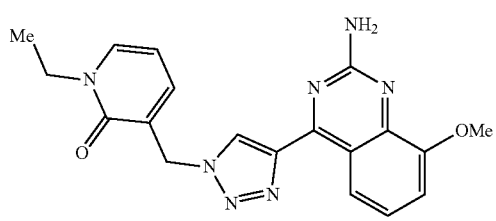
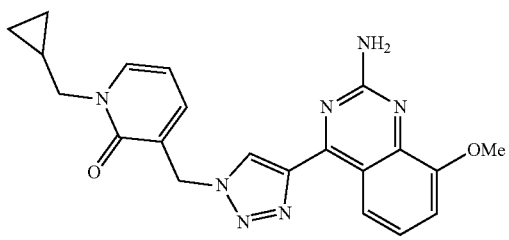
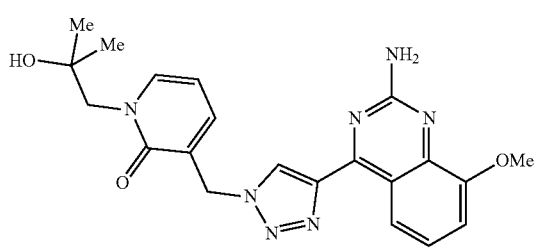 [SMILES: COc1cccc2c(-c3cn(Cc4cccn(CC(C)(C)O)c4=O)nn3)nc(N)nc12]
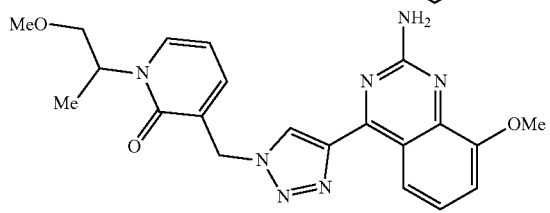
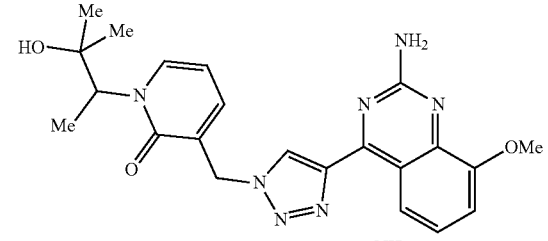 [SMILES: COc1cccc2c(-c3cn(Cc4cccn(C(C)C(C)(C)O)c4=O)nn3)nc(N)nc12]
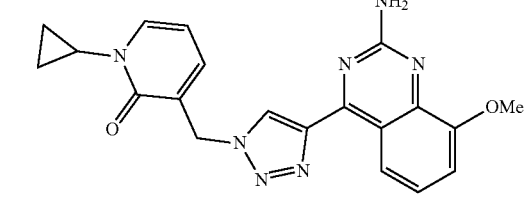
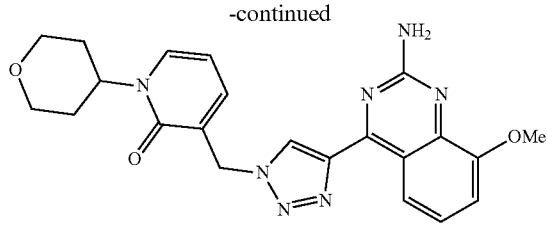
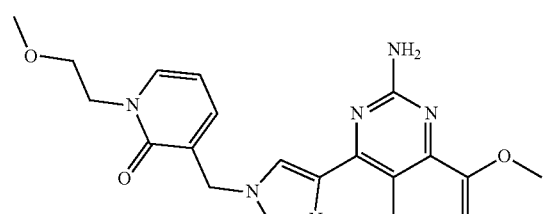
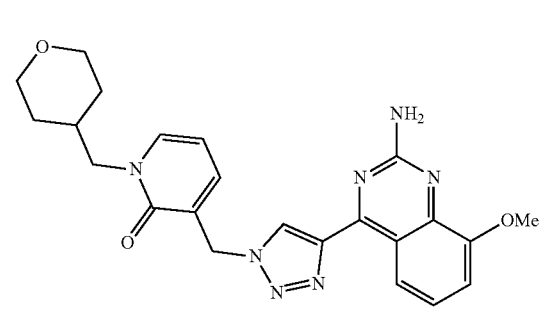
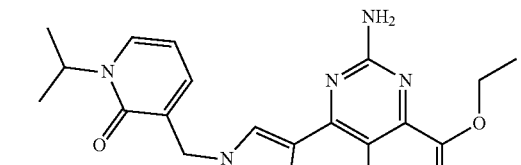
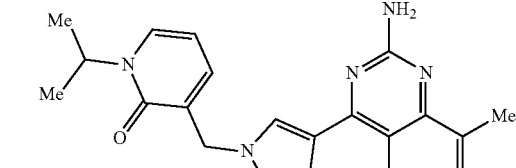
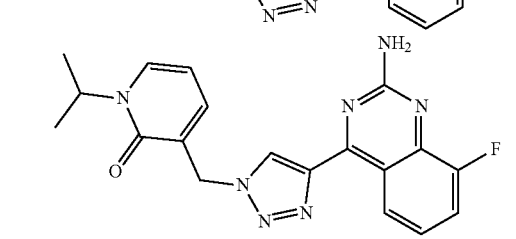
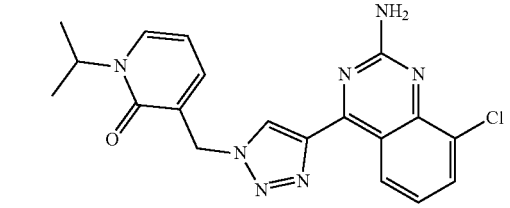

-continued
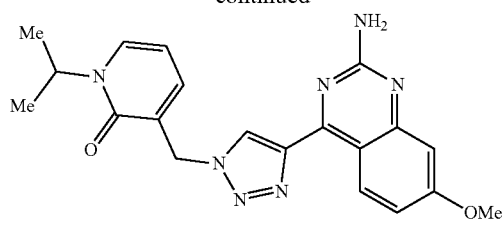
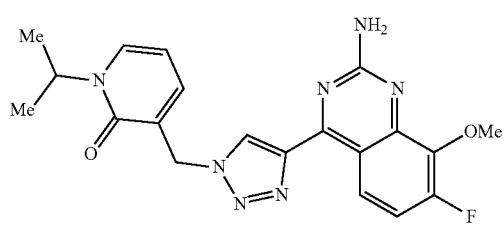
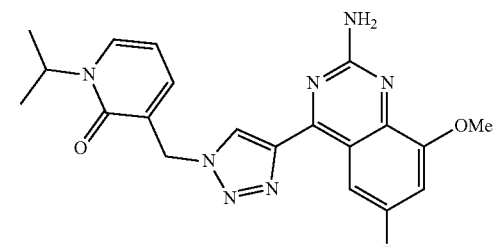
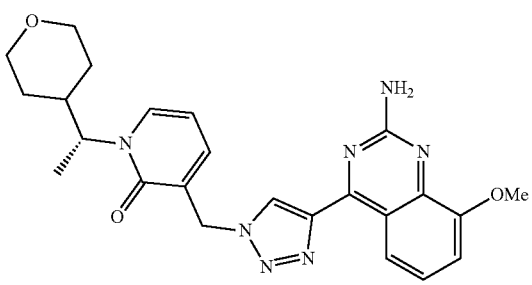
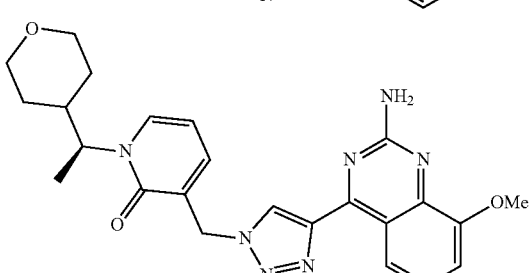
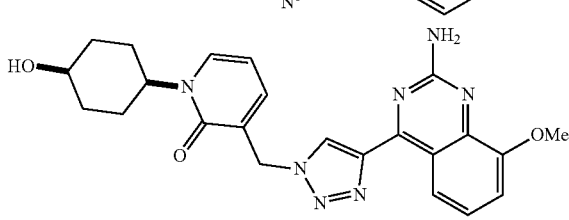
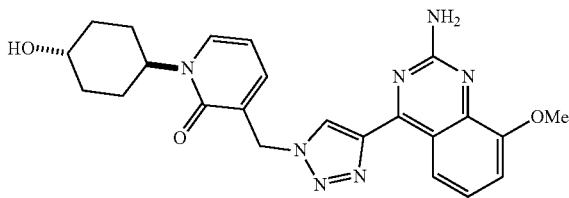
-continued
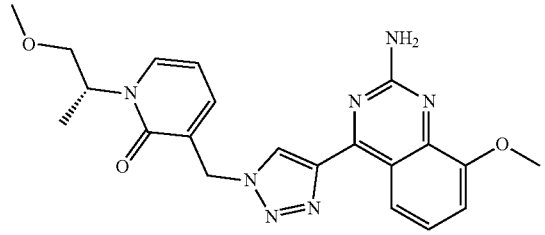
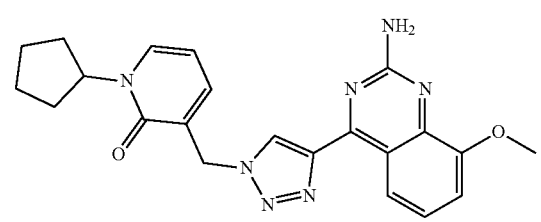
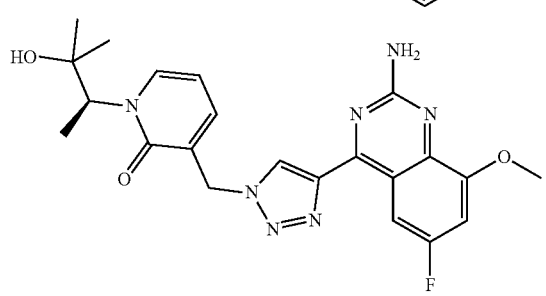
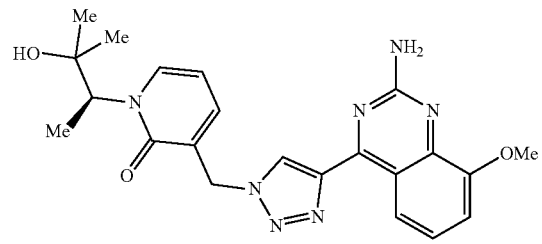
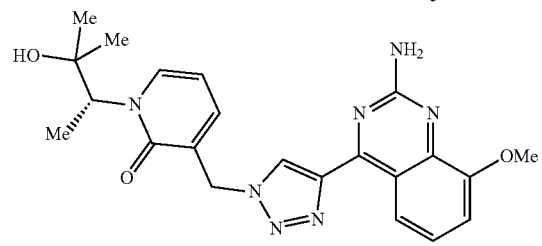
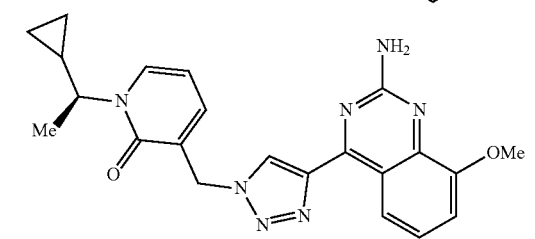
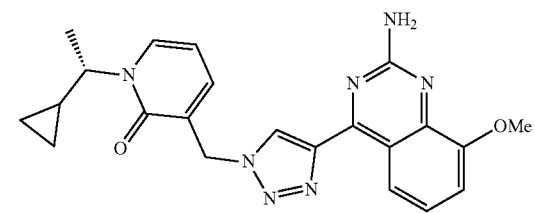 [SMILES: COc1cccc2c(-c3cn(Cc4cccn([C@@H](C)C5CC5)c4=O)nn3)nc(N)nc12]

-continued
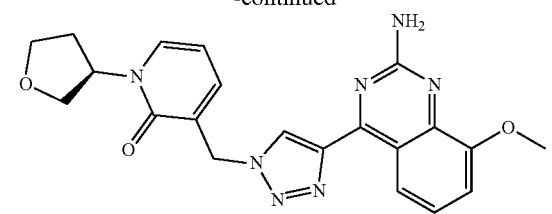
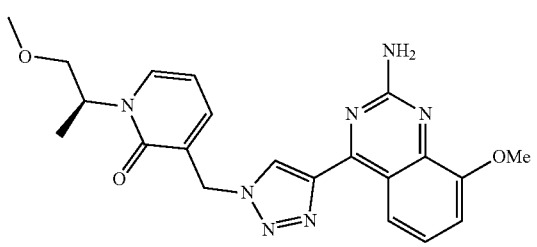
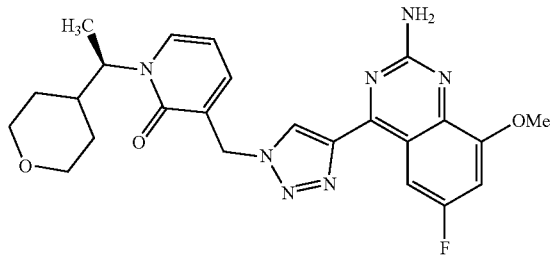 [SMILES: COc1cc(F)cc2c(-c3cn(Cc4cccn([C@H](C)C5CCOCC5)c4=O)nn3)nc(N)nc12]
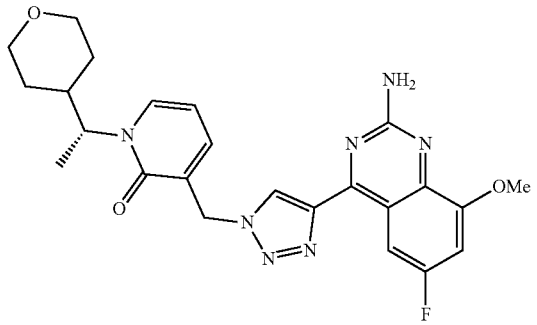
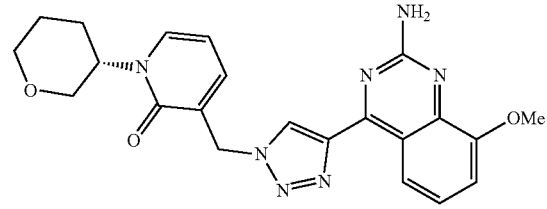 [SMILES: COc1cccc2c(-c3cn(Cc4cccn([C@H]5CCCOC5)c4=O)nn3)nc(N)nc12]
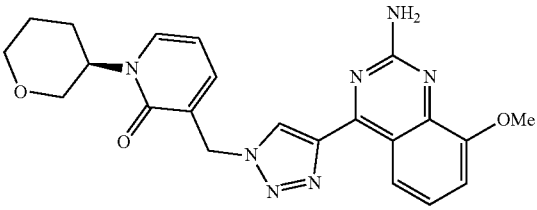 [SMILES: COc1cccc2c(-c3cn(Cc4cccn([C@@H]5CCCOC5)c4=O)nn3)nc(N)nc12]
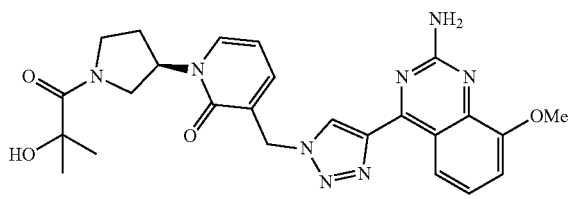
-continued
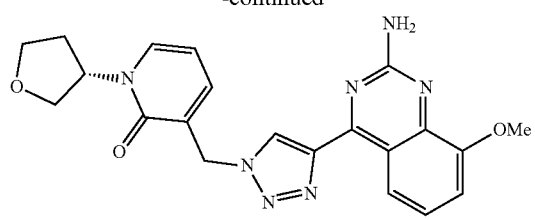
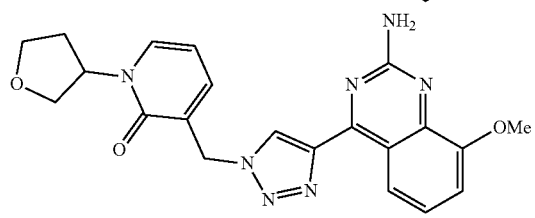
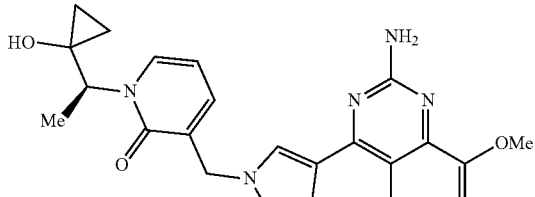
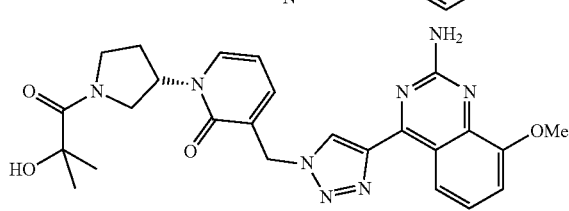
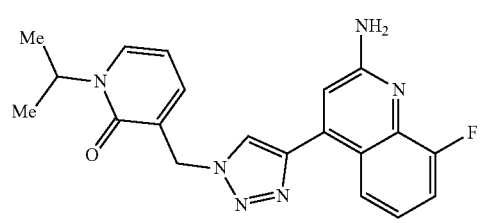
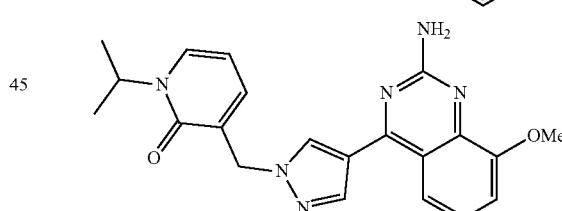
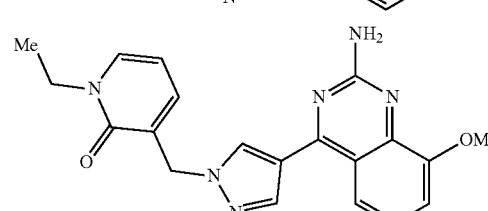
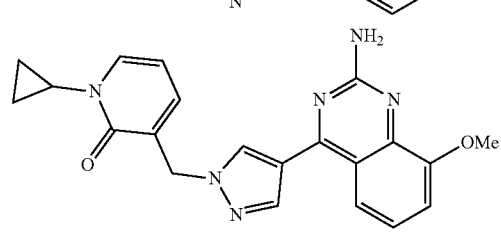

-continued

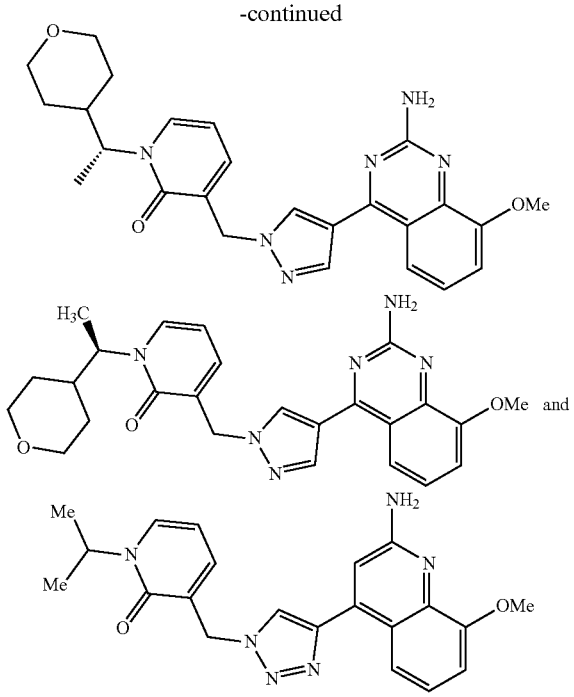

or a pharmaceutically acceptable salt, hydrate, or solvate thereof.

16. A pharmaceutical composition comprising a compound of claim 1 and a pharmaceutically acceptable excipient.

17. A method of treating a disease, disorder, or condition, mediated at least in part by the adenosine $A_{2A}$ receptor ($A_{2A}R$), or the adenosine $A_{2B}$ receptor ($A_{2B}R$), or the $A_{2A}R$ receptor and the $A_{2B}R$ receptor, said method comprising administering a therapeutically acceptable amount of a compound of claim 1 to a subject in need thereof.

18. The method of claim 17, wherein said disease, disorder, or condition is cancer.

19. The method of claim 18, wherein said cancer is a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone; or is glioblastoma, mesothelioma, renal cell carcinoma, gastric carcinoma, sarcoma, choriocarcinoma, cutaneous basocellular carcinoma, or testicular seminoma.

20. The method of claim 18, wherein said cancer is selected from the group consisting of melanoma, colorectal cancer, pancreatic cancer, breast cancer, prostate cancer, lung cancer, leukemia, a brain tumor, lymphoma, ovarian cancer, Kaposi's sarcoma, squamous cell carcinoma of the head and neck, bladder cancer, endometrial cancer, Merkel cell carcinoma, and gastroesophageal cancer.

21. A method of treating cancer in a subject, said method comprising administering to said subject an effective amount of a compound of claim 1 and at least one additional therapeutic agent.

22. The method in accordance with claim 21, wherein the at least one additional therapeutic agent is a chemotherapeutic agent, an immune-modulating agent, an inflammation-modulating agent, an immune- and inflammation-modulating agent, an anti-hypercholesterolemia agent, an anti-infective agent, or radiation.

23. The method in accordance with claim 21, wherein the at least one additional therapeutic agent is an immune checkpoint inhibitor, wherein said immune checkpoint inhibitor blocks the activity of at least one of PD1, PDL1, BTLA, LAG3, TIM-3, TIGIT, a B7 family member, or CTLA4.

24. The method in accordance with claim 23, further comprising a chemotherapeutic agent.

25. The method in accordance with claim 5, wherein the chemotherapeutic agent is selected from the group consisting of cisplatin, carboplatin, oxaliplatin, doxorubicin, and pemetrexed.

* * * * *

UNITED STATES PATENT AND TRADEMARK OFFICE
CERTIFICATE OF CORRECTION

PATENT NO. : 12,064,433 B2
APPLICATION NO. : 17/263016
DATED : August 20, 2024
INVENTOR(S) : Manmohan Reddy Leleti et al.

Page 1 of 1

It is certified that error appears in the above-identified patent and that said Letters Patent is hereby corrected as shown below:

On the Title Page

Item (72), please replace "Ehesan U I Sharif, Menlo Park, CA (US)" with -- Ehesan Ul Sharif, Menlo Park, CA (US) --.

In the Claims

In Claim 1, Column 100, Line 27, please replace "the subscript n is 0, 1, 2 or 3;" with -- the subscript n is 0, 1, 2, or 3; --.

In Claim 1, Column 100, Line 46, please replace "-C(O)NR$^d$R$^c$" with -- -C(O)NR$^d$R$^e$ --.

In Claim 1, Column 100, Line 50, please replace "R$^{10c}$ and" with -- R$^{10c}$, and --.

In Claim 4, Column 101, Line 45, please replace "R$^{10b}$ and R$^{1c}$" with -- R$^{10b}$, and R$^{10c}$ --.

In Claim 15, Column 110, Lines 10 to 17, please replace " 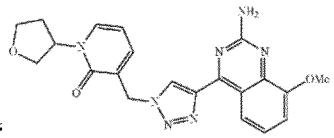 " with 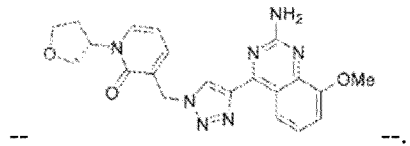 --.

In Claim 25, Column 112, Line 37, please replace "with claim 5" with -- with claim 24 --.

Signed and Sealed this
Fifth Day of November, 2024

Katherine Kelly Vidal
*Director of the United States Patent and Trademark Office*